US007994355B2

(12) United States Patent
Chen et al.

(10) Patent No.: US 7,994,355 B2
(45) Date of Patent: *Aug. 9, 2011

(54) METALLOCENE-BASED CHIRAL PHOSPHINE OR ARSINE LIGANDS

(75) Inventors: Wei-Ping Chen, Liverpool (GB); John Whittall, Lancaster (GB)

(73) Assignee: Solvias AG, Basel (CH)

( * ) Notice: Subject to any disclaimer, the term of this patent is extended or adjusted under 35 U.S.C. 154(b) by 809 days.

This patent is subject to a terminal disclaimer.

(21) Appl. No.: 10/586,287

(22) PCT Filed: Jan. 14, 2005

(86) PCT No.: PCT/GB2005/000112
§ 371 (c)(1),
(2), (4) Date: Sep. 29, 2006

(87) PCT Pub. No.: WO2005/068477
PCT Pub. Date: Jul. 28, 2005

(65) Prior Publication Data
US 2007/0161762 A1 Jul. 12, 2007

(30) Foreign Application Priority Data
Jan. 14, 2004 (GB) .................................. 0400720.9

(51) Int. Cl.
*C07F 15/02* (2006.01)
*C08F 4/70* (2006.01)
*C08F 4/80* (2006.01)
(52) U.S. Cl. .......... 556/143; 556/144; 556/57; 556/136; 556/137; 556/138; 502/152; 502/153; 502/154; 502/155; 502/208; 502/210; 502/213; 502/200
(58) Field of Classification Search .................. 556/143, 556/144, 145, 138, 140
See application file for complete search history.

(56) References Cited

U.S. PATENT DOCUMENTS

| 5,451,684 | A | | 9/1995 | McGarrity et al. |
| 5,466,844 | A | * | 11/1995 | Spindler et al. .................. 556/11 |
| 5,583,241 | A | * | 12/1996 | Spindler .......................... 556/11 |
| 5,856,540 | A | | 1/1999 | Jendralla |
| 5,925,778 | A | * | 7/1999 | Pugin ............................ 556/144 |
| 6,258,979 | B1 | | 7/2001 | Kagan et al. |
| 6,284,925 | B1 | * | 9/2001 | Knochel et al. ................ 564/415 |
| 6,777,567 | B2 | * | 8/2004 | Weissensteiner et al. ...... 556/16 |
| 2002/0065417 | A1 | | 5/2002 | Boaz et al. |
| 2003/0212284 | A1 | | 11/2003 | Weissensteiner et al. |
| 2005/0240007 | A1 | | 10/2005 | Knochel et al. |
| 2008/0076937 | A1 | * | 3/2008 | Pugin et al. ..................... 556/16 |

FOREIGN PATENT DOCUMENTS

| DE | 10219490 | 11/2003 |
| EP | 0 803 510 A | 10/1997 |
| WO | WO 98/15565 A | 4/1998 |
| WO | WO 00/14096 A | 3/2000 |
| WO | WO 00/37478 A | 6/2000 |

OTHER PUBLICATIONS

Butler et al. Organometallics 1986, 5, 320-1328.*
Troitskaya et al. Russian Chemical Bulletin 1999, 48(9), 1738-1743.*
Cullen et al. J. Am. Chem. Soc. 1980, 102, 988-993.*
Bieler, N. H. "Asymmetrische Hydroaminierung von Olefinen mit Iridium(I)-Diphosphin-Komplexen." Ph.D. dissertation, ETH Zurich, May 2000, p. 29.*
International Search Report in PCT/GB2005/000112 mailed May 10, 2005.
International Written Opinion in PCT/GB2005/000112 mailed May 10, 2005.
Patent Act of 1977, Search Report under Section 17(5), for GB Patent Application No. GB0500704.2, dated Jun. 10, 2005.
Patent Act of 1977, Written Opinion, for GB Patent Application No. GB0500704.2, dated Jun. 10, 2005.
Patent Act of 1977, letter from examiner regarding additional references, dated Aug. 23, 2005.
Troitskaya, et al. "Optically active (2-aminomethylferrocenyl)phosphines with the phosphorus chiral center" Russian Chemical Bulletin 1999, 48(9), 1738-1743.
Kim, et al. "Functionalized organometallic ligand. 1. Synthesis of some ferrocene derivatives of cyclohexyl- and cyclopentadienylphosphines" Bulletin of the Korean Chemical Society 1992, 13(6), 588-92.
Butler, et al. "Synthesis of derivatives of [alpha(dimethylamino)ethyl]ferrocene via lithiation reactions and the structure of 2-[alpha(dimethylamino)ethyl]-1,1'-tris(trimethylsilyl)ferrocene" Organometallics 1986, 5(7), 1320-8.
Gambs, et al. "Structural aspects of palladium and platinum complexes with chiral diphosphinoferrocenes relevant to the regio- and stereoselective copolymerization of CO with propene" Helvetica Chimica Acta 2001, 84(10), 3105-3126.
CAPLUS Accession No. 132:805612 (Abstract only) Troitskaya, et al. "Optically active (2-aminomethylferrocenyl)phosphines with the phosphorus chiral center" Russian Chemical Bulletin 1999, 48(9), 1738-1743.
CAPLUS Accession No. 118:191947 (Abstract only) Kim, et al. "Functionalized organometallic ligand. 1. Synthesis of some ferrocene derivatives of cyclohexyl- and cyclopentadienylphosphines" Bulletin of the Korean Chemical Society 1992, 13(6), 588-92.
CAPLUS Accession No. 105:443034 (Abstract only) Butler, et al. "Synthesis of derivatives of [alpha(dimethylamino)ethyl]ferrocene via lithiation reactions and the structure of 2-[alpha(dimethylamino)ethyl]-1,1'-tris(trimethylsilyl)ferrocene" Organometallics 1986, 5(7), 1320-8.
CAPLUS Accession No. 2001:862902 (Abstract only) Gambs, et al. "Structural aspects of palladium and platinum complexes with chiral diphosphinoferrocenes relevant to the regio-and stereoselective copolymerization of CO with propene" Helvetica Chimica Acta 2001, 84(10), 3105-3126.

* cited by examiner

*Primary Examiner* — Rip A. Lee
(74) *Attorney, Agent, or Firm* — Wenderoth, Lind & Ponack, L.L.P.

(57) ABSTRACT

The present invention relates to metallocene-based phosphine ligands having chirality at phosphorus and at least one other element of chirality (planar chirality and/or chirality at carbon); and to the use of such ligands in asymmetric transformation reactions to generate high enantiomeric excesses of formed compounds. A method for the preparation of ligands according to the invention involving the conversion of the ortho-lithiated substituted metallocene to a phosphine chiral at phosphorus is also disclosed.

19 Claims, No Drawings

METALLOCENE-BASED CHIRAL PHOSPHINE OR ARSINE LIGANDS

This invention relates to novel metallocene-based phosphine ligands incorporating up to four elements of chirality, planar chirality, chirality at phosphorus, and optionally chirality at carbon and axial chirality, and methods for their preparation. In addition, this invention relates to the metal-ligand complexes that can be used as catalysts or precatalysts for asymmetric transformation reactions to generate products of high enantiomeric excess. Similarly structured arsines are also within the scope of this invention.

Ferrocene as a backbone for diphosphine ligands was introduced by Kumada and Hayashi based on the pioneering work of Ugi related to the synthesis of enantiopure substituted metallocenes[1]. A number of these ligands are shown below:

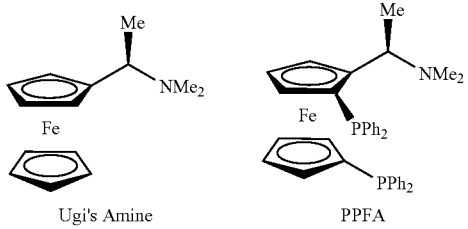

Ugi's Amine      PPFA

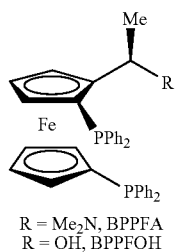

R = Me$_2$N, BPPFA
R = OH, BPPFOH

Ppfa as well as bppfa and bppfoh proved to be effective ligands for the catalysis of a variety of asymmetric transformations. From this starting point, many chiral ferrocene-based bisphosphine ligands with a range of structural variation have been developed in the last few years.

Certain types of known ligands exhibit both planar and carbon chirality:

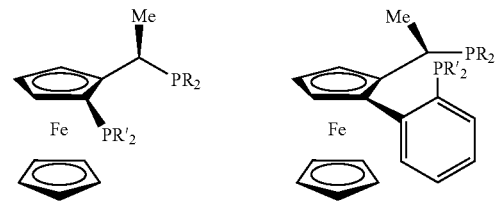

Josiphos: R = Cy, R' = Ph      Walphos
PPF-tBu$_2$: R = t-Bu, R' = Ph
Xyliphos: R = 3,5-Me$_2$Ph, R' = Ph
cy$_2$PF-Pcy$_2$: R = R' = Cy

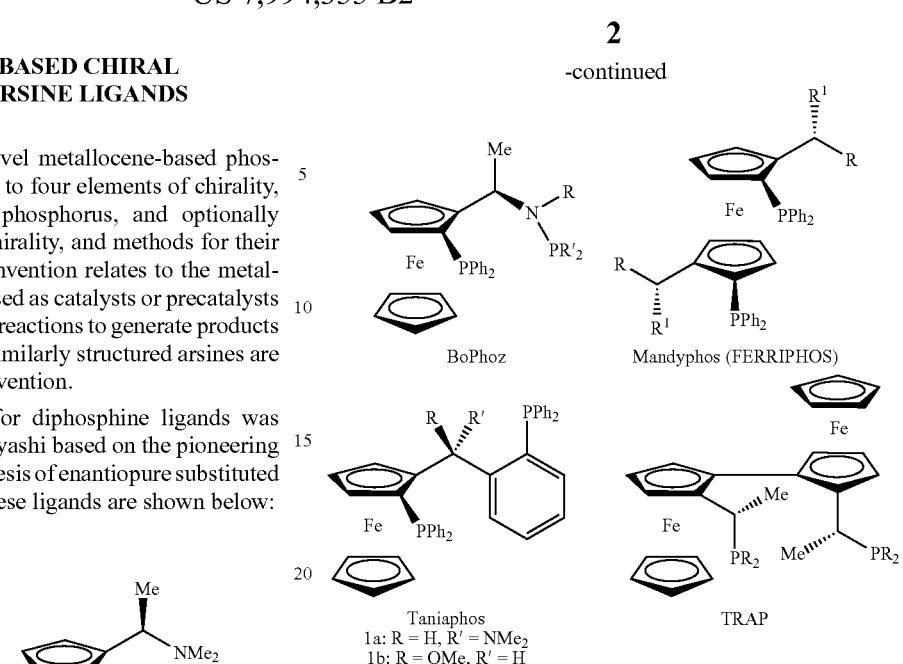

BoPhoz      Mandyphos (FERRIPHOS)

Taniaphos
1a: R = H, R' = NMe$_2$
1b: R = OMe, R' = H

TRAP

Togni and Spindler[2] have reported a class of non-C$_2$-symmetrical ferrocene-based bisphosphines: the Josiphos-type ligands. Josiphos ligands are in widespread commercial use, having been found effective for Rh-catalyzed hydrogenation of α-acetamidocinnamate, dimethyl itaconate, and β-ketoesters. Because the two phosphine groups are introduced into the ligand in consecutive steps with high yields, a variety of ligands are available with widely differing steric and electronic properties. The ligands have already been applied in three production processes[3], several pilot processes and many other syntheses. For example, PPF-tBu2, a Josiphos type ligand with a di-(tert-butyl)phosphino group, has been applied as the ligand in asymmetric hydrogenation for commercial synthesis of (+)-biotin.[4] Another notable example is the application of XyliPhos in the Ir-catalyzed hydrogenation of imines for the synthesis of the herbicide (S)-metolachlor[5].

Bophoz[6] is a combination of a phosphine and an aminophosphine and is prepared in 3 steps from ppfa with high overall yields. The ligand is air stable and effective for the hydrogenation of enamides, itaconates and α-keto acid derivatives. As observed for several ligands forming seven-membered chelates, high activities can be reached and TONs up to 10,000 have been claimed. The full scope of this modular ligand class has not yet been explored.

A class of non-C$_2$-symmetrical, ferrocene-based 1,5-diphosphine ligands, Taniaphos, has been developed by Knochel[7,8]. Compared to the Josiphos ligands, Taniaphos has an additional phenyl ring inserted at the side chain of the Ugi amine. Taniaphos gave excellent results in Rh- and Ru-catalyzed asymmetric hydrogenation. The configuration of α-position of Taniaphos plays an important role in the enantioselectivities and activities. The Taniaphos 1b with αS configuration leads to higher enantioselectivities and activities than 1a with αR configuration in a wide range of asymmetric transformations.

Weissensteiner and Spindler[9] have reported a series of structurally different ferrocene-based 1,5-diphosphine ligands, Walphos. Like Josiphos, Walphos is modular and is also made from the Ugi amine. It shows promise for the enantioselective hydrogenation of olefins and ketones.

Mandyphos is a bidentate version of ppfa with C$_2$ symmetry, where in addition to the PPh$_2$ moieties, R and R' can be used for fine tuning the functionality of the ligand[10]. The scope of this ligand family has not yet been fully explored, but preliminary results indicate high enantioselectivities for the Rh-catalyzed hydrogenation of enamides, itaconates and enol acetates.

The TRAP ligands developed by Ito[11] form 9-membered metallocycles. However, it is not clear whether the cis-isomer, present in small amounts, or the major trans-isomer is responsible for the catalytic activity. Up to now only a few different PR2 fragments have been tested, but it is clear that the choice of R strongly affects the catalytic performance. The Rh complexes work best at very low pressures of 0.5±1 bar and effectively reduces indole-derivatives, enamides and itaconic acid derivatives.

Another class of known ligands exhibit only planar chirality:

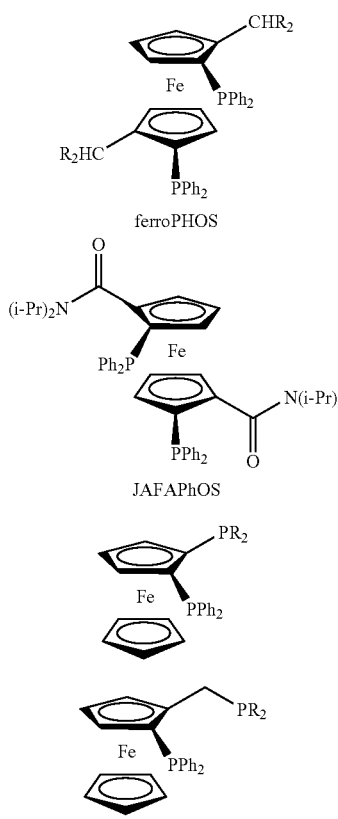

Kang[12] reported the $C_2$-symmetry FerroPHOS with only planar chirality. FerroPHOS ligands are air-stable and are very efficient for the asymmetric hydrogenation of various dehydroamino acid derivitives (up to 99% ee).

Another $C_2$-symmetry planar chiral diphosphine, JAFAPhos, has been developed by Jendralla[13]. JAFAPhos gave excellent results in asymmetric hydrogenation, allylic alkylation, Grignard cross coupling and aldol reactions.

Kagan[14] reported plane chiral ferrocene-based bisphosphorus ligands 2 and 3, and up to 95% ee's have been obtained in asymmetric hydrogenation of dimethyl itaconate using these ligands as catalyst.

Another class of known diphosphine ligands exhibit chirality only at the phosphorus atoms:

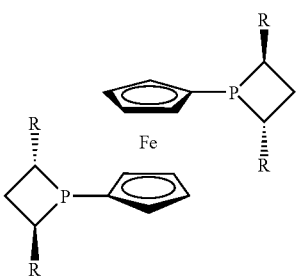

FerroTane

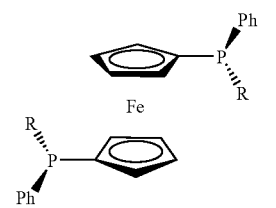

4a: R = o-anisyl
4b: R = 1-naphthyl

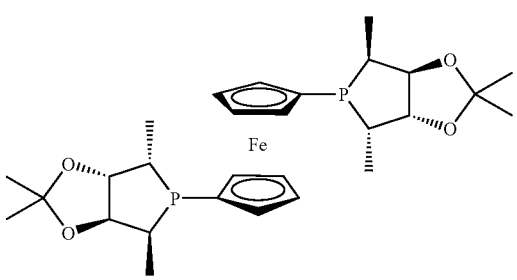

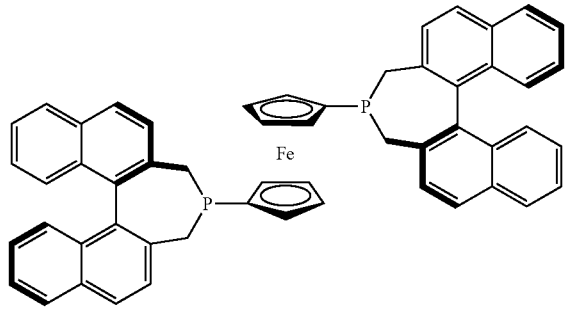

f-binaphane

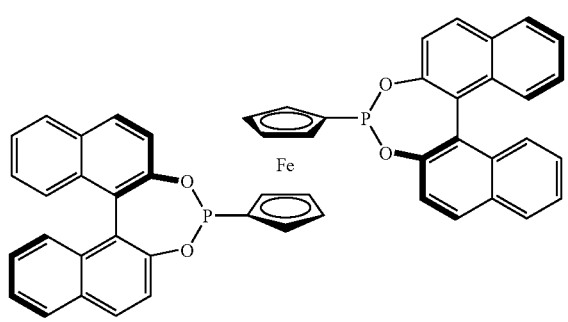

The synthesis of chiral 1,1'-bis(phosphetano) ferrocenes (FerroTANE) has been independently reported by Marinetti[15] and Burk[16]. FerroTANE has been successfully applied in Rh-catalyzed hydrogenation of itaconates and (E)-β-(acylamino) acrylates[17].

Mezzetti[18] and van Leeuwen[19] have independently reported P-chiral ferrocenyl bisphosphines 4a and 4b. These two ligands have shown excellent enantioselectivities (up to 99% ee) for asymmetric hydrogenation of α-dehydroamino acid derivatives.

Zhang has reported a 1,1'-bis(Phospholanyl) ferrocene ligand 5 with ketal substitutes at the 3 and 4 positions.[20] The ligand has shown excellent enantioselectivities in hydrogenation of β-dehydroamino acid derivatives. The ketal groups of the ligand are important for achieving the high enantioselectivity, since the corresponding ligand without ketal groups only provides moderate ee's. Zhang has also developed a 1,1'-bis(dinaphthophosphepinyl) ferrocene ligand, f-binaphane, which has been successfully applied in the Ir-catalyzed hydrogenation of acyclic aryl imines.[21]

Reetz has developed a binaphthol-derived ferrocene-based bisphosphonite ligand 6[22], which has shown excellent reactivities and enantioselectivities in Rh-catalyzed hydrogenation of itaconates and α-dehydroamino acid derivatives.

Another class of known ligands exhibits both planar and phosphorus chirality:

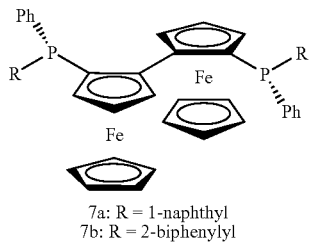

7a: R = 1-naphthyl
7b: R = 2-biphenylyl

Van Leeuwen has reported ferrocene-based bisphosphines combining planar and phosphorus chirality 4a and 4b[23]. These two ligands have shown excellent enantioselectivities (up to 99% ee) for asymmetric allylic alkylations.

Thus, most of the known ferrocene-based diphosphines contain planar and carbon chirality, only planar chirality or only phosphorus chirality. More recently, Togni reported the first tridentate ferrocene-based phosphine ligand 12 combining planar, phosphorus and carbon chirality.[24]

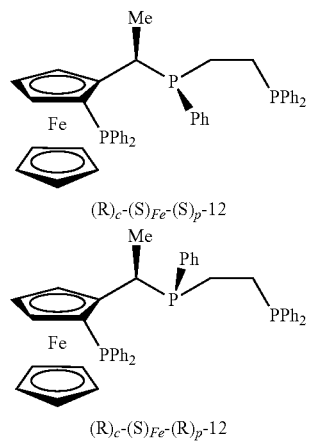

It would be advantageous to design bisphosphine ligands incorporating up to three elements of chirality, planar chirality, chirality at phosphorus, and chirality at carbon for use in enantioselective catalysis. It would also be advantageous to design ligands that exhibit three different types of chirality; carbon, planar and phosphorus.

According to the present invention there is provided a metallocene-based phosphine having up to three or four elements of chirality; planar chirality, chirality at phosphorus, and optionally chirality at carbon and axial chirality.

The invention also provides a metallocene-based arsine having up to three elements of chirality; planar chirality, chirality at arsenic, and optionally chirality at carbon. In the following description reference will be made for convenience to phosphine ligands. It should be understood that although phosphines are the preferred ligands in accordance with the invention, the corresponding arsines are also within the scope of the invention.

Similarly, whilst ferrocene based ligands are preferred, other suitable metals may be used in the ligands of the invention, and hence reference is made herein to metallocenes generally.

The invention further provides a metallocene-based diphosphine having planar, phosphorus and carbon chirality.

Ligands according to the invention have particular advantages over prior art ligands because the provision of up to three or four chiralities allows the designer of a ligand greater scope than has hitherto been the case to design ligands for a particular purpose.

Preferred ligands in accordance with the invention are selected from ligands having Formula (I), (II) or (III):

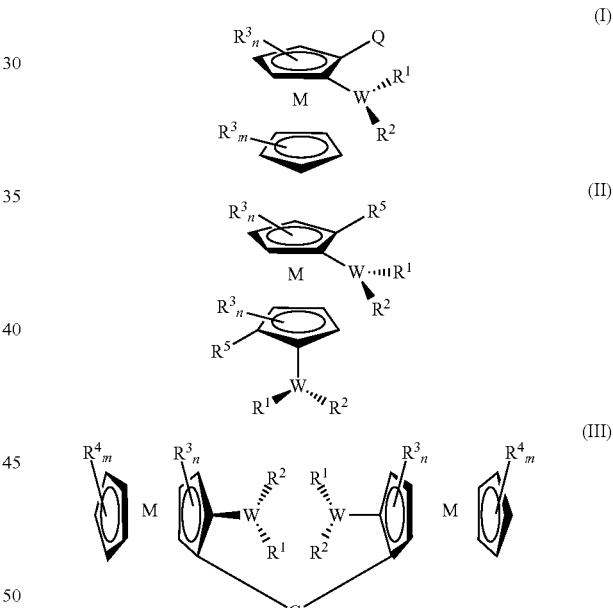

wherein
W is phosphorus or arsenic;
M is a metal;
$R^1$ and $R^2$ are different from each other, and are independently selected from from substituted and unsubstituted, branched- and straight-chain alkyl, alkoxy, alkylamino, substituted and unsubstituted cycloalkyl, substituted and unsubstituted cycloalkoxy, substituted and unsubstituted cycloalkylamino, substituted and unsubstituted carbocyclic aryl, substituted and unsubstituted carbocyclic aryloxy, substituted and unsubstituted heteroaryl, substituted and unsubstituted heteroaryloxy, substituted and unsubstituted carbocyclic arylamino and substituted and unsubstituted heteroarylamino, wherein the or each heteroatom is independently selected from sulphur, nitrogen, and oxygen;

R³ and R⁴ are the same or different, and are independently selected from substituted and unsubstituted, branched- and straight-chain alkyl, substituted and unsubstituted cycloalkyl, substituted and unsubstituted carbocyclic aryl, and substituted and unsubstituted heteroaryl wherein the or each heteroatom is independently selected from sulphur, nitrogen, and oxygen;

n is 0 to 3;

m is 0 to 5;

Q is selected from:

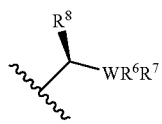

wherein W is phosphorus or arsenic;

$R^6$ and $R^7$ are the same or different, and are independently selected from substituted and unsubstituted, branched- and straight-chain alkyl, alkoxy, alkylamino, substituted and unsubstituted cycloalkyl, substituted and unsubstituted cycloalkoxy, substituted and unsubstituted cycloalkylamino, substituted and unsubstituted carbocyclic aryl, substituted and unsubstituted carbocyclic aryloxy, substituted and unsubstituted heteroaryl, substituted and unsubstituted heteroaryloxy, substituted and unsubstituted carbocyclic arylamino and substituted and unsubstituted heteroarylamino, wherein the or each heteroatom is independently selected from sulphur, nitrogen, and oxygen;

and $R^8$ is selected from hydrogen, substituted and unsubstituted, branched- and straight-chain alkyl, substituted and unsubstituted cycloalkyl, substituted and unsubstituted carbocyclic aryl, and substituted and unsubstituted heteroaryl wherein the or each heteroatom is independently selected from sulphur, nitrogen, and oxygen; or Q is selected from:

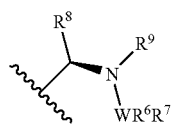

wherein W is phosphorus or arsenic;

$R^6$, $R^7$ and $R^8$ are, independently, as previously defined; and $R^9$ is selected from hydrogen, substituted and unsubstituted, branched- and straight-chain alkyl, substituted and unsubstituted cycloalkyl, substituted and unsubstituted carbocyclic aryl, and substituted and unsubstituted heteroaryl wherein the or each heteroatom is independently selected from sulphur, nitrogen, and oxygen; or Q is selected from:

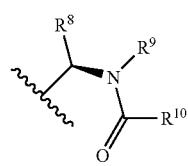

wherein $R^6$, $R^7$, $R^8$ and $R^9$ are, independently, as previously defined; and $R^{10}$ is selected from hydrogen, substituted and unsubstituted, branched- and straight-chain alkyl, substituted and unsubstituted cycloalkyl, substituted and unsubstituted carbocyclic aryl, and substituted and unsubstituted heteroaryl wherein the or each heteroatom is independently selected from sulphur, nitrogen, and oxygen; or Q is selected from:

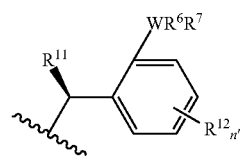

wherein W is phosphorus or arsenic;

$R^6$, $R^7$ are, as previously defined; $R^{11}$ is selected from $OR^{13}$, $SR^{13}$, $NHR^{13}$, $NR^{13}R^{14}$, wherein $R^{13}$ and $R^{14}$ are the same or different and are independently selected from hydrogen, substituted and unsubstituted, branched- and straight-chain alkyl, substituted and unsubstituted cycloalkyl, substituted and unsubstituted carbocyclic aryl, and substituted and unsubstituted heteroaryl wherein the or each heteroatom is independently selected from sulphur, nitrogen, and oxygen; $R^{12}$ is selected from hydrogen, halogen, $OR^{13}$, $SR^{13}$, $NR^{13}R^{14}$, substituted and unsubstituted, branched- and straight-chain alkyl, substituted and unsubstituted cycloalkyl, substituted and unsubstituted carbocyclic aryl, and substituted and unsubstituted heteroaryl wherein the or each heteroatom is independently selected from sulphur, nitrogen, and oxygen; wherein $R^{13}$, $R^{14}$ are, as previously defined and n' is 0 to 4;

or Q is selected from:

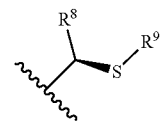

wherein $R^8$ and $R^9$ are as previously defined;

$R^5$ is selected from:

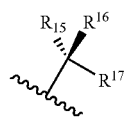

wherein $R^{15}$, $R^{16}$ and $R^{17}$ are the same or different and are independently selected from hydrogen, $OR^{13}$, $SR^{13}$, $NR^{13}R^{14}$, substituted and unsubstituted, branched- and straight-chain alkyl, substituted and unsubstituted cycloalkyl, substituted and unsubstituted carbocyclic aryl, and substituted and unsubstituted heteroaryl wherein the or each heteroatom is independently selected from sulphur, nitrogen, and oxygen; wherein $R^{13}$, $R^{14}$ are, as previously defined; or $R^5$ is selected from:

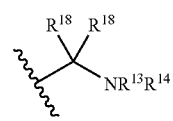

wherein $R^{13}$, $R^{14}$ are as previously defined; the two geminal substituents $R^{18}$ together are a doubly bonded oxygen atom (i.e. $(R^{18})_2$ is =O), or each substituent $R^{18}$ on its own is hydrogen; and G is selected from the group consisting of: —CONH—R*—NHCO—, —CO—OR*O—CO—, —CO—R*CO—, —CH=N—R*—N=CH—, —CH$_2$NH—R*—NHCH$_2$—, —CH$_2$NHCO—R*—CONHCH$_2$—, —CH(R$^8$)NH—R*—NH(CH(R$^8$)—, —CH(R$^8$)NHCO—R*—CONHCH(R$^8$)—, —CONH—R—NHCO—, —CO—ORO—CO—, —CO—RCO—, —CH=N—R—N=CH—, —CH$_2$NH—R—NHCH$_2$—, —CH$_2$NHCO—R—CONHCH$_2$—, —CH(R$^8$)NH—R—NH(CH(R$^8$)—, —CH(R$^8$)NHCO—R—CONHCH(R$^8$)—; wherein $R^8$ is, independently, as previously defined; —R*— and —R— are selected from the group consisting of:

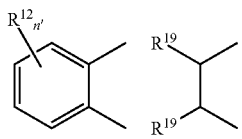

wherein $R^{12}$ is as previously defined; $R^{19}$ is selected from hydrogen, substituted and unsubstituted, branched- and straight-chain alkyl, substituted and unsubstituted cycloalkyl, substituted and unsubstituted carbocyclic aryl, and substituted and unsubstituted heteroaryl wherein the or each heteroatom is independently selected from sulphur, nitrogen, and oxygen; or $(R^{19})_2$ is —(CH$_2$)$_{m'}$—, n' is 0 to 4; and m' is 1 to 8;

The invention also relates to the enantiomers of the ligands described above, the enantiomers having the Formulae (IV), (V) and (VI):

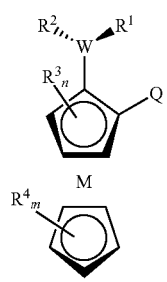

(IV)

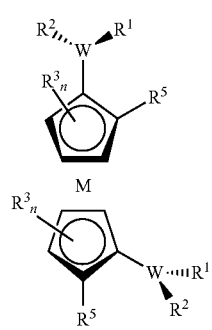

(V)

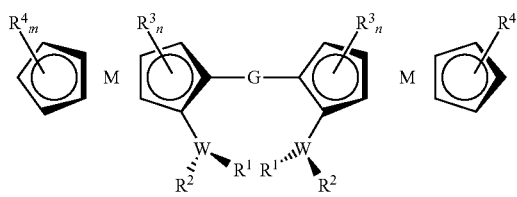

(VI)

wherein each of W, M, $R^{1-19}$, Q, G, n, m, n' and m' have the same meanings as assigned above, with chirality changes in the substituent groups where required.

Also provided in accordance with the invention are diastereomers of the ligands described above, the diastereomers having the Formulae (VII), (VIII) and (IX):

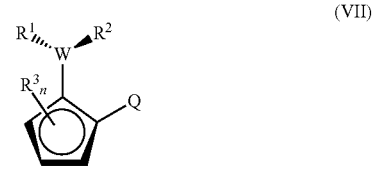

(VII)

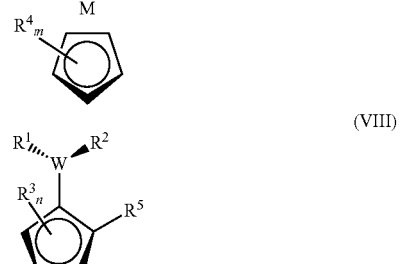

(VIII)

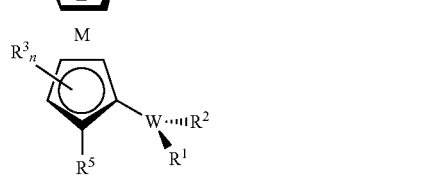

(IX)

wherein each of W, M, $R^{1-19}$, Q, G, n, m, n' and m' have the same meanings as assigned above, with chirality changes in the substituent groups where required.

The introduction of phosphorus chirality may enhance the chiral discrimination produced by the catalyst when a matching among the planar chirality, carbon chirality, axial chirality and the chirality of phosphorus can be achieved. (Examples 59 to 67 below demonstrate that a matching catalyst may give high ee and a mismatching one may give low ee.)

Also provided in accordance with the invention is a transition metal complex containing transition metal coordinated to the ligand of the invention. The metal is preferably a Group VIb or a Group VIII metal, especially rhodium, ruthenium, iridium, palladium, platinum and nickel.

Synthesis of ferrocene-based phosphorus chiral phosphines may be effected with the use of a suitable chiral ortho-directing group, for example in accordance with the following schemes:

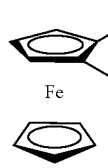
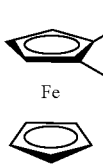
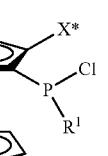
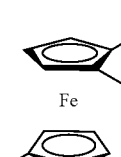

Examples of suitable chiral directing groups:

$X^* =$

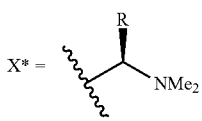
(ref. 25)

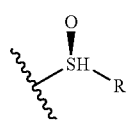
(ref. 26)

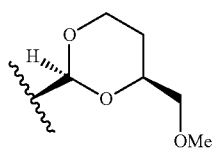
(ref. 27)

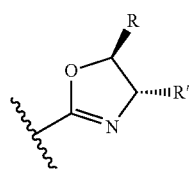
(ref. 28)

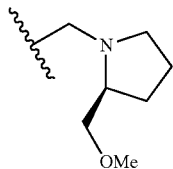
(ref. 29)

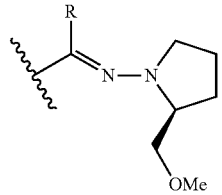
(ref. 30)

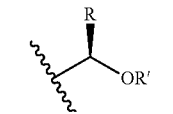
(ref. 31)

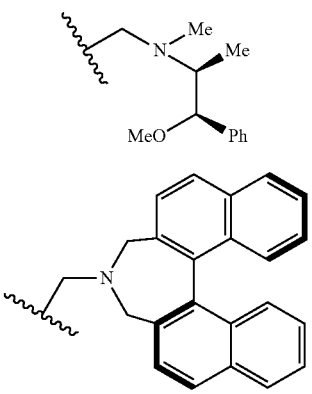
(ref. 32)

(ref. 33)

(Similar schemes may be used to synthesise the corresponding arsines, and other metallocenes.)

Accordingly, the invention provides a method for preparing a phosphine ligand chiral at phosphorus comprising providing a metallocene-based substrate having a chiral or achiral directing substituent on one or both rings, and subjecting the substituted metallocene to an ortho-lithiation step before subsequently converting the ortho-lithiated substrate to a phosphine chiral at phosphorus.

Methods for the preparation of ligands having Formula (I) and (III) will now be more particularly described.

For example, one such method comprises providing a compound of the Formula (X) (optionally substituted on one or both cyclopentadiene rings with $R^3_n$ (top ring) and/or $R^4_m$ (bottom ring)):

(X)

wherein X* is chiral directing group, and is preferably selected from the group consisting of:

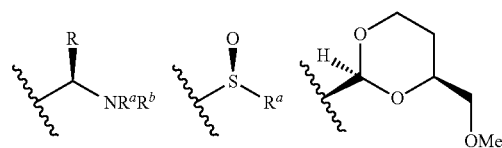

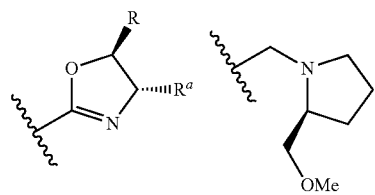

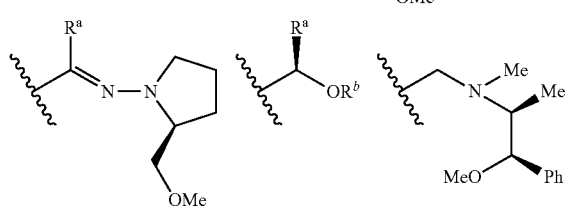

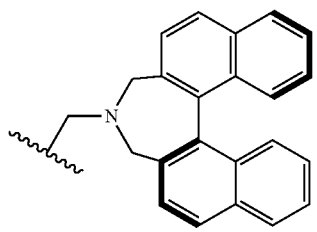

wherein

R, $R^a$ and $R^b$ are same or different, and are independently selected from hydrogen, substituted and unsubstituted, branched- and straight-chain alkyl, substituted and unsubstituted cycloalkyl, substituted and unsubstituted carbocyclic aryl, and substituted and unsubstituted heteroaryl wherein the or each heteroatom is independently selected from sulphur, nitrogen, and oxygen; ortho-lithiating the substrate; reacting the ortholithiated substrate with an $R^1$ substituted phosphine or arsine, and then with an $R^2$-bearing Grignard reagent or organolithium compound, and converting X* to Q or G as appropriate.

One particularly preferred X* group is

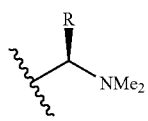

The ortho-lithiation step is preferably a mono-ortho-lithiation step using n-butyllithium, sec-butyllithium or tert-butyllithium. The resulting monolithium compound is preferably reacted in situ with a dichlorophosphine of the formula $R^1PCl_2$ followed by reacting with an organometallic reagent of the formula $R^2Z$, wherein $R^1$ and $R^2$ are as defined above; Z is Li or MgY wherein Y is a halide. These steps are performed to obtain phosphorus chiral compound having formula XI (optionally substituted on one or both cyclopentadiene rings with $R^3{}_n$ (top ring) and/or $R^4{}_m$ (bottom ring)):

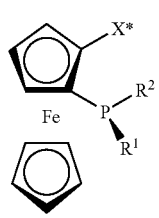
(XI)

The synthesis preferably proceeds by converting compound (XI) to compound XII, XIII, or XIV:

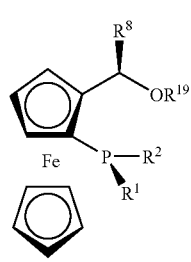
(XII)

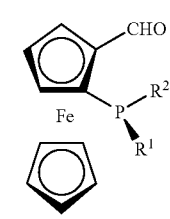
(XIII)

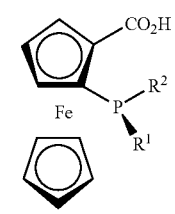
(XIV)

wherein $R^{19}$ is an acyl group, and $R^1$, $R^2$ are as previously defined; and then:

reacting compound XII with a secondary phosphine of the formula $R^6R^7PH$ wherein $R^6$, $R^7$ are, as previously defined, to obtain the diphosphine combining planar, phosphorus and carbon chirality having formula XV:

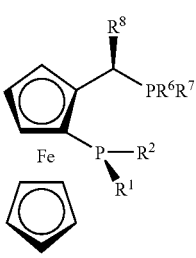
(XV)

or;

reacting compound XII with an amine of the formula $R^9NH_2$ wherein $R^9$ is, as previously defined, to obtain compound XVI:

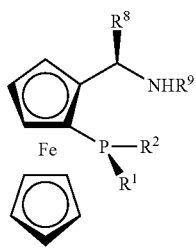

(XVI)

or;

reacting compound XII with an amine of the formula XVII:

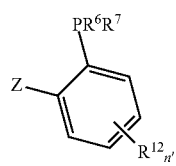

(XVII)

wherein $R^6$, $R^7$, $R^{12}$ and n' are, as previously defined, and Z is MgY (Y being a halide) or Li, to obtain compound XVIII:

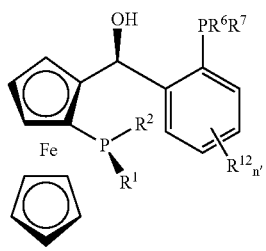

(XVIII)

or;

reacting compound XII with an amine of the formula $H_2N$—$R^*$—$NH_2$ or $H_2N$—R—$NH_2$ wherein $R^*$ and R are, as previously defined, to obtain compound XIX and XX:

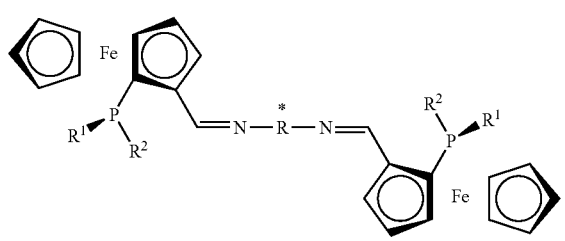

(XIX)

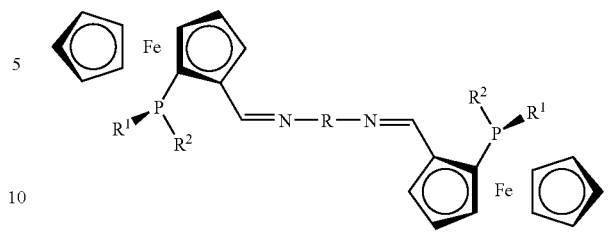

(XX)

or;

reacting compound XIII with an amine of the formula $H_2N$—$R^*$—$NH_2$ or $H_2N$—R—$NH_2$ wherein $R^*$ and R are, as previously defined, to obtain compound XXI and XXII:

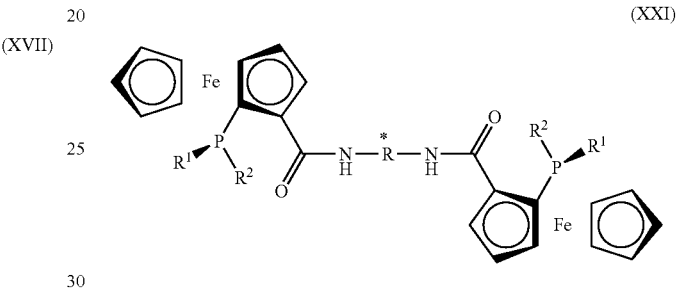

(XXI)

(XXII)

Compound XVI may be reacted with a halophosphine of the formula $R^6R^7PY$ wherein $R^6$, $R^7$ are, as previously defined, and Y is chlorine, bromine or iodine, to obtain compound XXIII:

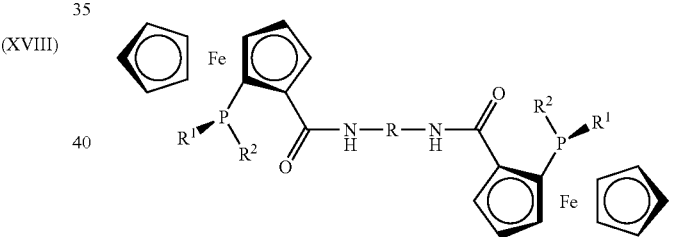

(XXIII)

Alternatively, compound XVI may be reacted with an acid derivative of the formula $R^{10}COY$ wherein $R^{10}$ is, as previously defined, and Y is a halide, a sulphate, an imidazole, $R^{10}COO$— or hydrogen, to obtain compound XXIV:

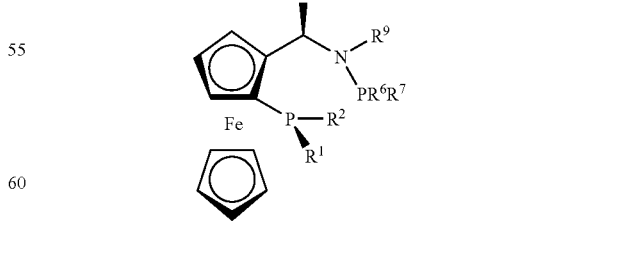

(XXIV)

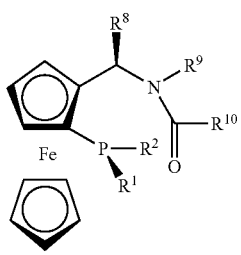

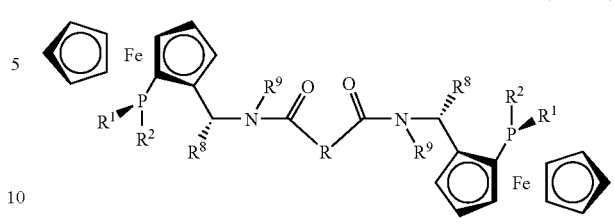
(XXVIII)

Alternatively compound XVI (in which R⁹ is hydrogen) may be reacted with an aldehyde of the formula OHC—R*—CHO or OHC—R—CHO wherein R* and R are, as previously defined, to obtain the compounds having Formulae XXV and XXVI:

Compound XVIII may be converted into compound XXIX:

(XXV)

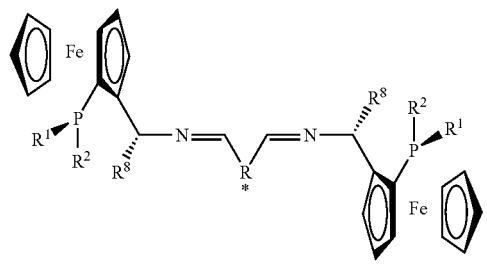

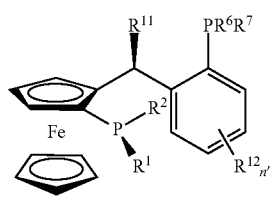
XXIX

Compounds XIX, XX, XXI, XXII, XXV, XXVI, XXVII, XXVIII may be reduced to obtain respective compounds XXX, XXXI, XXXII, XXXIII, XXXIV, XXXV, XXXVI, XXXVII:

(XXVI)

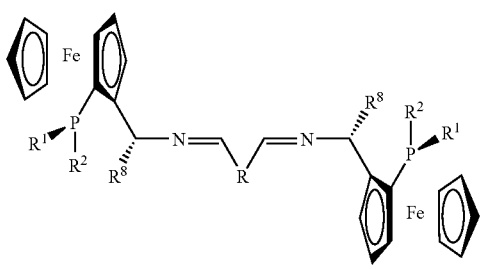

(XXX)

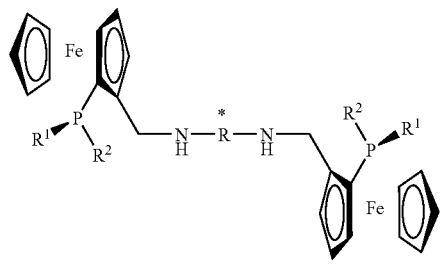

Alternatively compound XVI may be reacted with an acid derivative of the formula YOC—R*—COY and YOC—R—COY wherein R*, R and Y are, as previously defined, to obtain the compounds having Formulae XXVII and XXVIII:

(XXXI)

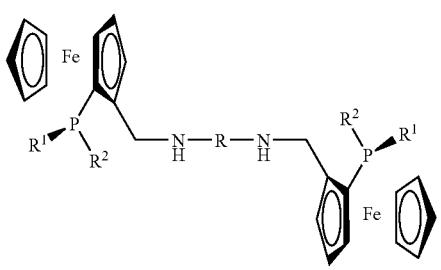

(XXVII)

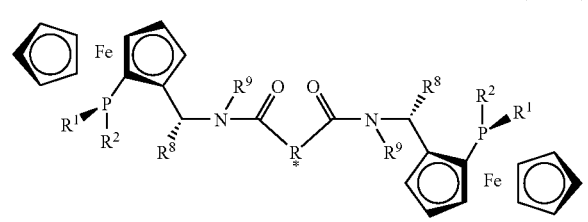

(XXXII)

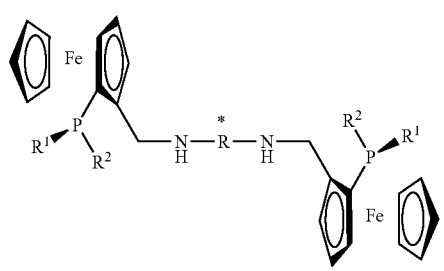

-continued
(XXXIII)
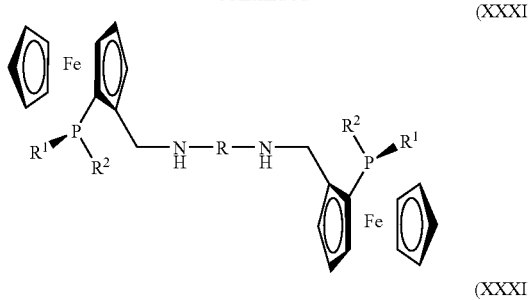
(XXXIV)
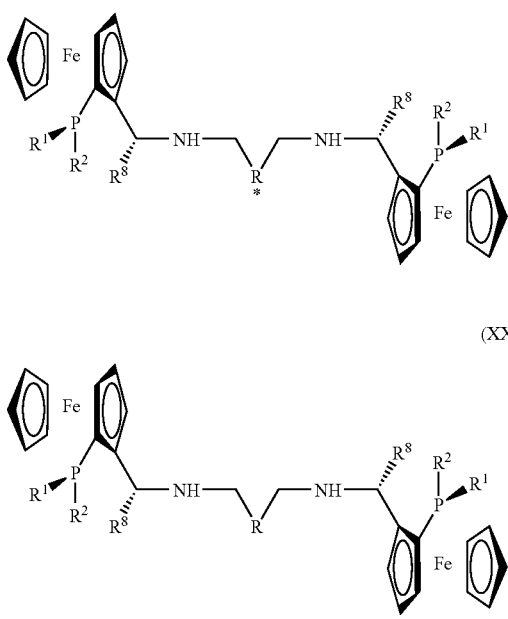
(XXXV)
(XXXVI)
(XXXVII)
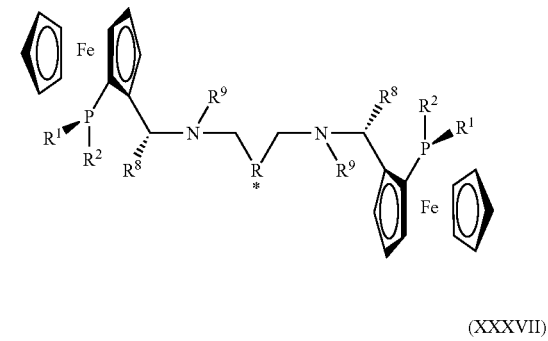
Synthesis of metallocene-based phosphines chiral at phosphorus may be also effected with the use of enantioselective ortho-lithiation:
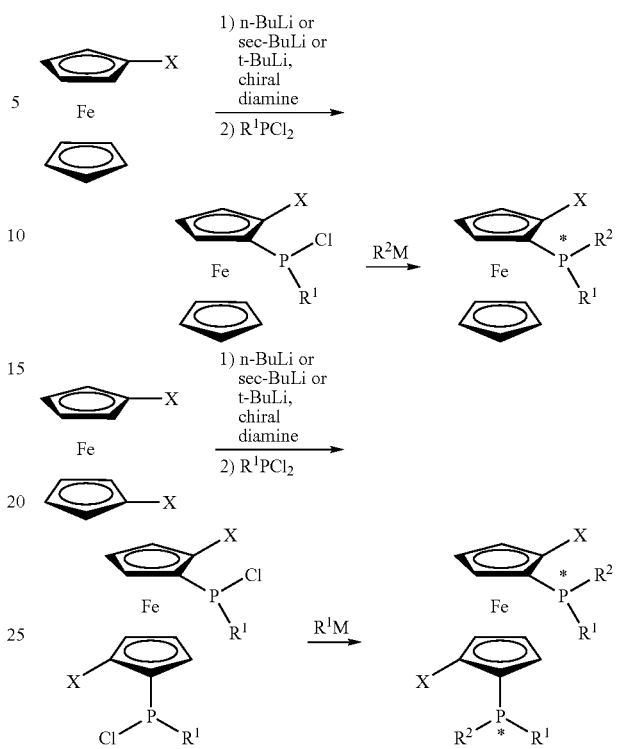
Examples of suitable achiral directing groups:
(ref. 34)
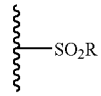
(ref. 34)
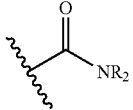
(ref. 35)
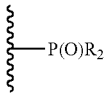
(ref. 36)
Chiral Diamine:
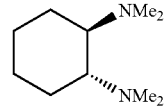
(ref. 34)
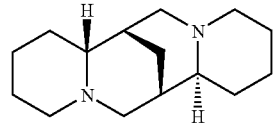
(ref. 35)

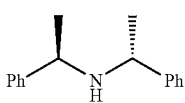
(ref. 36)

Accordingly, the invention provides a method for preparing a chiral diphosphine ligand comprising a metallocene-based substrate having an achiral directing substituent on one or both rings, and subjecting the substituted metallocene to an enantioselective ortho-lithiation step before subsequently converting the ortho-lithiated substrate to phosphorus chiral phosphines.

Thus, one method according to the present invention for preparing the ligand of Formula (I) or (III) comprises providing a compound of the formula XXXVII:

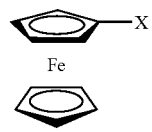
(XXXVII)

wherein X is an achiral directing group, and is preferably selected from:

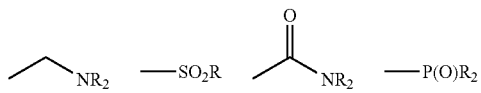

and subjecting the compound to enantioselective mono-ortho-lithiation using n-butyllithium or sec-butyllithium or tert-butyllithium in the presence of a homochiral tertiary amine, and reacting the resulting chiral monolithium compound in situ with a dichlorophosphine of the formula $R^1PCl_2$ followed by reacting with an organometallic reagent of the formula $R^2M$, wherein $R^1$ and $R^2$ are as defined hereinabove; M is Li or MgX wherein X is a halide, to obtain phosphorus chiral compound having formula XXXVIIII:

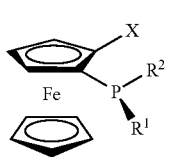
(XXXVIII)

and converting compound XXXVIII to compound (I) or (III).

One method according to the invention for preparing the ligand of Formula (II) comprises providing a compound of the Formula XXXIX:

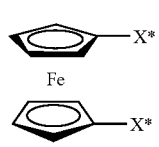
(XXXIX)

wherein X* is as previously defined; and subjecting the compound to bis-ortho-lithiation using n-butyllithium, sec-butyllithium or tert-butyllithium, and reacting the resulting bis-lithium compound in situ with a dichlorophosphine of the formula $R^1PCl_2$ followed by reacting with an organometallic reagent of the formula $R^2Z$, wherein $R^1$ and $R^2$ are as previously defined; Z is Li or MgY wherein Y is a halide, to obtain a phosphorus chiral compound having formula XXXX:

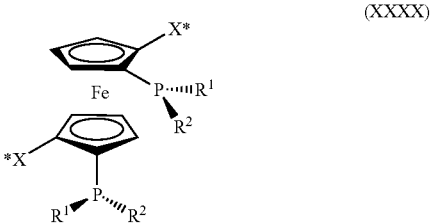
(XXXX)

and converting compound XXXX to compound (II).

The invention will now be more particularly illustrated with reference to the following Examples.

EXAMPLE 1

($R_C$, $S_{Fe}$, $S_P$)-2-[(1-N,N-Dimethylamino)ethyl]-1-[(2-methoxyphenyl)phenylphosphino]ferrocene [($R_C$, $S_{Fe}$, $S_P$)-2]

To a solution of (R)—N,N-dimethyl-1-ferrocenylethylamine [(R)-Ugi's amine, (R)-1] (3.86 g, 15 mmol) in $Et_2O$ (50 mL) was added 1.7 M t-BuLi solution in pentane (9.7 mL, 16.5 mmol) over 10 min via a syringe at −78° C. After addition was completed, the mixture was warmed to room temperature, and stirred for 1.5 h at room temperature. The resulting red solution was cooled to −78° C. again, and dichlorophenylphosphine (2.24 mL, 16.5 mmol) was added in one portion. After stirring for 10 min at −78° C., the mixture was slowly warmed to room temperature, and stirred for 1.5 h at room temperature. The mixture was then cooled to −78° C. again, and a solution of (2-methoxy)phenyllithium [prepared from 2-bromoanisole (3.32 g, 17.7 mmol) and 1.7 M t-BuLi solution in pentane (20.8 mL, 35.4 mmol) in $Et_2O$ (90 mL) at −78° C.] was added slowly via a cannula. The mixture was warmed to room temperature overnight, and filtered through a pad of Celite. The filtrate was concentrated, and the residue was purified by chromatography (SiO$_2$, hexane-EtOAc-Et$_3$N=85:10:5) to afford the title compound (6.50 g, 92%) as orange crystals. $^1$H NMR (CDCl$_3$, 400.13 MHz): δ 1.29 (d, 3H, J=6.5 Hz); 1.80 (s, 6H); 3.91 (s, 3H); 3.97 (s, 6H, overlap); 4.11 (m, 1H), 4.25 (t, 1H, J=2.2 Hz); 4.37 (br. s, 1H); 6.87 (m, 1H); 6.94 (dd, 1H, J=8.3 and 6.7 Hz); 7.12~7.23 (m, 6H); 7.31 (m, 1H); $^{31}$P NMR (CDCl$_3$, 162 MHz): δ–38.82. The absolute configuration of (R$_C$, S$_{Fe}$, S$_P$)-2 was determined by single-crystal X-ray diffraction analysis.

EXAMPLE 2

(R$_C$, S$_{Fe}$, S$_P$)-2-[(1-N,N-Dimethylamino)ethyl]-1-[(1-naphthyl)phenylphosphino]ferrocene [(R$_C$, S$_{Fe}$, S$_P$)-3]

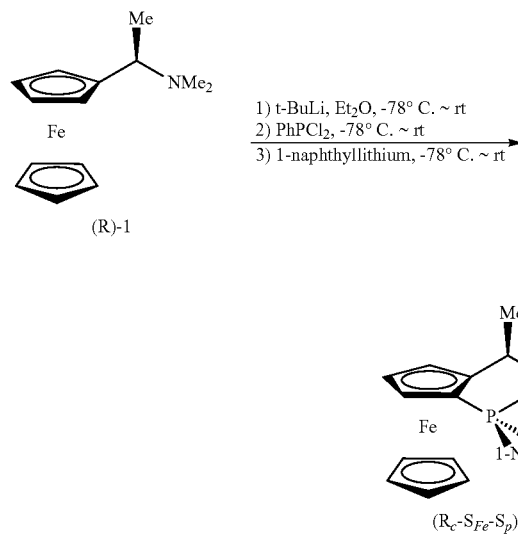

To a solution of (R)—N,N-dimethyl-1-ferrocenylethylamine [(R)-Ugi's amine, (R)-1] (5.15 g, 20 mmol) in Et$_2$O (60 mL) was added 1.7 M t-BuLi solution in pentane (12.94 mL, 22 mmol) over 10 min via a syringe at −78° C. After addition was completed, the mixture was warmed to room temperature, and stirred for 1.5 h at room temperature. The resulting red solution was cooled to −78° C. again, and dichlorophenylphosphine (2.99 mL, 22 mmol) was added in one portion. After stirring for 10 min at −78° C., the mixture was slowly warmed to room temperature, and stirred for 1.5 h at room temperature. The mixture was then cooled to −78° C. again, and a solution of 1-naphthyllithium [prepared from 1-bromonaphthalene (5.38 g, 26 mmol) and 1.7 M t-BuLi solution in pentane (30.6 mL, 52 mmol) in Et$_2$O (120 mL) at −78° C.] was added slowly via a cannula. The mixture was warmed to room temperature overnight, and filtered through a pad of Celite. The filtrate was concentrated, and the residue was purified by chromatography (SiO$_2$, hexane-EtOAc-Et$_3$N=90:6:4) to afford the title compound (8.75 g, 89%) as orange crystals. $^1$H NMR (CDCl$_3$, 400.13 MHz): δ 1.33 (d, 3H, J=6.8 Hz); 1.91 (s, 6H); 3.59 (s, 5H); 4.00 (m, 1H); 4.17 (m, 1H); 4.26 (t, 1H, J=2.2 Hz); 4.38 (m, 1H); 7.13~7.2 (m, 5H); 7.39 (t, 1H, J=6.7 Hz); 7.43~7.54 (m, 2H); 7.60~7.63 (m, 1H); 7.87 (dd, 2H, J=9.7 and 9.2 Hz), 9.33 (dd, 1H, J=7.6 and 7.0 Hz). $^{31}$P NMR (CDCl$_3$, 162 MHz): δ –38.73.

EXAMPLE 3

(R$_C$, S$_{Fe}$, S$_P$)-2-[(1-N,N-Dimethylamino)ethyl]-1-[(1-naphthyl)phenylphosphino]ferrocene [(R$_C$, S$_{Fe}$, S$_P$)-3] and (R$_C$, S$_{Fe}$, R$_P$)-2-[(1-N,N-Dimethylamino)ethyl]-1-[(1-naphthyl)phenylphosphino]ferrocene [(R$_C$, S$_{Fe}$, R$_P$)-4]

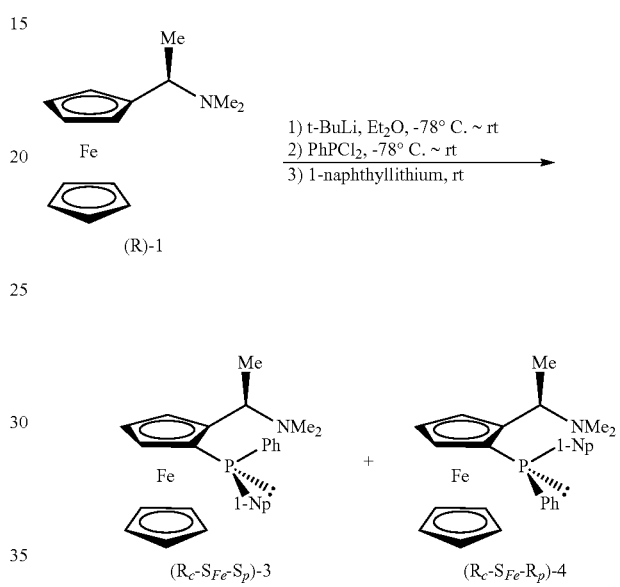

To a solution of (R)—N,N-dimethyl-1-ferrocenylethylamine [(R)-Ugi's amine, (R)-1] (1.29 g, 5 mmol) in Et$_2$O (15 mL) was added 1.7 M t-BuLi solution in pentane (3.2 mL, 5.5 mmol) over 10 min via a syringe at −78° C. After addition was completed, the mixture was warmed to room temperature, and stirred for 1.5 h at room temperature. The resulting red solution was cooled to −78° C. again, and dichlorophenylphosphine (0.75 mL, 5.5 mmol) was added in one portion. After stirring for 10 min at −78° C., the mixture was slowly warmed to room temperature, and stirred for 1.5 h at room temperature. Then to the mixture a solution of 1-naphthyllithium [prepared from 1-bromonaphthalene (1.35 g, 6.5 mmol) and 1.7 M t-BuLi solution in pentane (7.6 mL, 13 mmol) in Et$_2$O (30 mL) at −78° C.] was added via a cannula at room temperature. The mixture was stirred overnight at room temperature and filtered through a pad of Celite. The filtrate was concentrated, and the residue was purified by chromatography (SiO$_2$, hexane-EtOAc-Et$_3$N=85:10:5) to afford the title compound (2.21 g, 90%) as a mixture of two isomers. The ratio of (R$_C$, S$_{Fe}$, S$_P$)-3 to (R$_C$, S$_{Fe}$, R$_P$)-4 is about 5:1. As (R$_C$, S$_{Fe}$, R$_P$)-4 is insoluble in cold hexane and (R$_C$, S$_{Fe}$, S$_P$)-3 is very soluble in cold hexane, the two isomers can be easily separated by crystallization from hexane. (R$_C$, S$_{Fe}$, R$_P$)-4: $^1$H NMR (CDCl$_3$, 400.13 MHz): δ 1.25 (d, 3H, J=6.8 Hz); 1.60 (s,6H); 3.88 (br. s, 1H); 4.00 (s, 5H); 4.16 (m, 1H), 4.29 (t, 1H, J=2.2 Hz); 4.42 (br. s, 1H); 7.16~7.19 (m, 1H); 7.28~7.29 (m, 5H); 7.32~7.35 (m, 1H); 7.59~7.63 (m, 2H); 7.69 (d, J=8.2 Hz); 7.76 (d, J=7.6 Hz); 8.45 (m, 1H). $^{31}$P NMR (CDCl$_3$, 162 MHz): δ −31.36. The absolute configuration of (R$_C$, S$_{Fe}$, R$_P$)-4 was determined by single-crystal X-ray diffraction analysis.

EXAMPLE 4

(R$_C$, S$_{Fe}$, R$_P$)-2-[(1-N,N-Dimethylamino)ethyl]-1-[(1-naphthyl)phenylphosphino]ferrocene [(R$_C$, S$_{Fe}$, R$_P$)-4]

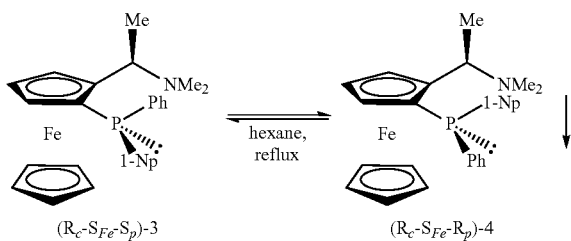

A solution of (R$_C$, S$_{Fe}$, S$_P$)-3 (491 mg, 1.0 mmol) in hexane (5 mL) was refluxed overnight. After cooling to room temperature, the precipitate was filtered and washed with cold hexane to give the pure (R$_C$, S$_{Fe}$, R$_P$)-4.

EXAMPLE 5

(R$_C$, S$_{Fe}$, S$_P$)-2-[(1-N,N-Dimethylamino)ethyl]-1-[(2-naphthyl)phenylphosphino]ferrocene [(R$_C$, S$_{Fe}$, S$_P$)-5] and (R$_C$, S$_{Fe}$, R$_P$)-2-[(1-N,N-Dimethylamino)ethyl]-14(2-naphthAphenylphosphinofferrocene [(R$_C$, SF$_e$, R$_P$)-6]

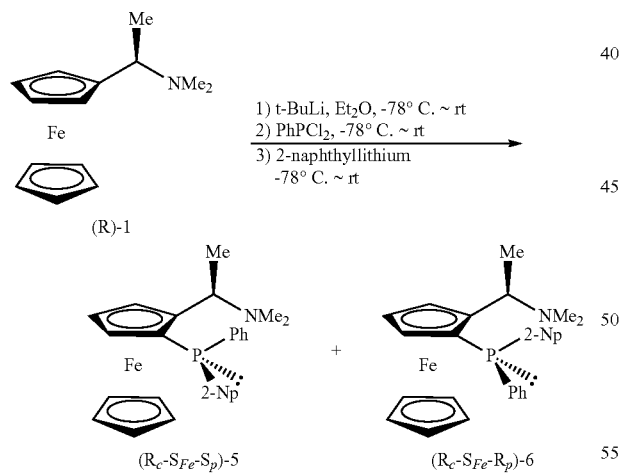

To a solution of (R)—N,N-dimethyl-1-ferrocenylethylamine [(R)-Ugi's amine, (R)-1] (2.57 g, 5 mmol) in Et$_2$O (15 mL) was added 1.7 M t-BuLi solution in pentane (6.4 mL, 11 mmol) over 10 min via a syringe at −78° C. After addition was completed, the mixture was warmed to room temperature, and stirred for 1.5 h at room temperature. The resulting red solution was cooled to −78° C. again, and dichlorophenylphosphine (1.5 mL, 11 mmol) was added in one portion. After stirring for 10 min at −78° C., the mixture was slowly warmed to room temperature, and stirred for 1.5 h at room temperature. Then the mixture was cooled to −78° C. again, and a suspension of 2-naphthyllithium [prepared from 2-bromonaphthalene (2.69 g, 13 mmol) and 1.7 M t-BuLi solution in pentane (15.2 mL, 26 mmol) in Et$_2$O (60 mL) at −78° C.] was added via a cannula at −78° C. The mixture was warmed to room temperature overnight and filtered through a pad of Celite. The filtrate was concentrated, and the residue was purified by chromatography (SiO$_2$, hexane-EtOAc-Et$_3$N=85:10:5) to afford the title compound (4.42 g, 90%) as a mixture of two isomers. The ratio of (R$_C$, S$_{Fe}$, S$_P$)-5 to (R$_C$, S$_{Fe}$, R$_P$)-6 is about 5:1. Fractional crystallization from hexane gave (R$_C$, S$_{Fe}$, S$_P$)-5 (3.10 g, 63%) and (R$_C$, S$_{Fe}$, R$_P$)-6 (687 mg, 14%). (R$_C$, S$_{Fe}$, S$_P$)-5: $^1$H NMR (CDCl$_3$, 400.13 MHz): δ 1.28 (d, 3H, J=6.2 Hz); 1.80 (s, 6H); 3.90 (br. s, 1H); 3.92 (s, 5H); 4.20 (m, 1H), 4.22 (t, 1H, J=2.2 Hz); 4.38 (br. s, 1H); 7.18~7.26 (m, 5H); 7.48 (m, 2H), 7.58 (ddd, 1H, J=8.4, 5.6 and 1.6 Hz); 7.79 (d, 1H, J=8.4 Hz); 7.83 (m, 2H); 8.18 (d, 1H, J=9.5 Hz); $^{31}$P NMR (CDCl$_3$, 162 MHz): δ −20.88. (R$_C$, S$_{Fe}$, R$_P$)-6: $^1$H NMR (CDCl$_3$, 400.13 MHz): δ 1.27 (d, 3H, J=5.7 Hz); 1.76 (s, 6H); 3.90 (br. s, 1H); 3.96 (s, 5H); 4.18 (m, 1H), 4.29 (t, 1H, J=2.2 Hz); 4.41 (br. s, 1H); 7.29 (ddd, 1H, J=8.3, 7.0 and 1.6 Hz); 7.34 (m, 3H); 7.39 (m, 2H); 7.59~7.67 (m, 5H); 7.74 (m, 1H); $^{31}$P NMR (CDCl$_3$, 162 MHz): δ −20.57.

EXAMPLE 6

(R$_C$, S$_{Fe}$, S$_P$)-2-[(1-N,N-Dimethylamino)ethyl]-1-[(2-naphthyl)phenylphosphino]ferrocene [(R$_C$, S$_{Fe}$, S$_P$)-5]

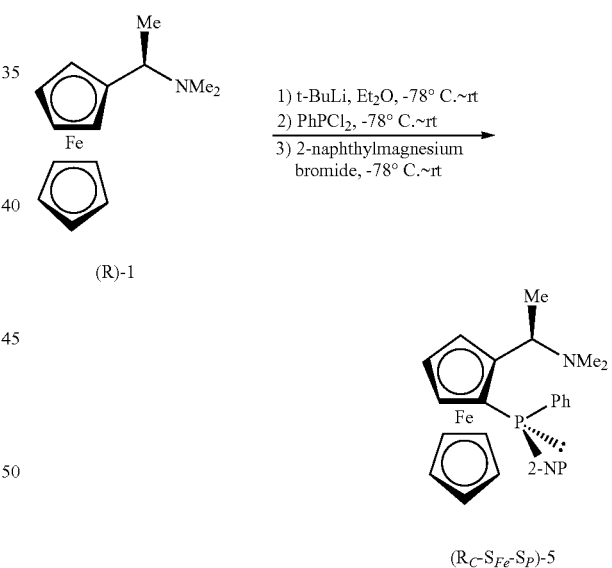

To a solution of (R)—N,N-dimethyl-1-ferrocenylethylamine [(R)-Ugi's amine, (R)-1] (2.06 g, 8 mmol) in Et$_2$O (15 mL) was added 1.5 M t-BuLi solution in pentane (6.0 mL, 9 mmol) over 10 min via a syringe at −78° C. After addition was completed, the mixture was warmed to room temperature, and stirred for 1.5 h at room temperature. The resulting red solution was cooled to −78° C. again, and dichlorophenylphosphine (1.22 mL, 9 mmol) was added in one portion. After stirring for 10 min at −78° C., the mixture was slowly warmed to room temperature, and stirred for 1.5 h at room temperature. Then the mixture was cooled to −78° C. again, and a solution of 2-naphthylmagnesium bromide [prepared from 2-bromonaphthalene (2.20 g, 10.6 mmol) and magnesium (258 mg, 10.6 mmol) in Et$_2$O (20 mL)] was added via a cannula at −78° C. The mixture was warmed to room temperature overnight. The reaction was quenched with saturated NH$_4$Cl solution (20 mL). The organic layer was separated, and the aqueous layer was extracted with Et$_2$O (20 mL). The combined organic layers were washed with brine (20 mL), dried (MgSO$_4$), and concentrated. The residue was purified by chromatography (SiO$_2$, hexane-EtOAc-Et$_3$N=85:10:5) to afford the title compound (3.42 g, 87%) as single diastereomer. $^1$H NMR (CDCl$_3$, 400.13 MHz): δ 1.28 (d, 3H, J=6.2 Hz); 1.80 (s, 6H); 3.90 (br. s, 1H); 3.92 (s, 5H); 4.20 (m, 1H); 4.22 (t, 1H, J=2.2 Hz); 4.38 (br. s, 1H); 7.18~7.26 (m, 5H); 7.48 (m, 2H); 7.58 (ddd, 1H, J=8.4, 5.6 and 1.6 Hz); 7.79 (d, 1H, J=8.4 Hz); 7.83 (m, 2H); 8.18 (d, 1H, J=9.5 Hz); $^{31}$P NMR (CDCl$_3$, 162 MHz): δ −20.88.

EXAMPLE 7

($R_C$, $S_{Fe}$, $S_P$)-2-[(1-N,N-Dimethylamino)ethyl]-1-[(2-biphenyl)phenylphosphino]ferrocene [($R_C$, $S_{Fe}$, $S_P$)-7]

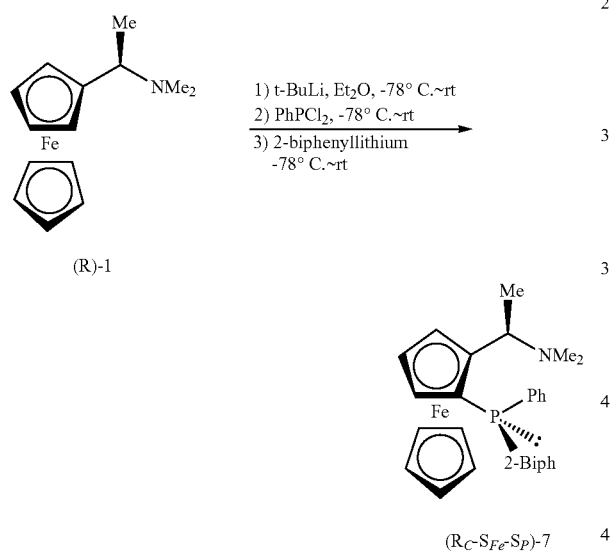

To a solution of (R)—N,N-dimethyl-1-ferrocenylethylamine [(R)-Ugi's amine, (R)-1] (2.57 g, 10 mmol) in Et$_2$O (20 mL) was added 1.5 M t-BuLi solution in pentane (7.33 mL, 11 mmol) over 10 min via a syringe at −78° C. After addition was completed, the mixture was warmed to room temperature, and stirred for 1.5 h at room temperature. The resulting red solution was cooled to −78° C. again, and dichlorophenylphosphine (1.50 mL, 11 mmol) was added in one portion. After stirring for 10 min at −78° C., the mixture was slowly warmed to room temperature, and stirred for 1.5 h at room temperature. Then the mixture was cooled to −78° C. again, and a suspension of 2-biphenyllithium [prepared from 2-bromobiphenyl (2.24 mL, 13 mmol) and 1.5 M t-BuLi solution in pentane (17.3 mL, 26 mmol) in Et$_2$O (30 mL) at −78° C.] was added via a cannula at −78° C. The mixture was warmed to room temperature overnight and filtered through a pad of Celite. The filtrate was concentrated, and the residue was purified by chromatography (SiO$_2$, hexane-EtOAc-Et$_3$N=85:10:5) to afford the title compound (4.87 g, 94%) as single diastereomer. $^1$H NMR (CDCl$_3$, 400.13 MHz): δ 1.25 (d, 3H, J=6.7 Hz); 1.85 (s, 6H); 3.69 (s, 5H); 3.76 (m, 1H), 4.17 (m, 1H), 4.29 (t, 1H, J=2.4 Hz); 4.32 (m, 1H); 7.10~7.19 (m, 5H); 7.31 (m, 1H), 7.37~7.48 (m, 5H), 7.64 (m, 1H); 7.69 (m, 1H); 7.71 (m, 1H). $^{31}$P NMR (CDCl$_3$, 162 MHz): δ −32.96

EXAMPLE 8

($R_C$, $S_{Fe}$, $S_P$)-2-[(1-N,N-Dimethylamino)ethyl]-1-(methyl phenylphosphino)ferrocene [($R_C$, $S_{Fe}$, $R_P$)-8]

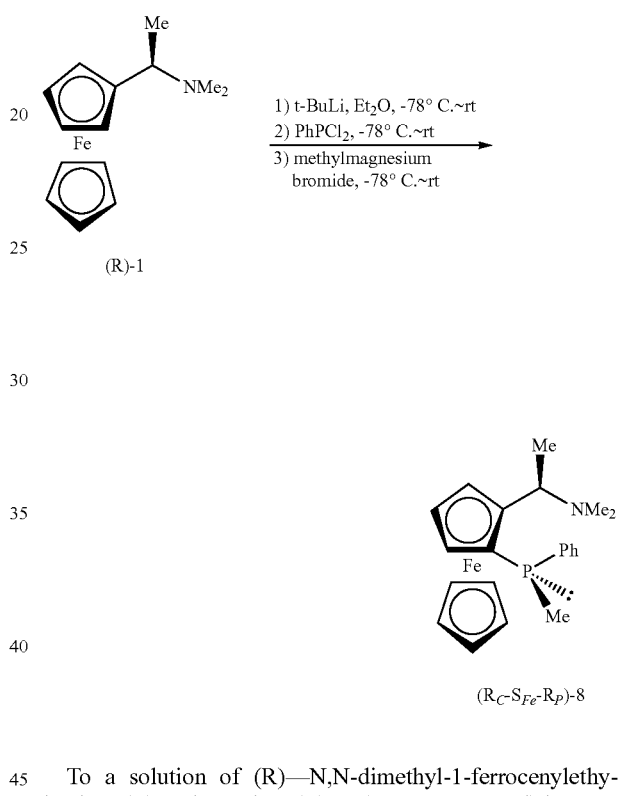

To a solution of (R)—N,N-dimethyl-1-ferrocenylethylamine [(R)-Ugi's amine, (R)-1] (2.57 g, 10 mmol) in Et$_2$O (20 mL) was added 1.5 M t-BuLi solution in pentane (7.33 mL, 11 mmol) over 10 min via a syringe at −78° C. After addition was completed, the mixture was warmed to room temperature, and stirred for 1.5 h at room temperature. The resulting red solution was cooled to −78° C. again, and dichlorophenylphosphine (1.50 mL, 11 mmol) was added in one portion. After stirring for 10 min at −78° C., the mixture was slowly warmed to room temperature, and stirred for 1.5 h at room temperature. Then the mixture was cooled to −78° C. again, and 3.0 M solution of MeMgBr in Et$_2$O (4.0 mL, 12 mmol) was added via a syringe at −78° C. The mixture was warmed to room temperature overnight. The reaction was quenched with saturated NH$_4$Cl solution (20 mL). The organic layer was separated, and the aqueous layer was extracted with Et$_2$O (20 mL). The combined organic layers were washed with brine (20 mL), dried (MgSO$_4$), and concentrated. The residue was purified by chromatography (SiO$_2$, hexane-EtOAc-Et$_3$N=85:10:5) to afford the title compound (3.36 g, 89%) as red oil. $^1$H NMR (CDCl$_3$, 400.13 MHz): δ 1.24 (d, 3H, J=6.7 Hz); 1.56 (d, 3H, J=4.4 Hz); 1.72

(s, 6H); 4.07 (m, 1H), 4.13 (s, 5H); 4.30 (m, 1H), 4.34 (m, 2H); 7.14~7.20 (m, 3H); 7.30~7.37 (m, 2H). $^{31}$P NMR (CDCl$_3$, 162 MHz): δ −43.47

EXAMPLE 9

($R_C$, $S_{Fe}$, $S_P$)-2-[(1-N,N-Dimethylamino)ethyl]-1-(cyclohexylphenylphosphino)ferrocene [($R_C$, $S_{Fe}$, $R_P$)-9]

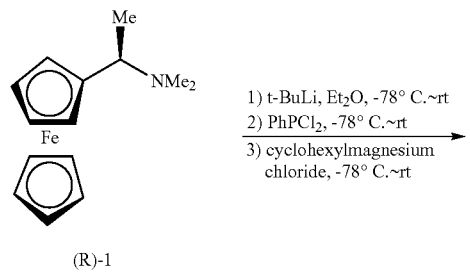

(R)-1

1) t-BuLi, Et$_2$O, -78° C.~rt
2) PhPCl$_2$, -78° C.~rt
3) cyclohexylmagnesium chloride, -78° C.~rt

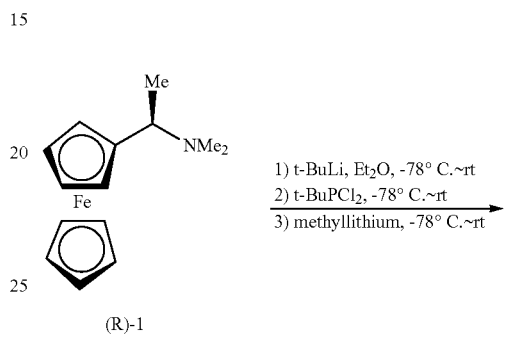

($R_C$-$S_{Fe}$-$R_P$)-9

To a solution of (R)-N,N-dimethyl-1-ferrocenylethylamine [(R)-Ugi's amine, (R)-1] (2.57 g, 10 mmol) in Et$_2$O (20 mL) was added 1.5 M t-BuLi solution in pentane (7.35 mL, 11 mmol) over 10 min via a syringe at −78° C. After addition was completed, the mixture was warmed to room temperature, and stirred for 1.5 h at room temperature. The resulting red solution was cooled to −78° C. again, and dichlorophenylphosphine (1.50 mL, 11 mmol) was added in one portion. After stirring for 10 min at −78° C., the mixture was slowly warmed to room temperature, and stirred for 1.5 h at room temperature. Then the mixture was cooled to −78° C. again, and 2.0 M solution of cyclohexymagnesium chloride in Et$_2$O (6.0 mL, 12 mmol) was added via a syringe at −78° C. The mixture was warmed to room temperature overnight. The reaction was quenched with saturated NH$_4$Cl solution (20 mL). The organic layer was separated, and the aqueous layer was extracted with Et$_2$O (20 mL). The combined organic layers were washed with brine (20 mL), dried (MgSO$_4$), and concentrated. The residue was purified by chromatography (SiO$_2$, hexane-EtOAc-Et$_3$N=90:5:5) to afford the title compound (4.09 g, 92%) as red oil. $^1$H NMR (CDCl$_3$, 400.13 MHz): δ 1.16 (d, 3H, J=6.7 Hz); 1.19~2.03 (m, 11H); 1.50 (s, 6H); 3.99 (m, 1H), 4.11 (s, 5H); 4.30 (m, 1H), 4.32 (t, 1H, J=2.5 Hz); 4.37 (m, 1H), 7.12~7.150 (m, 3H); 7.18~7.23 (m, 2H). $^{31}$P NMR (CDCl$_3$, 162 MHz): δ −14.86

EXAMPLE 10

($R_C$, $S_{Fe}$, $S_P$)-2-[(1-N,N-Dimethylamino)ethyl]-1-(methyl(tert-butyl)phenylphosphino)ferrocene [($R_C$, $S_{Fe}$, $R_P$)-10]

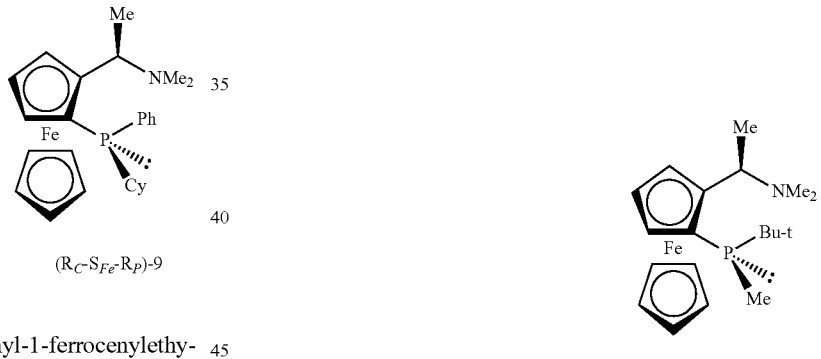

To a solution of (R)—N,N-dimethyl-1-ferrocenylethylamine [(R)-Ugi's amine, (R)-1] (1.29 g, 5 mmol) in Et$_2$O (15 mL) was added 1.5 M t-BuLi solution in pentane (3.7 mL, 5.5 mmol) over 10 min via a syringe at −78° C. After addition was completed, the mixture was warmed to room temperature, and stirred for 1.5 h at room temperature. The resulting red solution was cooled to −78° C. again, and tert-butyldichlorophosphine (875 mg, 5.5 mmol) was added in one portion. After stirring for 10 min at −78° C., the mixture was slowly warmed to room temperature, and stirred for 1.5 h at room temperature. Then to the mixture a 1.6 M solution of methyllithium in Et$_2$O (3.75 mL, 6.0 mmol) was added via a syringe at −78° C. The mixture was warmed to room temperature overnight and filtered through a pad of Celite. The filtrate was concentrated, and the residue was purified by chromatography (SiO$_2$, hexane-EtOAc-Et$_3$N=90:5:5) to afford the title compound (1.54 g, 86%) as red oil. $^1$H NMR (CDCl$_3$, 250.13 MHz): δ 1.09 (d, 9H, J=12.0 Hz), 1.27 (d, 3H, J=6.7 Hz); 1.45 (d, 3H, J=3.3 Hz); 2.08 (s, 6H); 3.92 (m, 1H), 4.10 (s, 5H); 4.28 (m, 3H). $^{31}$P NMR (CDCl$_3$, 101 MHz): δ −6.47

EXAMPLE 11

($R_C$, $S_{Fe}$, $S_P$)-2-(1-Acetoxyethyl)-1-[(2-methoxyphenyl)phenylphosphino]ferrocene [($R_C$, $S_{Fe}$, $S_P$)-11]

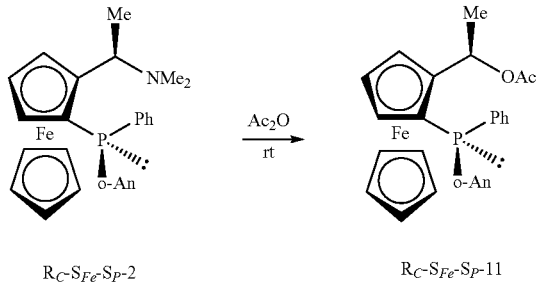

A solution of ($R_C$, $S_{Fe}$, $S_P$)-2 (1.18 g, 2.5 mmol) in acetic anhydride (10 mL) was stirred for 60 h at room temperature. The excess acetic anhydride was removed under reduced pressure (<1 Torr, <30° C.) to give the title compound (1.21 g, 100%) as yellow solid, which is pure enough for the use in the next reaction. $^1$H NMR (CDCl$_3$, 400.13 MHz): δ 1.19 (s, 3H); 1.64 (d, 3H, J=6.5 Hz); 3.90 (s, 3H); 3.92 (m, 1H); 4.07 (s, 5H); 4.34 (t, 1H, J=2.6 Hz); 5.55 (m, 1H); 6.15 (m, 1H); 6.87 (td, 1H, J=7.4 and 0.9 Hz); 6.95 (q, 1H, J=4.8 Hz); 7.08~7.21 (m, 6H); 7.35 (m, 1H); $^{31}$P NMR (CDCl$_3$, 162 MHz): δ −39.30.

EXAMPLE 12

($R_C$, $S_{Fe}$, $S_P$)-2-(1-Acetoxyethyl)-1-[(1-naphthyl)phenylphosphino]ferrocene [($R_C$, $S_{Fe}$, $S_P$)-12]

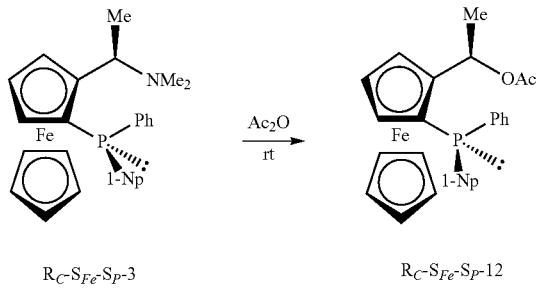

A solution of ($R_C$, $S_{Fe}$, $S_P$)-3 (1.47 g, 3.0 mmol) in acetic anhydride (20 mL) was stirred for 60 h at room temperature. The excess acetic anhydride was removed under reduced pressure (<1 Torr, <30° C.) to give the title compound (1.52 g, 100%) as yellow solid, which is pure enough for the use in the next reaction. $^1$H NMR (CDCl$_3$, 400.13 MHz): δ 1.29 (s, 3H); 1.67 (d, 3H, J=6.5 Hz); 3.72 (s, 5H); 3.94 (m, 1H); 4.35 (t, 1H, J=2.6 Hz); 4.57 (m, 1H); 6.28 (m, 1H); 7.13~7.22 (m, 5H); 7.38~7.43 (m, 2H), 7.53 (ddd, 1H, J=8.0, 6.7 and 1.1 Hz), 7.64 (ddd, 1H, J=8.4, 6.8 and 1.4 Hz), 7.89 (t, 2H, J=7.0 Hz); 9.28 (t, 1H, J=7.0 Hz); $^{31}$P NMR (CDCl$_3$, 162 MHz): δ −39.81.

EXAMPLE 13

($R_C$, $S_{Fe}$, $R_P$)-2-(1-Acetoxyethyl)-1-[(1-naphthyl)phenylphosphino]ferrocene [($R_C$, $S_{Fe}$, $R_P$)-13]

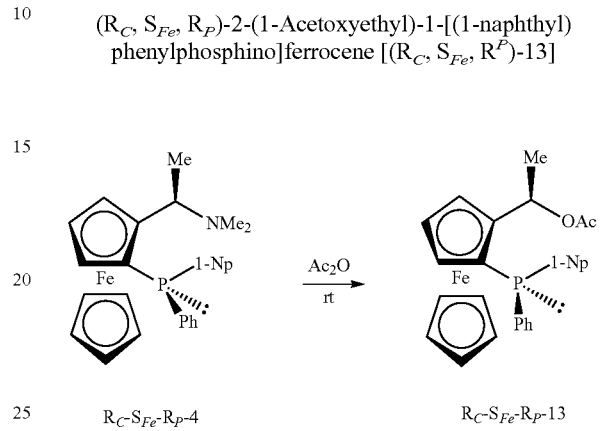

A solution of ($R_C$, $S_{Fe}$, $R_P$)-4 (1.47 g, 3.0 mmol) in acetic anhydride (20 mL) was stirred for 60 h at room temperature. The excess acetic anhydride was removed under reduced pressure (<1 Torr, <30° C.) to give the title compound (1.52 g, 100%) as yellow solid, which is pure enough for the use in the next reaction. $^1$H NMR (CDCl$_3$, 400.13 MHz): δ 0.83 (s, 3H); 1.62 (d, 3H, J=6.5 Hz); 3.83 (m, 1H); 4.10 (s, 5H); 4.40 (t, 1H, J=2.6 Hz); 5.61 (m, 1H); 6.21 (m, 1H); 7.11 (ddd, 1H, J=7.0, 4.6 and 1.1 Hz); 7.28~7.41 (m, 6H); 7.55~7.43 (m, 2H), 7.75 (m, 2H), 8.29 (m, 1H); $^{31}$P NMR (CDCl$_3$, 162 MHz): δ −31.33.

EXAMPLE 14

($R_C$, $S_{Fe}$, $S_P$)-2-(1-Acetoxyethyl)-1-[(2-naphthyl)phenylphosphino]ferrocene [($R_C$, $S_{Fe}$, $S_P$)-14]

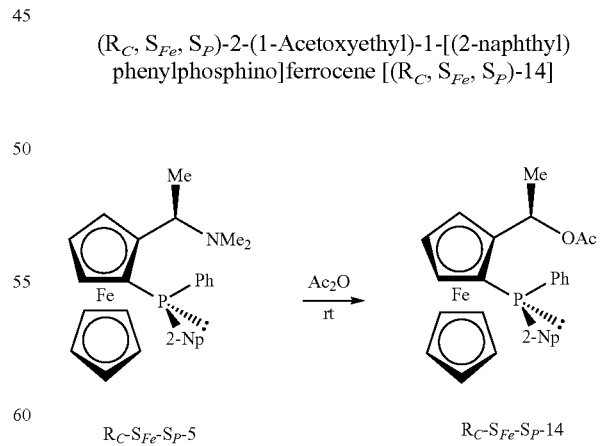

A solution of ($R_C$, $S_{Fe}$, $S_P$)-5 (1.47 g, 3.0 mmol) in acetic anhydride (20 mL) was stirred for 60 h at room temperature. The excess acetic anhydride was removed under reduced pressure (<1 Torr, <30° C.) to give the title compound (1.52 g, 100%) as yellow solid, which is pure enough for the use in the next reaction. $^1$H NMR (CDCl$_3$, 400.13 MHz): δ 1.21 (s, 3H); 1.65 (d, 3H, J=6.5 Hz); 3.83 (m, 1H); 4.03 (s, 5H); 4.33 (t, 1H, J=2.6 Hz); 4.57 (m, 1H); 6.24 (m, 1H); 7.19~7.27 (m, 5H); 7.46~7.51 (m, 3H), 7.81 (m, 3H), 8.11 (d, 1H, J=10.4 Hz); $^{31}$P NMR (CDCl$_3$, 162 MHz): δ −22.89.

EXAMPLE 15

($R_C$, $S_{Fe}$, $R_P$)-2(1-Acetoxyethyl)-1-[(2-naphthyl)phenylphOSphinO]ferrOCene [($R_C$, $S_{Fe}$, $R_P$)-15]

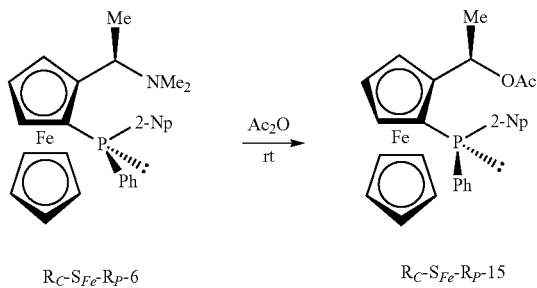

A solution of ($R_C$, $S_{Fe}$, $R_P$)-6 (1.47 g, 3.0 mmol) in acetic anhydride (20 mL) was stirred for 60 h at room temperature. The excess acetic anhydride was removed under reduced pressure (<1 Torr, <30° C.) to give the title compound (1.52 g, 100%) as yellow solid, which is pure enough for the use in the next reaction. $^1$H NMR (CDCl$_3$, 400.13 MHz): δ 0.92 (s, 3H); 1.64 (d, 3H, J=6.4 Hz); 3.87 (m, 1H); 4.07 (s, 5H); 4.40 (t, 1H, J=2.6 Hz); 5.61 (m, 1H); 6.23 (m, 1H); 7.27 (ddd, 1H, J=8.2, 6.8 and 1.4 Hz), 7.32~7.38 (m, 3H); 7.39~7.44 (m, 2H), 7.53~7.57 (m, 2H), 7.60 (d, 1H, J=8.0 Hz), 7.69 (m, 2H), 7.74 (m, 1H); $^{31}$P NMR (CDCl$_3$, 162 MHz): δ −22.58.

EXAMPLE 16

($R_C$, $S_{Fe}$, $S_P$)-2-(1-Acetoxyethyl)-1-[(2-biphenyl)phenylphosphino]ferrocene [($R_C$, $S_{Fe}$, $S_P$)-16]

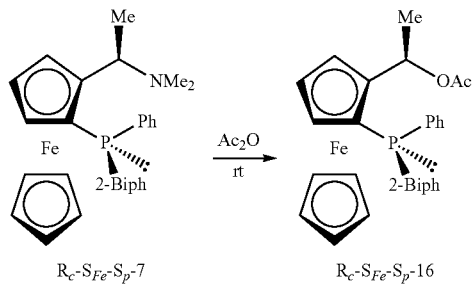

A solution of ($R_C$, $S_{Fe}$, $S_P$)-7 (1.47 g, 3.0 mmol) in acetic anhydride (20 mL) was stirred for 60 h at room temperature. The excess acetic anhydride was removed under reduced pressure (<1 Torr, <30° C.) to give the title compound (1.52 g, 100%) as yellow solid, which is pure enough for the use in the next reaction. $^1$H NMR (CDCl$_3$, 400.13 MHz): δ 1.25 (s, 3H); 1.52 (d, 3H, J=6.5 Hz); 3.73 (s, 5H); 3.96 (m, 1H); 4.33 (t, 1H, J=2.6 Hz); 4.48 (m, 1H); 5.81 (m, 1H); 7.16~7.27 (m, 6H); 7.38~7.51 (m, 6H), 7.70~7.73 (m, 2H). $^{31}$P NMR (CDCl$_3$, 162 MHz): δ −35.03.

EXAMPLE 17

($R_C$, $S_{Fe}$, $S_P$)-2-[(1-N-Methylamino)ethyl]-1-[(2-methoxyphenyl)phenylphosphino]ferrocene [($R_C$, $S_{Fe}$, $S_P$)-17]

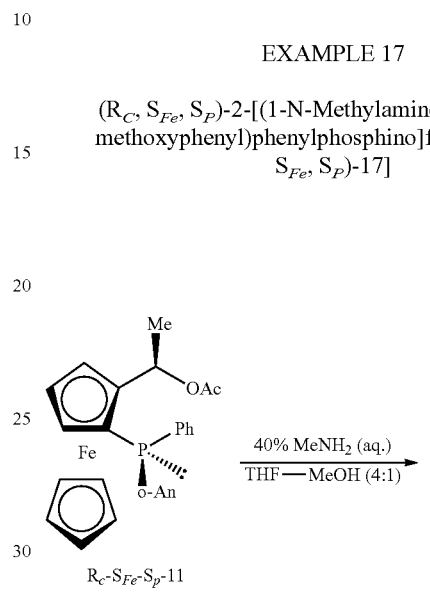

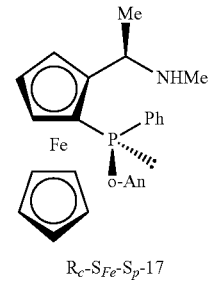

A solution of ($R_C$, $S_{Fe}$, $S_P$)-11 (1.21 g, 2.5 mmol) and 40% methylamine aqueous solution (6.0 mL) in THF (20 mL) and MeOH (5 mL) was stirred for 3 days at 40° C., and concentrated. The residue was dissolved in Et$_2$O (20 mL), washed with brine (10 mL), dried (Na$_2$SO$_4$), and evaporated under reduced pressure. The crude product was purified by chromatography (SiO$_2$, hexane-EtOAc-Et$_3$N=80:15:5) to give the title compound (1.07 g, 94%) as orange crystals. $^1$H NMR (CDCl$_3$, 250.13 MHz): δ 1.44 (d, 3H, J=6.5 Hz); 1.94 (s, 3H); 3.91 (m, 2H); 3.95 (s, 3H); 4.05 (s, 5H); 4.29 (t, 1H, J=2.5 Hz); 4.46 (m, 1H); 7.90 (dt, 1H, J=7.3 and 1.0 Hz), 6.97 (ddd, 1H, J=8.3, 5.0 and 1.0 Hz), 7.15 (ddd, 1H, J=7.3, 5.5 and 1.8 Hz), 7.23 (m, 5H); 7.36 (ddd, 1H, J=8.3, 7.3 and 1.8 Hz), $^{31}$P NMR (CDCl$_3$, 101 MHz): δ −41.43.

EXAMPLE 18

($R_C$, $S_{Fe}$, $S_P$)-2-[(1-N-Methylamino)ethyl]-1-[(1-naphthyl)phenylphosphino]ferrocene [($R_C$, $S_{Fe}$, $S_P$)-18]

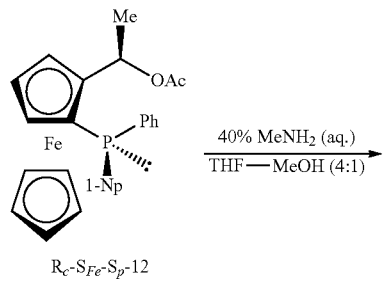

$R_c$-$S_{Fe}$-$S_p$-12

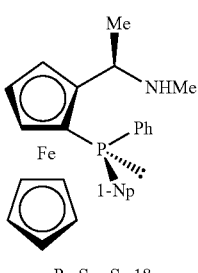

$R_c$-$S_{Fe}$-$S_p$-18

A solution of ($R_C$, $S_{Fe}$, $S_P$)-12 (633 mg, 1.25 mmol) and 40% methylamine aqueous solution (3.0 mL) in THF (10 mL) and MeOH (2.5 mL) was stirred for 3 days at 40° C., and concentrated. The residue was dissolved in $Et_2O$ (20 mL), washed with brine (10 mL), dried ($Na_2SO_4$), and evaporated under reduced pressure. The crude product was purified by chromatography ($SiO_2$, hexane-EtOAc-$Et_3$N=85:10:5) to give the title compound (549 mg, 92%) as orange crystals. $^1$H NMR ($CDCl_3$, 400.13 MHz): δ 1.49 (d, 3H, J=6.6 Hz); 2.07 (s, 3H); 3.69 (s, 5H); 3.95 (m, 1H); 4.01 (m, 1H); 4.31 (t, 1H, J=2.5 Hz); 4.48 (m, 1H); 7.23 (m, 5H); 7.39~7.47 (m, 2H); 7.54 (m, 1H); 7.66 (m, 1H); 7.90 (t, 2H, J=7.9 Hz), 9.25 (dd, 1H, J=7.9 and 6.7 Hz). $^{31}$P NMR ($CDCl_3$, 162 MHz): δ −39.91.

EXAMPLE 19

($R_C$, $S_{Fe}$, $R_P$)-2-[(1-N-Methylamino)ethyl]-1-[(1-naphthyl)phenylphosphino]ferrocene [($R_C$, $S_{Fe}$, $R_P$)-19]

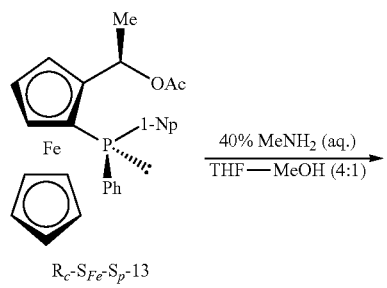

$R_c$-$S_{Fe}$-$S_p$-13

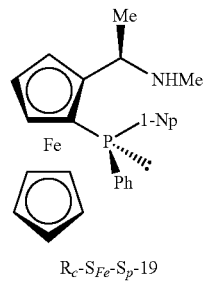

$R_c$-$S_{Fe}$-$S_p$-19

A solution of ($R_C$, $S_{Fe}$, $R_P$)-7 (633 mg, 1.25 mmol) and 40% methylamine aqueous solution (3.0 mL) in THF (10 mL) and MeOH (2.5 mL) was stirred for 3 days at 40° C., and concentrated. The residue was dissolved in $Et_2O$ (20 mL), washed with brine (10 mL), dried ($Na_2SO_4$), and evaporated under reduced pressure. The crude product was purified by chromatography ($SiO_2$, hexane-EtOAc-$Et_3$N=85:10:5) to give the title compound (537 mg, 90%) as orange crystals. $^1$H NMR ($CDCl_3$, 400.13 MHz): δ 1.45 (d, 3H, J=6.5 Hz); 1.83 (s, 3H); 3.82 (m, 1H); 3.97 (m, 1H); 4.07 (s, 5H); δ 4.35 (t, 1H, J=2.5 Hz); 4.53 (m, 1H); 7.20 (m, 1H); 7.30~7.36 (m, 5H); 7.40 (m, 1H); 7.56~7.61 (m, 2H); 7.78 (t, 2H, J=8.2 Hz), 8.38 (m, 1H). $^{31}$P NMR ($CDCl_3$, 162 MHz): δ −32.25.

EXAMPLE 20

($R_C$, $S_{Fe}$, $S_P$)-2-[(1-N-Methylamino)ethyl]-1-[(2-naphthyl)phenylphosphino]ferrocene [($R_C$, $S_{Fe}$, $S_P$)-20]

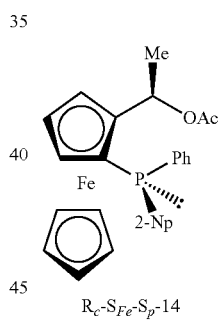

$R_c$-$S_{Fe}$-$S_p$-14

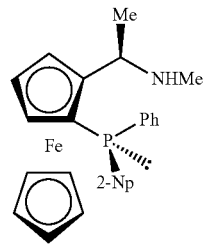

$R_c$-$S_{Fe}$-$S_p$-20

A solution of ($R_C$, $S_{Fe}$, $S_P$)-14 (633 mg, 1.25 mmol) and 40% methylamine aqueous solution (3.0 mL) in THF (10 mL) and MeOH (2.5 mL) was stirred for 3 days at 40° C., and concentrated. The residue was dissolved in $Et_2O$ (20 mL), washed with brine (10 mL), dried ($Na_2SO_4$), and evaporated under reduced pressure. The crude product was purified by chromatography ($SiO_2$, hexane-EtOAc-$Et_3$N=85:10:5) to give the title compound (513 mg, 86%) as orange crystals. $^1$H NMR ($CDCl_3$, 400.13 MHz): δ 1.47 (d, 3H, J=6.7 Hz); 1.98

(s, 3H); 3.82 (m, 1H); 3.98 (m, 1H); 4.02 (s, 5H); 4.27 (t, 1H, J=2.5 Hz); 4.47 (m, 1H); 7.27~7.34 (m, 5H); 7.50 (m, 2H); 7.55 (m, 1H); 7.83 (m, 3H); 8.12 (d, 1H, J=10.0 Hz). $^{31}$P NMR (CDCl$_3$, 162 MHz): δ −22.68.

EXAMPLE 21

($R_C$, $S_{Fe}$, $R_P$)-2-[(1-N-Methylamino)ethyl]-1-[(2-naphthyl)phenylphosphino]ferrocene [($R_C$, $S_{Fe}$, $R_P$)-21]

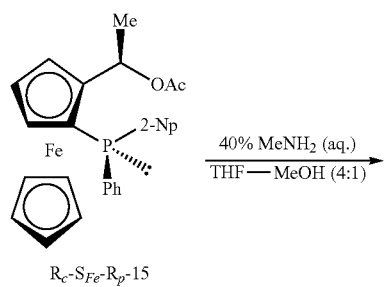

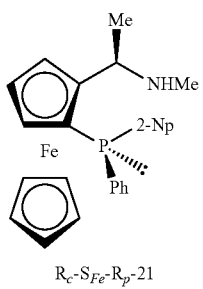

A solution of ($R_C$, $S_{Fe}$, $R_P$)-15 (633 mg, 1.25 mmol) and 40% methylamine aqueous solution (3.0 mL) in THF (10 mL) and MeOH (2.5 mL) was stirred for 3 days at room temperature, and concentrated. The residue was dissolved in Et$_2$O (20 mL), washed with brine (10 mL), dried (Na$_2$SO$_4$), and evaporated under reduced pressure. The crude product was purified by chromatography (SiO$_2$, hexane-EtOAc-Et$_3$N=85:10:5) to give the title compound (537 mg, 90%) as orange crystals.

EXAMPLE 22

($R_C$, $S_{Fe}$, $S_P$)-2-[(1-N-Methylamino)ethyl]-1-[(2-biphenyl)phenylphosphino]ferrocene [($R_C$, $S_{Fe}$, $S_P$)-22]

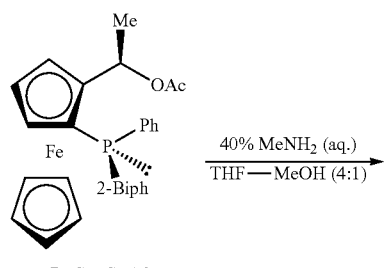

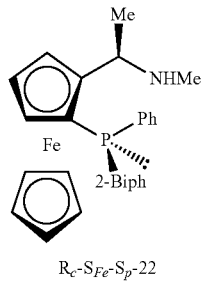

A solution of ($R_C$, $S_{Fe}$, $S_P$)-16 (1.063 g, 2 mmol) and 40% methylamine aqueous solution (5.0 mL) in THF (10 mL) and MeOH (2.5 mL) was stirred for 2 days at 40° C., and concentrated. The residue was dissolved in Et$_2$O (20 mL), washed with brine (10 mL), dried (Na$_2$SO$_4$), and evaporated under reduced pressure. The residue was recrystallized from hexane to give the title compound (621 mg, 62%) as orange crystals. $^1$H NMR (CDCl$_3$, 400.13 MHz): δ 1.34 (d, 3H, J=6.6 Hz); 1.93 (s, 3H); 3.60 (m, 1H); 3.74 (s, 5H); 4.08 (m, 1H); 4.30 (t, 1H, J=2.5 Hz); 4.39 (m, 1H); 7.19~7.24 (m, 5H); 7.31 (m, 1H); 7.38~7.50 (m, 5H), 7.59 (ddt, 1H, J=7.6, 3.5 and 1.0 Hz); 7.67 (m, 2H). $^{31}$P NMR (CDCl$_3$, 162 MHz): δ −34.29.

EXAMPLE 23

($R_C$, $S_{Fe}$, $S_P$)-2-[(1-[(N-Methyl-N-diphenylphosphino)amino]ethyl]-1-[(2-methoxyphenyl)phenylphosphino]ferrocene [($R_C$, $S_{Fe}$, $S_P$)-23]

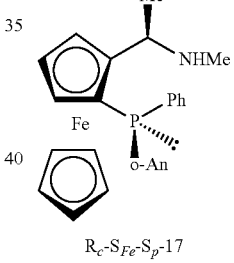 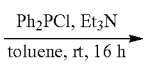

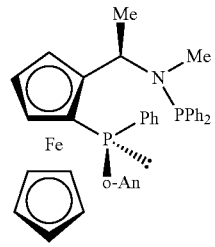

To a solution of ($R_C$, $S_{Fe}$, $S_P$)-17 (457 mg, 1.0 mmol) and Et$_3$N (0.28 mL, 2.0 mmol) in toluene (2.5 mL) was added dropwise chlorodiphenylphosphine (188 uL, 1.05 mmol) at 0° C. Then the mixture was warmed to room temperature, and stirred overnight (16 h) at room temperature, and filtered through a pad of neutral aluminium oxide and eluted with hexane-EtOAc (9:1) to afford the title compound (570 mg, 89%) as orange foam. $^1$H NMR (CDCl$_3$, 400.13 MHz): δ 1.55 (d, 3H, J=6.9 Hz); 2.17 (d, 3H, J=3.4 Hz); 3.87 (s, 8H, overlap); 4.24 (m, 1H); 4.38 (t, 1H, J=2.4 Hz); 4.53 (m, 1H); 4.88 (m, 1H); 6.88~6.96 (m, 6H); 7.03~7.14 (m, 6H); 7.20~7.37 (m, 7H). $^{31}$P NMR (CDCl$_3$, 162 MHz): δ 56.93, −38.64.

EXAMPLE 24

($R_C$, $S_{Fe}$, $S_P$)-2-[1-[(N-Methyl-N-diphenylphosphino)amino]ethyl]-1-[(1-naphthyl)phenylphosphino]ferrocene [($R_C$, $S_{Fe}$, $S_P$)-24]

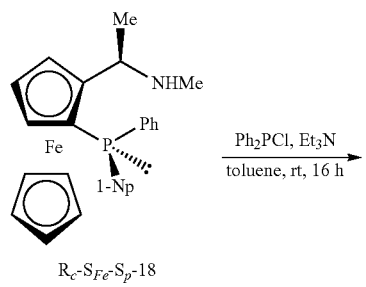

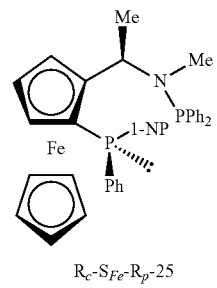

$R_c$-$S_{Fe}$-$R_p$-25

To a solution of ($R_C$, $S_{Fe}$, $R_P$)-19 (239 mg, 0.5 mmol) and Et$_3$N (0.14 mL, 1.0 mmol) in toluene (2.0 mL) was added dropwise chlorodiphenylphosphine (89 uL, 0.50 mmol) at 0° C. Then the mixture was warmed to room temperature, and stirred overnight (16 h) at room temperature, and filtered through a pad of neutral aluminium oxide and eluted with hexane-EtOAc (9:1) to afford the title compound (304 mg, 92%) as orange foam. $^1$H NMR (CDCl$_3$, 400.13 MHz): δ 1.51 (d, 3H, J=6.8 Hz); 2.08 (d, 3H, J=3.5 Hz); 3.90 (s, 5H); 4.15 (m, 1H); 4.44 (t, 1H, J=2.4 Hz); 4.58 (m, 1H); 5.02 (m, 1H); 6.44 (td, 2H, J=8.0 and 1.8 Hz); 6.62 (td, 2H, J=8.0 and 1.2 Hz); 6.80 (tt, 1H, J=7.4 and 1.2 Hz); 7.20 (m, 1H); 7.15~7.30 (m, H); 7.58~7.64 (m, H); 7.70 (dd, 1H, J=6.8 and 1.8 Hz); 7.79 (d, 1H, J=8.0 Hz); 8.20 (dd, 1H, J=8.2 and 2.4 Hz). $^{31}$P NMR (CDCl$_3$, 162 MHz): δ 58.81, −31.16.

EXAMPLE 26

($R_C$, $S_{Fe}$, $S_P$)-2-[1-[(N-Methyl-N-diphenylphosphino)amino]ethyl]-1-[(2-biphenyl)phenylphosphino]ferrocene [($R_C$, $S_{Fe}$, $S_P$)-26]

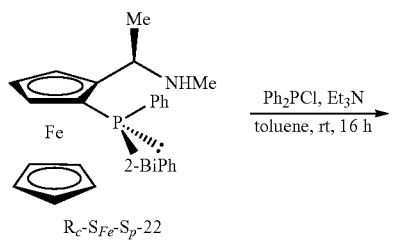

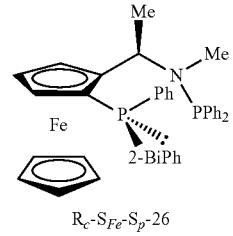

$R_c$-$S_{Fe}$-$S_p$-26

To a solution of ($R_C$, $S_{Fe}$, $S_P$)-18 (477 mg, 1.0 mmol) and Et$_3$N (0.28 mL, 2.0 mmol) in toluene (2.5 mL) was added dropwise chlorodiphenylphosphine (188 uL, 1.05 mmol) at 0° C. Then the mixture was warmed to room temperature, and stirred overnight (16 h) at room temperature, and filtered through a pad of neutral aluminium oxide and eluted with hexane-EtOAc (9:1) to afford the title compound (595 mg, 90%) as orange foam. $^1$H NMR (CDCl$_3$, 400.13 MHz): δ 1.53 (d, 3H, J=6.8 Hz); 2.22 (d, 3H, J=3.3 Hz); 3.44 (s, 5H); 4.26 (m, 1H); 4.39 (t, 1H, J=2.4 Hz); 4.50 (m, 1H); 5.03 (m, 1H); 6.85~6.94 (m, 4H); 7.04 (tt, 1H, J=7.2 and 1.4 Hz); 7.09~7.19 (m, 4H); 7.27~7.31 (m, 4H); 7.37~7.43 (m, 3H); 7.48~7.56 (m, 2H); 7.68 (m, 1H); 7.89 (dd, 2H, J=8.1 and 4.8 Hz); 9.44 (t, 1H, J=7.6 Hz). $^{31}$P NMR (CDCl$_3$, 162 MHz): δ 59.59, −41.03.

EXAMPLE 25

($R_C$, $S_{Fe}$, $R_P$)-2-[1-[(N-Methyl-N-diphenylphosphino)amino]ethyl]-1-[(1-naphthyl)phenylphosphino]ferrocene [($R_C$, $S_{Fe}$, $R_P$)-25]

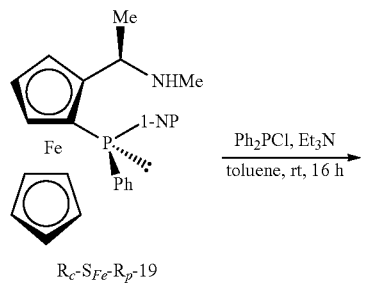

To a solution of ($R_C$, $S_{Fe}$, $S_P$)-22 (XX mg, 1.0 mmol) and Et$_3$N (0.28 mL, 2.0 mmol) in toluene (2.5 mL) was added dropwise chlorodiphenylphosphine (188 uL, 1.05 mmol) at 0° C. Then the mixture was warmed to room temperature, and stirred overnight (16 h) at room temperature, and filtered through a pad of neutral aluminium oxide and eluted with hexane-EtOAc (9:1) to afford the title compound (XX mg, X %) as orange foam. $^1$H NMR (CDCl$_3$, 250 MHz): δ 1.50 (d, 3H, J=6.6 Hz); 2.16 (d, 3H, J=3.0 Hz); 3.68 (s, 5H); 4.08 (m, 1H); 4.33 (m, 1H); 4.42 (m, 2H); 4.56 (m, 1H); 6.98~7.75 (m, 24H). $^{31}$P NMR (CDCl$_3$, 101 MHz): δ 50.70, −35.51.

EXAMPLE 27

(R$_C$, S$_{Fe}$, S$_P$,R$_a$)-27

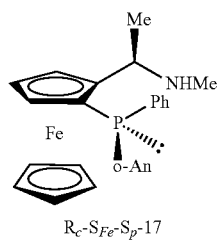

R$_c$-S$_{Fe}$-S$_p$-17

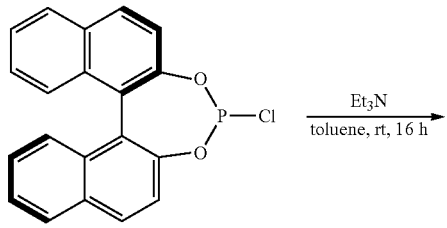

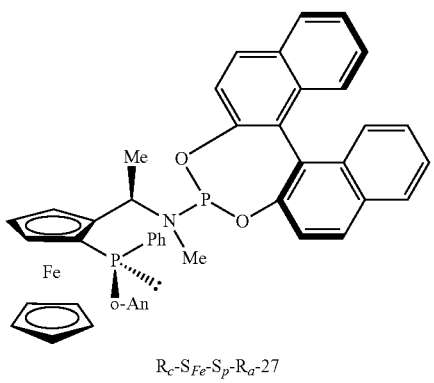

R$_c$-S$_{Fe}$-S$_p$-R$_a$-27

To a solution of (R$_C$, S$_{Fe}$, S$_P$)-17 (229 mg, 0.5 mmol) and Et$_3$N (209 uL, 1.5 mmol) in toluene (4 mL) was added (R)-4-chloro-3,5-dioxa-4-phosphacyclohepta[2,1-a:3,4-a']binaphthalene (175 mg, 0.5 mmol) at 0° C. Then the mixture was warmed to room temperature, and stirred overnight (16 h) at room temperature, and filtered through a pad of neutral aluminium oxide and eluted with hexane-EtOAc (9:1) to afford the title compound (359 mg, 93%) as orange foam. $^1$H NMR (CDCl$_3$, 250 MHz): δ 1.73 (d, 3H, J=3.5 Hz); 1.79 (d, 3H, J=7.0 Hz); 3.71 (s, 3H), 3.80 (m, 1H); 4.00 (s, 5H); 4.31 (t, 1H, J=2.3 Hz); 4.46 (m, 1H); 5.34 (m, 1H); 6.60 (ddd, 1H, J=7.5, 4.5 and 1.8 Hz), 6.72 (t, 1H, J=7.5 Hz), 6.82 (dd, 1H, J=8.8 and 0.8 Hz), 6.91 (ddd, 1H, J=8.8, 4.5 and 0.8 Hz), 7.15~7.38 (m, 11H), 7.58°(m, 2H), 7.77~7.87 (m, 4H). $^{31}$P NMR (CDCl$_3$, 101 MHz): δ 148.51 (d, J=53.4 Hz); −35.37 (d, J=53.4 Hz).

EXAMPLE 28

(R$_C$, S$_{Fe}$, S$_P$,R$_a$)-28

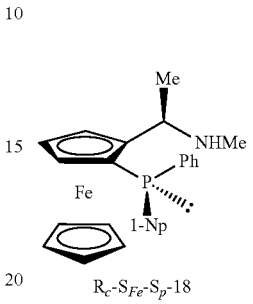

R$_c$-S$_{Fe}$-S$_p$-18

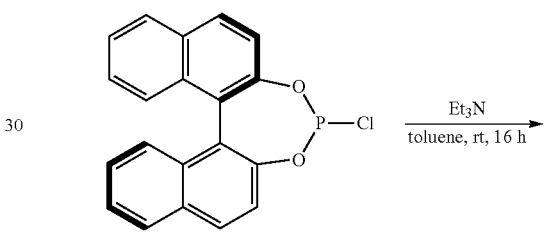

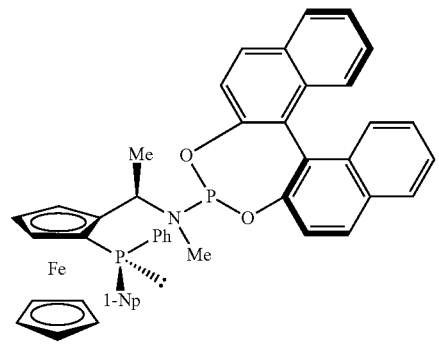

R$_c$-S$_{Fe}$-Sp-R$_a$-28

To a solution of (R$_C$, S$_{Fe}$, S$_P$)-18 (239 mg, 0.5 mmol) and Et$_3$N (209 uL, 1.5 mmol) in toluene (4 mL) was added (R)-4-chloro-3,5-dioxa-4-phosphacyclohepta[2,1-a:3,4-a']binaphthalene (175 mg, 0.5 mmol) at 0° C. Then the mixture was warmed to room temperature, and stirred overnight (16 h) at room temperature, and filtered through a pad of neutral aluminium oxide and eluted with hexane-EtOAc (9:1) to afford the title compound (376 mg, 95%) as orange foam. $^1$H NMR (CDCl$_3$, 250 MHz): δ 0.87 (d, 3H, J=7.0 Hz); 1.82 (d, 3H, J=3.5 Hz); 3.62 (s, 5H); 4.06 (m, 1H); 4.33 (t, 1H, J=2.3 Hz); 4.46 (m, 1H); 5.43 (m, 1H); 6.69 (dd, 1H, J=8.8 and 0.8

Hz), 7.07~7.93 (m, 22H), 9.39 (m, 1H). $^{31}$P NMR (CDCl$_3$, 101 MHz): δ 148.37 (d, J=61.8 Hz); −41.59 (d, J=61.8 Hz).

EXAMPLE 29

(R$_C$, S$_{Fe}$, S$_P$,S$_a$)-29

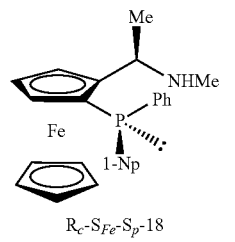

R$_c$-S$_{Fe}$-S$_p$-18

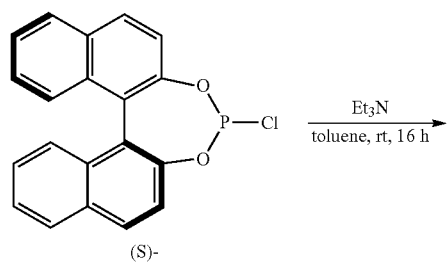

(S)-

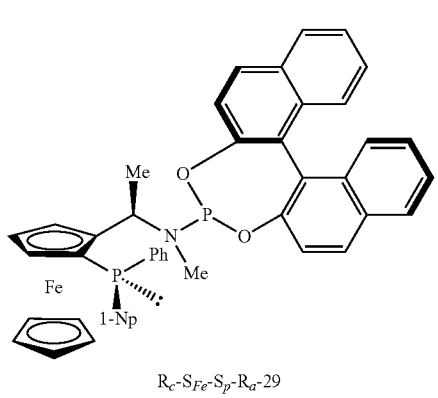

R$_c$-S$_{Fe}$-S$_p$-R$_a$-29

To a solution of (R$_C$, S$_{Fe}$, S$_P$)-18(239 mg, 0.5 mmol) and Et$_3$N (209 uL, 1.5 mmol) in toluene (4 mL) was added (S)-4-chloro-3,5-dioxa-4-phosphacyclohepta[2,1-a:3,4-a']binaphthalene (175 mg, 0.5 mmol) at 0° C. Then the mixture was warmed to room temperature, and stirred overnight (16 h) at room temperature, and filtered through a pad of neutral aluminium oxide and eluted with hexane-EtOAc (9:1) to afford the title compound (373 mg, 95%) as orange foam. $^1$H NMR (CDCl$_3$, 250 MHz): δ 1.71 (d, 3H, J=7.0 Hz); 1.99 (d, 3H, J=3.3 Hz); 3.51 (s, 5H); 4.27 (m, 1H); 4.42 (t, 1H, J=2.3 Hz); 4.51 (m, 1H); 5.28 (m, 1H); 5.98 (d, 1H, J=8.5 Hz), 7.10~7.95 (m, 22H), 9.42 (m, 1H). $^{31}$P NMR (CDCl$_3$, 101 MHz): δ 150.23 (d, J=34.3 Hz); −44.84 (d, J=34.3 Hz).

EXAMPLE 30

(R$_C$, S$_{Fe}$, R$_P$,R$_a$)-30

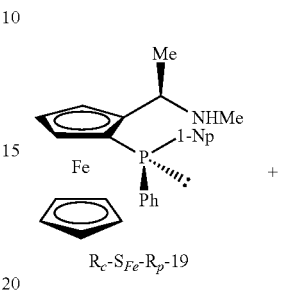

R$_c$-S$_{Fe}$-R$_p$-19

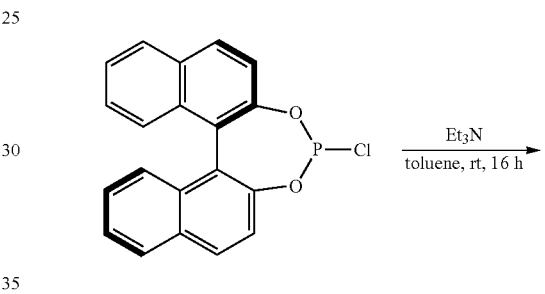

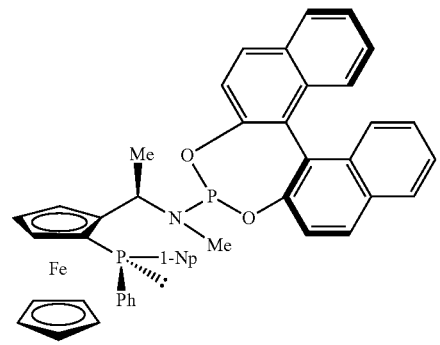

R$_c$-S$_{Fe}$-R$_p$, R$_a$-30

To a solution of (R$_C$, S$_{Fe}$, R$_P$(239 mg, 0.5 mmol) and Et$_3$N (209 uL, 1.5 mmol) in toluene (4 mL) was added (R)-4-chloro-3,5-dioxa-4-phosphacyclohepta[2,1-a:3,4-a']binaphthalene (175 mg, 0.5 mmol) at 0° C. Then the mixture was warmed to room temperature, and stirred overnight (16 h) at room temperature, and filtered through a pad of neutral aluminium oxide and eluted with hexane-EtOAc (9:1) to afford the title compound (371 mg, 95%) as orange foam. $^1$H NMR (CDCl$_3$, 250 MHz): δ 1.64 (d, 3H, J=3.5 Hz); 1.79 (d, 3H, J=7.0 Hz); 4.88 (m, 1H); 4.07 (s, 5H); 4.38 (t, 1H, J=2.3 Hz); 4.52 (m, 1H); 4.91 (dd, 1H, J=8.5 and 0.8 Hz), 5.37 (m, 1H);

6.91 (m, 1H); 7.10~7.90 (m, 21H), 8.44 (m, 1H). $^{31}$P NMR (CDCl$_3$, 101 MHz): δ 148.18 (d, J=54.5 Hz); −32.43 (d, J=54.5 Hz).

EXAMPLE 31

($R_C$, $S_{Fe}$, $R_P$, $S_a$)-31

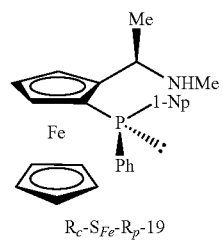

$R_c$-$S_{Fe}$-$R_p$-19

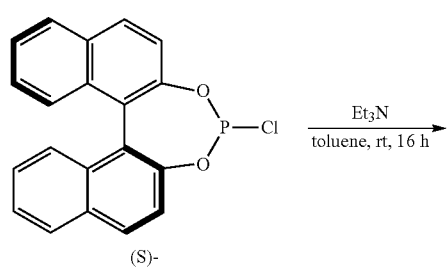

(S)-

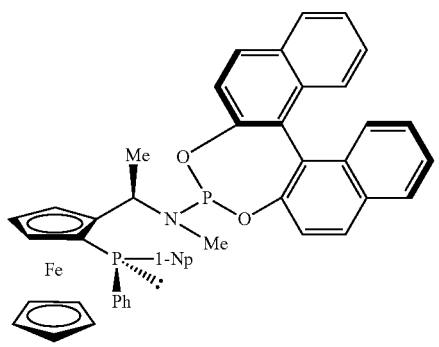

$R_c$-$S_{Fe}$-$R_p$,$S_a$-31

To a solution of ($R_C$, $S_{Fe}$, $R_P$)-19(239 mg, 0.5 mmol) and Et$_3$N (209 uL, 1.5 mmol) in toluene (4 mL) was added (S)-4-chloro-3,5-dioxa-4-phosphacyclohepta[2,1-a:3,4-a']binaphthalene (175 mg, 0.5 mmol) at 0° C. Then the mixture was warmed to room temperature, and stirred overnight (16 h) at room temperature, and filtered through a pad of neutral aluminium oxide and elided with hexane-EtOAc (9:1) to afford the title compound (377 mg, 95%) as orange foam. $^1$H NMR (CDCl$_3$, 250 MHz): δ 1.69 (d, 3H, J=6.8 Hz); 1.86 (d, 3H, J=3.5 Hz); 3.97 (s, 5H); 4.07 (m, 1H); 4.43 (t, 1H, J=2.3 Hz); 4.58 (m, 1H); 5.15 (m, 1H); 5.88 (dd, 1H, J=8.5 and 0.8

Hz), 6.91 (m, 1H); 7.10~7.92 (m, 22H), 8.31 (m, 1H). $^{31}$P NMR (CDCl$_3$, 101 MHz): δ 150.64 (d, J=21.8 Hz); −33.31 (d, J=21.8 Hz).

EXAMPLE 32

($R_C$, $S_{Fe}$, $S_P$, $R_a$)-32

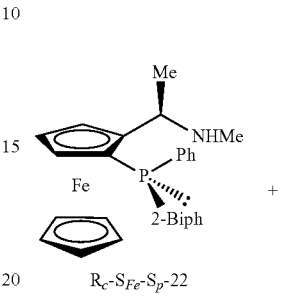

$R_c$-$S_{Fe}$-$S_p$-22

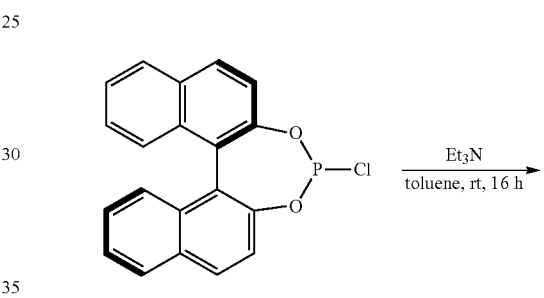

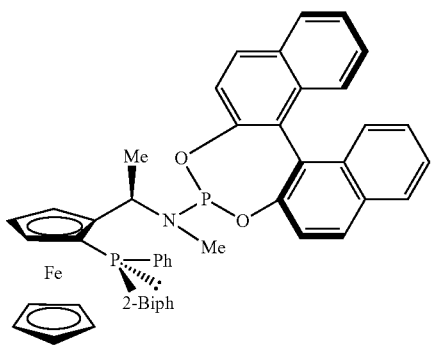

$R_c$-$S_{Fe}$-$S_p$,$R_a$-32

To a solution of ($R_C$, $S_{Fe}$, $S_P$)-22(252 mg, 0.5 mmol) and Et$_3$N (209 uL, 1.5 mmol) in toluene (4 mL) was added (R)-4-chloro-3,5-dioxa-4-phosphacyclohepta[2,1-a:3,4-a']binaphthalene (175 mg, 0.5 mmol) at 0° C. Then the mixture was warmed to room temperature, and stirred overnight (16 h) at room temperature, and filtered through a pad of neutral aluminium oxide and eluted with hexane-EtOAc (9:1) to afford the title compound (392 mg, 96%) as orange foam. $^1$H NMR (CDCl$_3$, 250 MHz): δ 1.63 (d, 3H, J=7.0 Hz); 1.76 (d, 3H, J=3.5 Hz); 3.69 (s, 5H); 4.09 (m, 1H); 4.30 (t, 1H, J=2.3 Hz); 4.34 (m, 1H); 4.89 (m, 1H); 6.71 (dd, 1H, J=8.5 and 0.8

Hz), 7.07~7.84 (m, 25 H). $^{31}$P NMR (CDCl$_3$, 101 MHz): δ 149.07 (d, J=60.5 Hz); −36.59 (d, J=60.5 Hz).

EXAMPLE 33

($R_C$, $S_{Fe}$, $S_P$)-2-(1-Dicyclohexylphosphino)ethyl]-1-[(2-methoxyphenyl)phenylphosphino]ferrocene [($R_C$, $S_{Fe}$, $S_P$)-33]

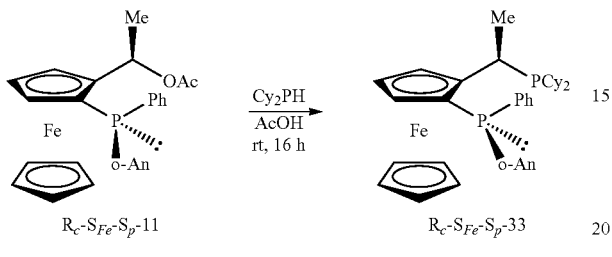

A solution of ($R_C$, $S_{Fe}$, $S_P$)-11 (486 mg, 1.0 mmol) and dicyclohexylphosphine (243 uL, 1.2 mmol) in acetic acid (3 mL) was stirred overnight at room temperature, and poured into 10% K$_2$CO$_3$ aqueous solution (60 mL) with stirring, extracted with Et$_2$O (2×25 mL). The combined ether layers were dried (MgSO$_4$) and concentrated. The residue was purified by chromatography (SiO$_2$, hexane-EtOAc=9:1) to afford the title compound (601 mg, 96%) as orange crystals. $^1$H NMR (CDCl$_3$, 250.13 MHz): δ 1.08~1.68 (m, 25 H), 3.12 (m, 1H), 3.91 (s, 5H), 4.07 (m, 1H), 4.29 (t, 1H, J=2.3 Hz); 4.38 (m, 1H), 6.87~6.98 (m, 2H), 7.15~7.25 (m, 6 H), 7.35 (t, 1H, J=7.3 Hz); $^{31}$P NMR (CDCl$_3$, 101.25 MHz): δ 15.58 (d, J=23.2 Hz); −42.23 (d, J=23.2 Hz).

EXAMPLE 34

($R_C$, $S_{Fe}$, $S_P$)-2-(1-Dicyclohexylphosphino)ethyl]-1-[(1-naphthyl)phenylphosphino]ferrocene [($R_C$, $S_{Fe}$, $S_P$)-34]

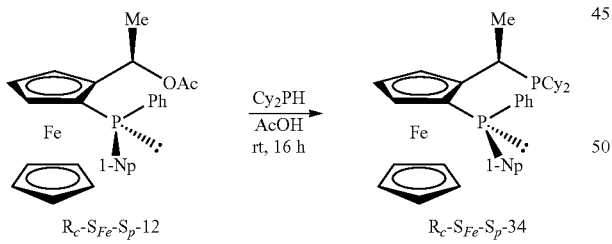

A solution of ($R_C$, $S_{Fe}$, $S_P$)-12 (506 mg, 1.0 mmol) and dicyclohexylphosphine (243 uL, 1.2 mmol) in acetic acid (3 mL) was stirred overnight at room temperature, and poured into 10% K$_2$CO$_3$ aqueous solution (60 mL) with stirring, extracted with Et$_2$O (2×25 mL). The combined ether layers were dried (MgSO$_4$) and concentrated. The residue was purified by chromatography (SiO$_2$, hexane-EtOAc=9:1) to afford the title compound (613 mg, 95%) as orange crystals. $^1$H NMR (CDCl$_3$, 400.13 MHz): δ 1.14~1.57 (m, 25 H); 3.22 (m, 1H); 3.40 (s, 5H); 4.08 (m, 1H); 4.23 (t, 1H, J=2.4 Hz); 4.31 (m, 1H); 7.16~7.22 (m, 5H); 7.36 (dd, 1H, J=8.0 and 7.2 Hz); 7.45~7.49 (m, 2H); 7.60 (ddd, 1H, J=8.5, 6.8 and 1.4 Hz); 7.82 (t, 2H, J=8.1 Hz); 9.28 (dd, 1H, J=7.6 and 6.8 Hz). $^{31}$P NMR (CDCl$_3$, 162 MHz): δ 17.46 (d, J=27.7 Hz); −42.43 (d, J=27.7 Hz).

EXAMPLE 35

($R_C$, $S_{Fe}$, $R_P$)-2-(1-Dicyclohexylphosphino)ethyl]-1-[(1-naphthyl)phenylphosphino]ferrocene [($R_C$, $S_{Fe}$, $R_P$)-35]

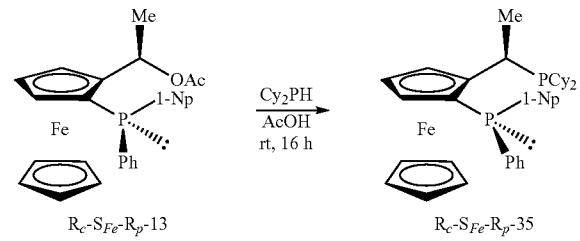

A solution of ($R_C$, $S_{Fe}$, $S_P$)-13 (506 mg, 1.0 mmol) and dicyclohexylphosphine (243 uL, 1.2 mmol) in acetic acid (3 mL) was stirred overnight at room temperature, and poured into 10% K$_2$CO$_3$ aqueous solution (60 mL) with stirring, extracted with Et$_2$O (2×25 mL). The combined ether layers were dried (MgSO$_4$) and concentrated. The residue was purified by chromatography (SiO$_2$, hexane-EtOAc=9:1) to afford the title compound (618 mg, 95%) as orange crystals. $^1$H NMR (CDCl$_3$, 250.13 MHz): δ 0.84~1.85 (m, 25 H), 3.16 (m, 1H), 3.96 (s, 5H), 4.00 (m, 1H), 4.35 (t, 1H, J=2.3 Hz); 4.41 (m, 1H), 7.29~7.40 (m, 7H), 7.62~7.79 (m, 4 H), 8.33 (m, 1H); $^{31}$P NMR (CDCl$_3$, 101.25 MHz): δ 14.93 (d, J=22.8 Hz); −34.80 (d, J=22.8 Hz).

EXAMPLE 36

($R_C$, $S_{Fe}$, $S_P$)-2-(1-Dicyclohexylphosphino)ethyl]-1-[(2-naphthyl)phenylphosphino]ferrocene [($R_C$, $S_{Fe}$, $S_P$)-36]

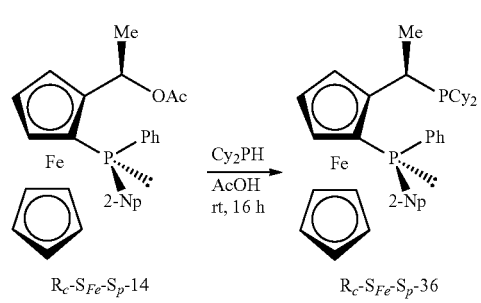

A solution of ($R_C$, $S_{Fe}$, $S_P$)-14 (506 mg, 1.0 mmol) and dicyclohexylphosphine (243 uL, 1.2 mmol) in acetic acid (3 mL) was stirred overnight at room temperature, and poured into 10% K$_2$CO$_3$ aqueous solution (60 mL) with stirring, extracted with Et$_2$O (2×25 mL). The combined ether layers were dried (MgSO$_4$) and concentrated. The residue was purified by chromatography (SiO$_2$, hexane-EtOAc=9:1) to afford the title compound (599 mg, 93%) as orange crystals. $^1$H NMR (CDCl$_3$, 250.13 MHz): δ 1.15~1.71 (m, 25 H), 3.26 (m, 1H), 3.79 (s, 5H), 4.10 (m, 1H), 4.29 (t, 1H, J=2.3 Hz); 4.37

(m, 1H), 7.17~7.24 (m, 5H), 7.34 (m, 1H), 7.50 (d, 1H, J=9.5 Hz); 7.50 (dd, 1H, J=3.0 and 1.5 Hz); 7.57 (ddd, 1H, J=8.3, 5.0 and 1.5 Hz); 7.81 (d, 1H, J=8.5 Hz); 7.87 (m, 1H), 8.31 (d, 1H, J=9.5 Hz); $^{31}$P NMR (CDCl$_3$, 101.25 MHz): δ 15.67 (d, J=30.9 Hz); −34.20 (d, J=30.9 Hz).

EXAMPLE 37

($R_C$, $S_{Fe}$, $R_P$)-2-(1-Dicyclohexylphosphino)ethyl]-1-[(2-naphthyl)phenylphosphino]ferrocene [($R_C$, $S_{Fe}$, $R_P$)-37]

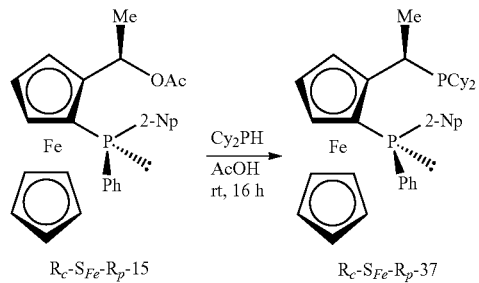

A solution of ($R_C$, $S_{Fe}$, $S_P$)-15 (506 mg, 1.0 mmol) and dicyclohexylphosphine (243 uL, 1.2 mmol) in acetic acid (3 mL) was stirred overnight at room temperature, and poured into 10% K$_2$CO$_3$ aqueous solution (60 mL) with stirring, extracted with Et$_2$O (2×25 mL). The combined ether layers were dried (MgSO$_4$) and concentrated. The residue was purified by chromatography (SiO$_2$, hexane-EtOAc=9:1) to afford the title compound (608 mg, 94%) as orange crystals. $^1$H NMR (CDCl$_3$, 250.13 MHz): δ 1.07~1.68 (m, 25H), 3.26 (m, 1H), 3.85 (s, 5H), 4.07 (m, 1H), 4.34 (t, 1H, J=2.3 Hz); 4.40 (m, 1H); 7.30~7.77 (m, 12H); $^{31}$P NMR (CDCl$_3$, 101.25 MHz): δ 15.56 (d, J=33.1 Hz); −25.12 (d, J=33.1 Hz).

EXAMPLE 38

($R_C$, $S_{Fe}$, $S_P$)-2-(1-Dicyclohexylphosphino)ethyl]-1-[(2-biphenyl)phenylphosphino]ferrocene [($R_C$, $S_{Fe}$, $S_P$)-38]

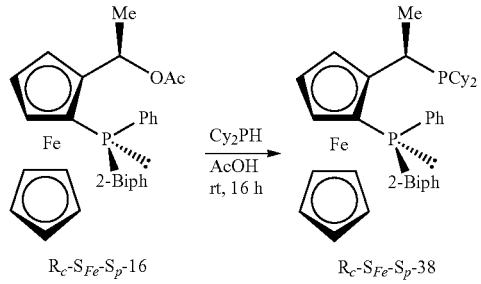

A solution of ($R_C$, $S_{Fe}$, $S_P$)-16 (531 mg, 1.0 mmol) and dicyclohexylphosphine (243 uL, 1.2 mmol) in acetic acid (3 mL) was stirred overnight at room temperature, and poured into 10% K$_2$CO$_3$ aqueous solution (60 mL) with stirring, extracted with Et$_2$O (2×25 mL). The combined ether layers were dried (MgSO$_4$) and concentrated. The residue was purified by chromatography (SiO$_2$, hexane-EtOAc=9:1) to afford the title compound (650 mg, 97%) as orange crystals. $^1$H NMR (CDCl$_3$, 250.13 MHz): δ 1.02~1.72 (m, 25H), 2.93 (m, 1H), 3.66 (s, 5H), 3.76 (m, 1H), 4.29 (t, 1H, J=2.3 Hz); 4.32 (m, 1H), 7.14~7.69 (m, 14H); $^{31}$P NMR (CDCl$_3$, 101.25 MHz): δ 18.44 (d, J=36.7 Hz); −37.67 (d, J=36.7 Hz).

EXAMPLE 39

($R_C$, $S_{Fe}$, $S_P$)-2,2'-Bis[(1-N,N-dimethylamino)ethyl]-1,1'-bis[(2-methoxyphenyl)phenylphosphino]ferrocene [($R_C$, $S_{Fe}$, $S_P$)-40]

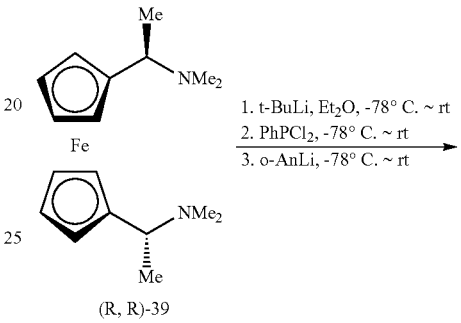

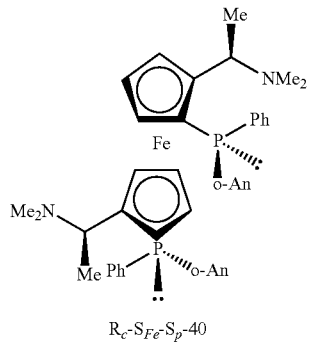

To a solution of (R,R)-1,1'-bis(1-N,N-dimethylaminoethyl)ferrocene [(R,R)-20] (986 mg, 3.0 mmol) in Et$_2$O (30 mL) was added 1.5 M t-BuLi solution in pentane (6.0 mL, 9 mmol) over 10 min via a syringe at −78° C. After addition was completed, the mixture was warmed to room temperature, and stirred for 1.5 h at room temperature. The resulting red solution was cooled to −78° C. again, and dichlorophenylphosphine (1.22 mL, 9.0 mmol) was added in one portion. After stirring for 10 min at −78° C., the mixture was slowly warmed to room temperature, and stirred for 1.5 h at room temperature. The mixture was then cooled to −78° C. again, and a solution of (2-methoxy)phenyllithium [prepared from 2-bromoanisole (1.87 g, 10 mmol) and 1.5 M t-BuLi solution in pentane (13.3 mL, 20 mmol) in Et$_2$O (50 mL) at −78° C.] was added slowly via a cannula. The mixture was warmed to room temperature overnight, and filtered through a pad of Celite. The filtrate was concentrated. The residue was purified by chromatography (SiO$_2$, hexane-EtOAc-Et$_3$N=80:15:5) to afford the title compound (1.10 g, 48%) as yellow foam. $^1$H NMR (CDCl$_3$, 400.13 MHz): δ 1.28 (d, 6H, J=6.7 Hz); 1.71 (s, 12H); 3.16 (m, 2H); 3.84 (s, 6H); 4.05 (m, 2H); 4.16 (m, 2H); 4.53 (t, 2H, J=2.3 Hz); 6.62 (t, 2H, J=7.4 Hz); 6.73 (dd, 2H, J=8.1 and 4.6 Hz); 6.85 (ddd, 2H, J=7.4, 5.3 and 1.8 Hz);

7.03~7.11 (m, 10H); 7.17 (td, 2H, J=8.5 and 1.6 Hz); $^{31}$P NMR (CDCl$_3$, 162 MHz): δ −39.53 (s).

EXAMPLE 40

($R_C$, $S_{Fe}$, $S_P$)-2,2'-Bis[(1-N,N-dimethylamino)ethyl]-1,1'-bis[(1-naphthyl)phenylphosphino]ferrocene [($R_C$, $S_{Fe}$, $S_P$)-41]

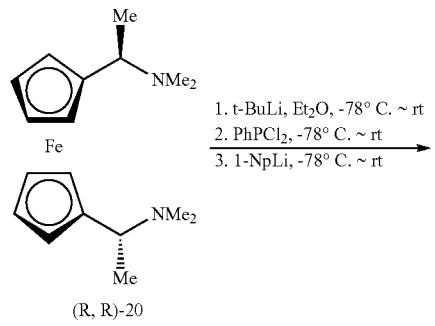

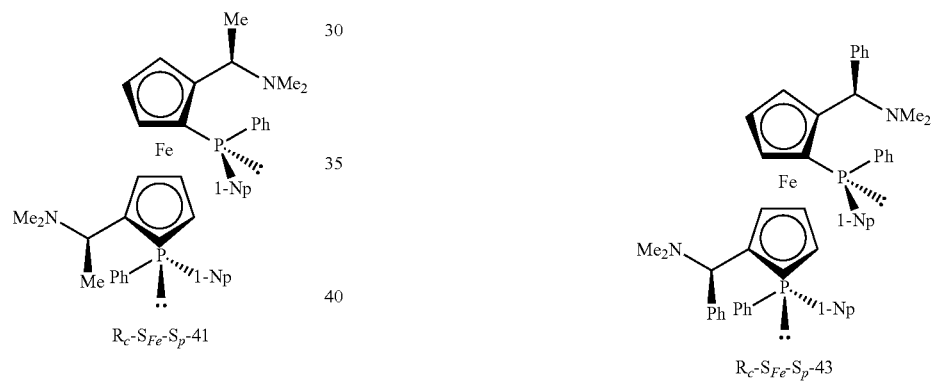

To a solution of (R,R)-1,1'-bis(1-N,N-dimethylaminoethyl)ferrocene [(R,R)-20] (986 mg, 3.0 mmol) in Et$_2$O (30 mL) was added 1.5 M t-BuLi solution in pentane (6.0 mL, 9 mmol) over 10 min via a syringe at −78° C. After addition was completed, the mixture was warmed to room temperature, and stirred for 1.5 h at room temperature. The resulting red solution was cooled to −78° C. again, and dichlorophenylphosphine (1.22 mL, 9.0 mmol) was added in one portion. After stirring for 10 min at −78° C., the mixture was slowly warmed to room temperature, and stirred for 1.5 h at room temperature. The mixture was then cooled to −78° C. again, and a solution of 1-naphthyllithium [prepared from 1-bromonaphthalene (2.07 g, 10 mmol) and 1.5 M t-BuLi solution in pentane (13.3 mL, 20 mmol) in Et$_2$O (50 mL) at −78° C.] was added slowly via a cannula. The mixture was warmed to room temperature overnight, and filtered through a pad of Celite. The filtrate was concentrated. The residue was purified by chromatography (SiO$_2$, hexane-EtOAc-Et$_3$N=80:15:5) to afford the title compound (827 mg, 35%) as yellow crystals. $^1$H NMR (CDCl$_3$, 400.13 MHz): δ 1.28 (d, 6H, J=6.8 Hz); 1.74 (s, 12H); 2.49 (m, 2H); 4.01 (t, 2H, J=2.3 Hz); 4.06 (m, 2H); 4.08 (m, 2H); 6.87~6.93 (m, 4H); 6.99~7.09 (m, 10H); 7.50 (td, 2H, J=8.1 and 1.1 Hz); 7.53 (td, 2H, J=6.8 and 1.3 Hz); 7.70 (d, 2H, J=8.1 Hz); 7.83 (d, 2H, J=8.1 Hz); 9.16 (t, 2H, J=7.1 Hz); $^{31}$P NMR (CDCl$_3$, 162 MHz): δ −39.47 (s).

EXAMPLE 41

($R_C$, $S_{Fe}$, $S_P$)-2,2'-Bis[(α-N,N-dimethylamino)phenylmethyl]-1,1'-bis[(1-naphthyl)phenylphosphino]ferrocene [($R_C$, $S_{Fe}$, $S_P$)-43]

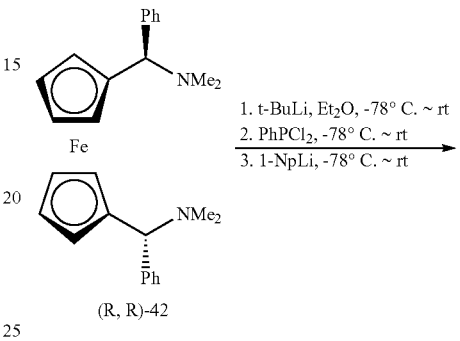

To a solution of (R,R)-1,1'-bis[(α-N,N-dimethylamino)phenylmethyl]ferrocene [(R,R)-23] (903 mg, 2.0 mmol) in Et$_2$O (20 mL) was added 1.5 M t-BuLi solution in pentane (4.0 mL, 6 mmol) over 10 min via a syringe at −78° C. After addition was completed, the mixture was warmed to room temperature, and stirred for 1.5 h at room temperature. The resulting red solution was cooled to −78° C. again, and dichlorophenylphosphine (814 uL, 6.0 mmol) was added in one portion. After stirring for 10 min at −78° C., the mixture was slowly warmed to room temperature, and stirred for 1.5 h at room temperature. The mixture was then cooled to −78° C. again, and a solution of 1-naphthyllithium [prepared from 1-bromonaphthalene (1.45 g, 7 mmol) and 1.5 M t-BuLi solution in pentane (9.3 mL, 14 mmol) in Et$_2$O (40 mL) at −78° C.] was added slowly via a cannula. The mixture was warmed to room temperature overnight, and filtered through a pad of Celite. The filtrate was concentrated. The residue was purified by chromatography (SiO$_2$, hexane-EtOAc=3:1) to afford the title compound (369 mg, 20%) as orange crystals. $^1$H NMR (CDCl$_3$, 250.13 MHz): δ 1.54 (s, 12H); 2.46 (m, 2H); 3.01 (m, 2H); 3.96 (t, 2H, J=2.5 Hz); 4.42 (d, 2H, J=5.3 Hz); 6.69 (ddd, 2H, J=7.3, 4.3 and 1.0 Hz); 6.96~7.34 (m, 22H); 7.55 (d, 2H, J=8.3 Hz); 7.66 (d, 4H, J=8.3 Hz); 7.81 (d, 2H, J=7.8 Hz); 9.20 (t, 2H, J=7.8 Hz); $^{31}$P NMR (CDCl$_3$, 162 MHz): δ −41.73 (s).

EXAMPLE 42

(2'S, 4'S, S$_{Fe}$, R$_P$)-2-[4'-(methoxymethyl-1,3-dioxan-2'-yl]-1-[(2-methoxyphenyl)phenylphosphino]ferrocene [(2'S, 4'S, S$_{Fe}$, R$_P$)-46]

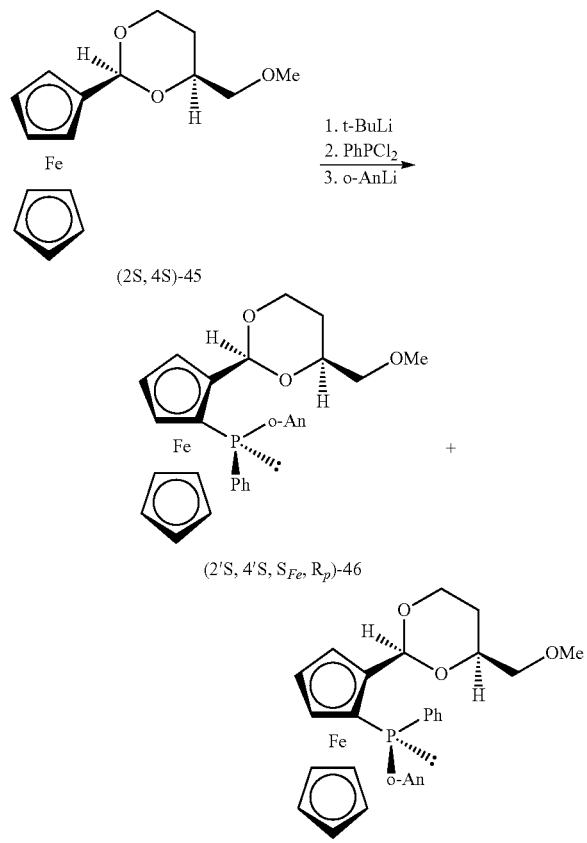

To a solution of (2S,4S)-4-(methoxymethyl)-2-ferrocenyl-1,3-dioxane [(2S,4S)-45] (1.58 g, 5 mmol) in Et$_2$O (20 mL) was added 1.7 M t-BuLi solution in pentane (3.23 mL, 5.5 mmol) at −40° C. After stirring for 10 min, the cooling bath was removed and the mixture was warmed to room temperature, and stirred for 1.5 h at room temperature. The resulting orange suspension was cooled to −78° C., and dichlorophenylphosphine (750 uL, 5.5 mmol) was added in one portion. After stirring for 10 min, the cooling bath was removed and the mixture was warmed to room temperature, and stirred for 1.5 h at room temperature. The mixture was cooled to −78° C. again, a solution of 2-methoxyphenyllithium [prepared from 2-bromoanisole (1.22 mL, 6.5 mmol) and 1.7 M t-BuLi solution in pentane (7.6 mL, 13 mmol) in Et$_2$O (40 mL) at −78° C.] was added slowly via a cannula. The mixture was warmed to room temperature overnight, and filtered through a pad of Celite. The filtrate was concentrated. The residue was purified by chromatography (SiO$_2$, hexane-EtOAc=6:1) to afford the title compound (2.41 g, 91%) as a mixture of two diastereomers (in about 3.3:1 ratio). Recrystallising from hexane, the major product [(2'S, 4'S, S$_{Fe}$, R$_P$)-46] (1.41 g, 53%) was obtained. The absolute configuration of (2'S, 4'S, S$_{Fe}$, R$_P$)-46 was determined by single-crystal X-ray diffraction analysis. $^1$H NMR (CDCl$_3$, 400.13 MHz): 31.42 (dm, 1H, J=13.3 Hz); 1.74 (m, 1H,); 2.89 (d, 2H, J=5.1 Hz); 3.03 (s, 3H); 3.59 (m, 1H); 3.60 (s, 3H); 3.74 (m, 1H); 3.91 (td, 1H, J=12.2 and 2.5 Hz); 4.08 (s, 5H); 4.24~4.27 (m, 2H); 4.70 (m, 1H); 5.71 (d, 1H, J=2.5 Hz); 6.74 (dd, 1H, J=7.9 and 4.6 Hz); 6.80~6.86 (m, 2H); 7.22 (m, 1H); 7.31~7.35 (m, 3H); 7.51~7.56 (m, 2H). $^{31}$P NMR (CDCl$_3$, 162 MHz): δ −31.46 (s).

EXAMPLE 43

(2'S, 4'S, S$_{Fe}$, R$_P$)-2-[4'-(methoxymethyl-1,3-dioxan-2'-yl]-1-[(1-naphthyl)phenylphosphino]ferrocene [(2'S, 4'S, S$_{Fe}$, R$_P$)-47]

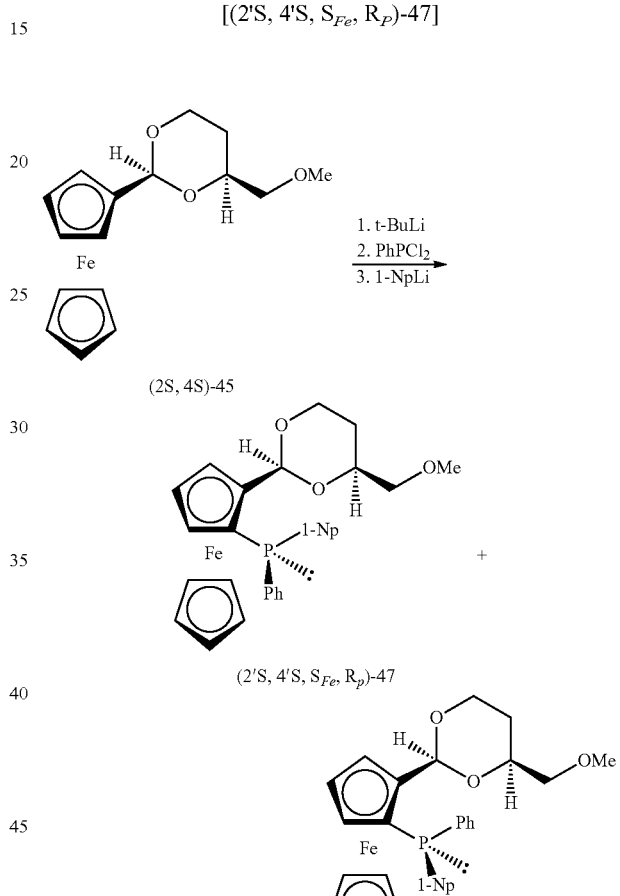

To a solution of (2S,4S)-4-(methoxymethyl)-2-ferrocenyl-1,3-dioxane [(2S,4S)-45] (3.16 g, 10 mmol) in Et$_2$O (40 mL) was added 1.5 M t-BuLi solution in pentane (7.4 mL, 11 mmol) at −40° C. After stirring for 10 min, the cooling bath was removed and the mixture was warmed to room temperature, and stirred for 1.5 h at room temperature. The resulting orange suspension was cooled to −78° C., and dichlorophenylphosphine (1.49 mL, 11 mmol) was added in one portion. After stirring for 10 min, the cooling bath was removed and the mixture was warmed to room temperature, and stirred for 1.5 h at room temperature. The mixture was cooled to −78° C. again, a solution of 1-naphthyllithium [prepared from 1-bromonaphthalene (1.67 mL, 12 mmol) and 1.5 M t-BuLi solution in pentane (16 mL, 24 mmol) in Et$_2$O (60 mL) at −78° C.] was added slowly via a cannula. The mixture was warmed to room temperature overnight, and filtered through a pad of Celite. The filtrate was concentrated. The residue was purified by chromatography (SiO$_2$, hexane-EtOAc=6:1) to afford the title compound (4.95 g, 90%) as a mixture of two diastereomers (in about 3.4:1 ratio), which was recrystallised from hexane to give the pure major product [(2'S, 4'S, S$_{Fe}$, R$_P$)-47] (2.53 g, 51%) as yellow needles. The absolute configuration of (2'S, 4'S, S$_{Fe}$, R$_P$)-47 was determined by single-crystal X-ray diffraction analysis. $^1$H NMR (CDCl$_3$, 400.13 MHz): δ 1.33 (dm, 1H, J=13.3 Hz); 1.63 (m, 1H); 2.56 (dd, 1H, J=10.3 and 4.8 Hz); 2.67 (dd, 1H, J=10.3 and 5.6 Hz); 2.76 (s, 3H); 3.58 (m, 1H); 3.67 (m, 1H); 3.86 (td, 1H, J=12.2 and 2.5 Hz); 4.15 (s, 5H); 3.74 (m, 1H); 4.21 (ddd, 1H, J=11.4, 5.1 and 1.0 Hz); 4.31 (t, 1H, J=2.5 Hz); 4.74 (m, 1H); 5.69 (d, 1H, J=2.5 Hz); 7.16 (ddd, 1H, J=7.1, 5.1 and 1.2 Hz); 7.29~7.40 (m, 6H); 7.54~7.58 (m, 2H); 7.74 (d, 1H, J=8.3 Hz); 7.78 (d, 1H, J=8.0 Hz); 8.25~8.28 (m, 1H). $^{31}$P NMR (CDCl$_3$, 162 MHz): δ −28.03 (s).

EXAMPLE 44

(S$_{Fe}$, R$_P$)-2-[(2-Methoxyphenyl)phenylphosphino]ferrocenecarboxaldehyde [(S$_{Fe}$, R$_P$)-48]

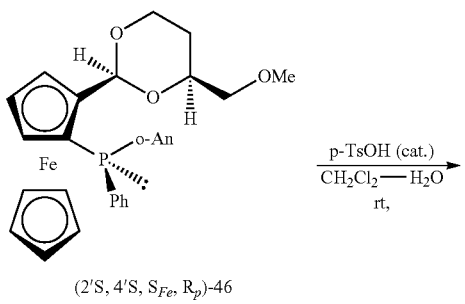

A mixture of acetal [(2'S, 4'S, S$_{Fe}$, R$_P$)-46] (4.0 g, 7.5 mmol), p-TsOH.H2O (2.0 g), CH$_2$Cl$_2$ (50 mL) and H2O (30 mL) was stirred for 24 h at room temperature. The organic layer was separated, washed with saturated NaHCO$_3$ solution (20 mL), dried (MgSO$_4$), and evaporated under reduced pressure to give the crude product (3.20 g, 100%) as red crystals, which was used directly in next step. $^1$H NMR (CDCl$_3$, 250.13 MHz): δ 3.66 (s, 3H); 3.96 (m, 1H); 4.22 (s, 5H); 4.71 (t, 1H, J=2.3 Hz); 5.13 (m, 1H); 6.72 (m, 1H); 6.78~6.87 (m, 2H); 7.29 (m, 1H); 7.41 (m, 3H); 7.54 (m, 2H); 10.24 (d, 1H, J=3.3 Hz). $^{31}$P NMR (CDCl$_3$, 101 MHz): δ −34.66 (s).

EXAMPLE 45

(S$_{Fe}$, R$_P$)-2-[(1-Naphthyl)phenylphosphino]ferrocenecarboxaldehyde [(S$_{Fe}$, R$_P$)-49]

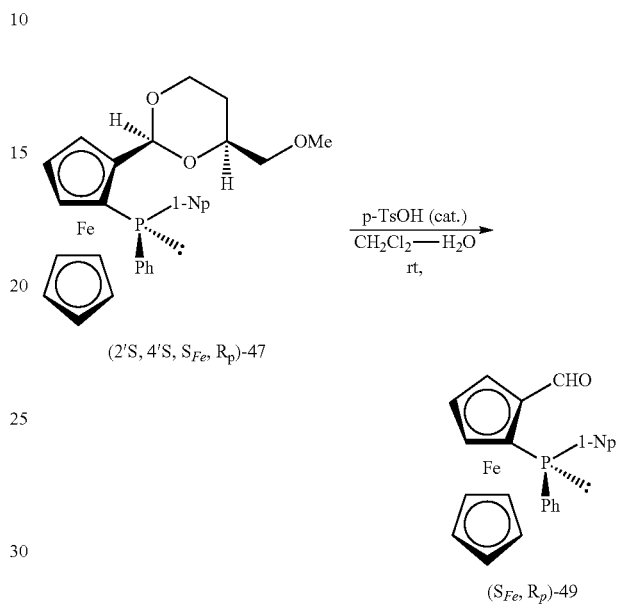

A mixture of acetal [(2'S, 4'S, S$_{Fe}$, R$_P$)-46] (4.73 g, 7.5 mmol), p-TsOH.H$_2$O (2.0 g), CH$_2$Cl$_2$ (50 mL) and H$_2$O (30 mL) was stirred for 24 h at room temperature. The organic layer was separated, washed with saturated NaHCO$_3$ solution (20 mL), dried (MgSO$_4$), and evaporated under reduced pressure to give the crude product (3.36 g, 100%) as red crystals, which was used directly in next step. $^1$H NMR (CDCl$_3$, 250.13 MHz): δ 4.04 (m, 1H); 4.28 (s, 5H); 4.76 (t, 1H, J=2.3 Hz); 5.17 (m, 1H); 7.02 (m, 1H); 7.29~7.48 (m, 6H); 7.52~7.59 (m, 2H); 7.80 (t, 2H, J=7.5 Hz); 8.26 (m, 1H); 10.20 (d, 1H, J=3.0 Hz). $^{31}$P NMR (CDCl$_3$, 101 MHz): δ −30.50 (s).

EXAMPLE 46

(S$_{Fe}$,R$_P$,αS)-2-[(2-Methoxyphenyl)phenylphosphino]-1-[(diphenylphosphinophenyl)]ferrocenemethanol [(S$_P$,αS)-51]

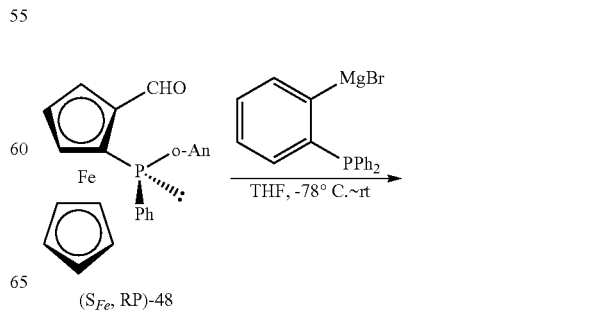

-continued

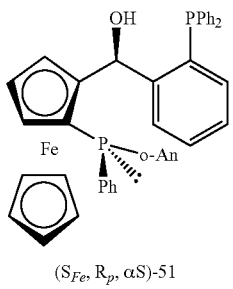

(S$_{Fe}$, R$_p$, αS)-51

A suspension of magnesium turnings (63 mg, 2.6 mmol) and 2-bromophenyl)diphenylphosphine 50 (887 mg, 2.6 mmol) in THF (10 mL) was refluxed until magnesium was dissolved (about 30 min). The resulting Gragnard reagent solution was cooled to −78° C., and a solution of (S$_{Fe}$, R$_P$)-2-[(2-methoxyphenyl)phenylphosphino]ferrocenecarbaoxaldehyde [(S$_{Fe}$, R$_P$)-48] (856 mg, 2.0 mmol) in THF (10 mL) was added slowly via a syringe. After stirring for 5 h at −78° C., the mixture was allowed to warm to room temperature and stirred overnight at room temperature. The reaction was quenched with saturated NH$_4$Cl solution, and extracted with CH$_2$Cl$_2$(2×20 mL). The combined extracts were washed with brine (20 mL), dried (MgSO4), and evaporated under reduced pressure. The residue was purified by flash chromatography (SiO$_2$, hexane-EtOAc=6:1) to give yellow crystals (1.297 g, 96%) as a mixture of two diastereomers (~9:1). Major product: $^1$H NMR (CDCl$_3$, 250 MHz): δ 2.91 (br. s, 1H), 3.57 (m, 1H), 3.59 (s, 3H), 4.05 (m, 1H), 4.14 (t, 1H, J=2.4 Hz), 4.18 (s, 5H), 4.22 (m, 1H), 6.48~4.56 (m, 2H), 6.68~6.80 (m, 2H), 7.02~7.37 (m, 13H); 7.49~7.58 (m, 2H), 7.67 (m, 1H). $^{31}$P NMR (CDCl$_3$, 101 MHz): δ −18.69 (d, J=14.6 Hz), −32.85 (d, J=14.6 Hz).

EXAMPLE 47

(S$_{Fe}$,R$_P$,αS)-2-[(1-Naphthyl)phenylphosphino]-1-[α-[(diphenylphosphinophenyl)]ferrocenemethanol [(S$_{Fe}$,R$_P$,αS)-52]

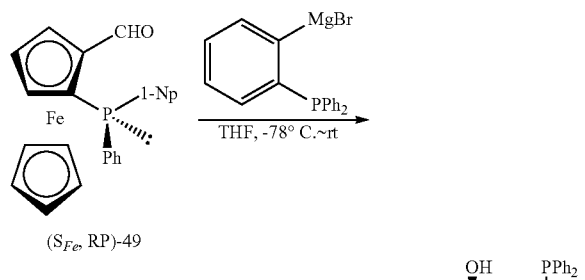

(S$_{Fe}$, R$_p$, αS)-52

A suspension of magnesium turnings (63 mg, 2.6 mmol) and 2-bromophenyl)diphenylphosphine 50 (887 mg, 2.6 mmol) in THF (10 mL) was refluxed until magnesium was dissolved (about 30 min). The resulting Gragnard reagent solution was cooled to −78° C., and a solution of (S$_{Fe}$, R$_P$)-2-[(1-naphthyl)phenylphosphino]ferrocenecarbaoxaldehyde [(S$_{Fe}$, R$_P$)-49] (897 mg, 2.0 mmol) in THF (10 mL) was added slowly via a syringe. After stirring for 5 h at −78° C., the mixture was allowed to warm to room temperature and stirred overnight at room temperature. The reaction was quenched with saturated NH$_4$Cl solution, and extracted with CH$_2$Cl$_2$ (2×20 mL). The combined extracts were washed with brine (20 mL), dried (MgSO$_4$), and evaporated under reduced pressure. The residue was purified by flash chromatography (SiO$_2$, hexane-EtOAc=6:1) to give yellow crystals (1.322 g, 93%) as a mixture of two diastereomers (~9:1). Major product: $^1$H NMR (CDCl$_3$, 250 MHz): δ 2.39 (br. s, 1H), 3.66 (m, 1H), 4.24 (s, 5H), 4.29 (t, 1H, J=2.4 Hz), 4.57 (m, 1H), 4.22 (m, 2H), 6.40~4.49 (m, 3H), 6.61~6.67 (m, 2H), 6.83~7.01 (m, 4H); 7.10~7.59 (m, H), 7.75 (br. D, 1H, J=7.8 Hz), 8.28 (m, 1H). $^{31}$P NMR (CDCl$_3$, 101 MHz): δ −18.54 (d, J=21.0 Hz), −29.56 (d, J=21.0 Hz).

EXAMPLE 48

(S$_{Fe}$,R$_P$,αS)-2-[(2-Methoxyphenyl)phenylphosphino]-1-[α-methoxy-(2-diphenylphosphinophenylmethyl)]ferrocene [(S$_{Fe}$,R$_P$,αS)-53]

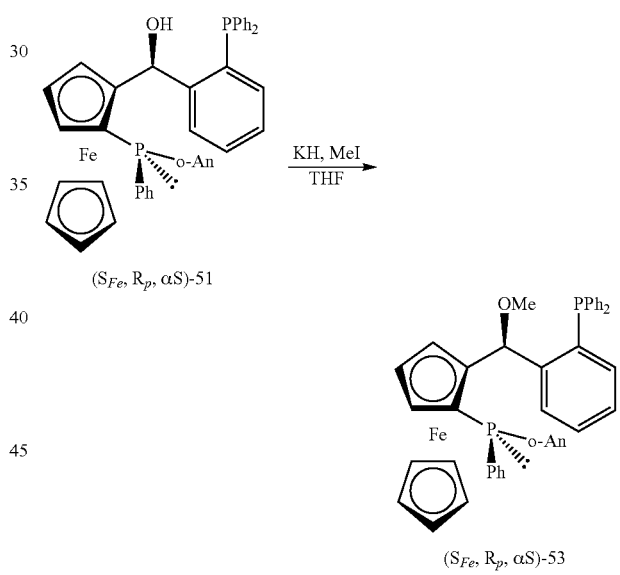

To a suspension of KH (30%, 174 mg, 1.3 mmol washed with hexane) in THF (10 mL) was added alcohol [(S$_P$,αS)-51] (690 g, 1.0 mmol) at 0° C. After stirring for 2 h at 0° C., iodomethane (68 uL, 1.1 mmol) was added via a syringe, then the mixture was stirred for 2 h at 0° C. The reaction was quenched with MeOH (0.5 mL), and the solvents were removed under reduced pressure. The residue was dissolved in CH$_2$Cl$_2$ (20 mL), washed with water (10 mL) and brine (10 mL), dried (MgSO$_4$), and evaporated under reduced pressure. The residue was purified by flash chromatography (SiO$_2$, hexane-EtOAc=10:1) to give yellow crystals (463 mg, 66%). $^1$H NMR (CDCl$_3$, 250 MHz): δ 2.82 (s, 3H), 3.50 (m, 1H), 3.57 (s, 3H), 4.11 (t, 1H, J=2.3 Hz), 4.17 (s, 5H), 4.19 (m, 1H), 5.79 (d, 1H, J=6.8 Hz), 6.54~6.64 (m, 2H), 6.69 (m, 1H), 6.84 (ddd, 1H, J=7.8, 4.3 and 1.5 Hz), 7.02~7.37 (m, 12H), 7.52 (m, 2H), 7.66 (m, 1H); $^{31}$P NMR (CDCl$_3$, 101 MHz): δ −18.44 (d, J=18.7 Hz), —31.19 (d, J=18.7 Hz).

EXAMPLE 49

($S_{Fe}$,αS)-2-Bromo-1-[α-(2-diphenylphosphinophenyl)]ferrocenemethanol [($S_{Fe}$,αS)-55]

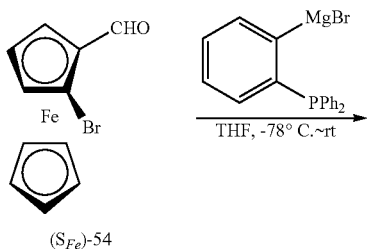

($S_{Fe}$)-54

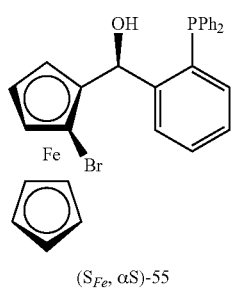

($S_{Fe}$, αS)-55

A suspension of Mg (729 mg, 30 mmol) in THF (10 mL) was added dropwise a solution of 2-bromophenyldiphenylphosphine (50) (9.42 g, 27.6 mmol) in THF (30 mL) at about 50° C. After addition, the mixture was refluxed for 1 h, cooled room temperature, and added to a solution of ($S_{Fe}$)-2-bromoferrocenecarboxaldehyde [($S_{Fe}$)-54](6.74 g, 23 mmol) in Et$_2$O (20 mL) at −78° C. After stirring for 6 h at −78° C., the mixture was warmed to room temperature, and stirred overnight at room temperature. The reaction was quenched with saturated NH$_4$Cl solution (50 mL), and diluted with EtOAc (100 mL). The organic layer was separated, washed with brine (50 mL), dried (Na$_2$SO$_4$), and evaporated under reduced pressure. The residue was purified by chromatography (SiO$_2$, hexane-EtOAc=5:1) to give yellow crystals (12.51 g, 98%) as a single diastereomer. $^1$H NMR (CDCl$_3$, 250 MHz): δ 2.67 (dd, 1H, J=3.5 and 2.0 Hz), 4.04 (t, 1H, J=2.5 Hz), 4.18 (m, 1H), 4.27 (s, 5H), 4.40 (m, 1H), 6.47 (dd, 1H, J=6.5 and 3.5 Hz), 7.00 (m, 1H), 7.18 (m, 1H), 7.15~7.37 (m, 12H); $^{31}$P NMR (CDCl$_3$, 101 MHz): δ −17.30.

EXAMPLE 50

($S_{Fe}$,αS)-2-Bromo-1-[α-methoxy-(2-diphenylphosphinophenylmethyl)]ferrocene [($S_{Fe}$,αS)-56]

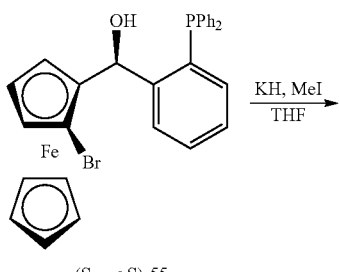

($S_{Fe}$, αS)-55

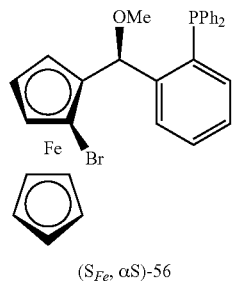

($S_{Fe}$, αS)-56

To a suspension of KH (30%, 3.75 g, 28.1 mmol), washed with hexane) in THF (20 mL) was added a solution of ($S_P$, αS)-2-Bromo-1-[α-(2-diphenylphosphinophenyl)]ferrocenemethanol [($S_{Fe}$,αS)-55] (12.00 g, 21.6 mmol) in THF (180 mL) at 0° C. After stirring for 2 h at 0° C., iodomethane (1.48 mL, 23.8 mmol) was added via a syringe, then the mixture was stirred for 1 h at 0° C. The reaction was quenched with MeOH (5 mL), and the solvents were removed under reduced pressure. The residue was dissolved in EtOAc (150 mL), washed with water (100 mL) and brine (100 mL), dried (MgSO$_4$), and evaporated under reduced pressure. The residue was purified by flash chromatography (SiO$_2$, hexane-EtOAc=5:1) to give yellow crystals (12.10 g, 98%). $^1$H NMR (CDCl$_3$, 250 MHz): δ 3.29 (s, 3H), 3.96 (t, 1H, J=2.5 Hz), 4.01 (m, 1H), 4.27 (s, 5H), 4.33 (m, 1H), 6.09 (d, 1H, J=7.8 Hz), 7.04 (m, 1H), 7.15~7.37 (m, 12H), 7.44 (m, 1H); $^{31}$P NMR (CDCl$_3$, 101 MHz): δ −18.46.

EXAMPLE 51

($S_{Fe}$,$S_P$,αS)-2-[(2-Methoxyphenyl)phenylphosphino]-1-[α-methoxy-(2-diphenylphosphinophenylmethyl)]ferrocene [($S_{Fe}$,$S_P$,αS)-57]

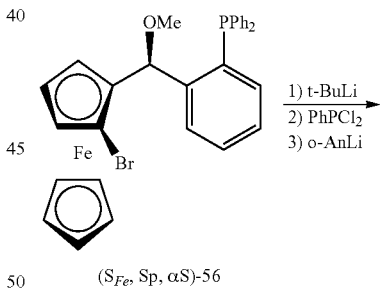

($S_{Fe}$, Sp, αS)-56

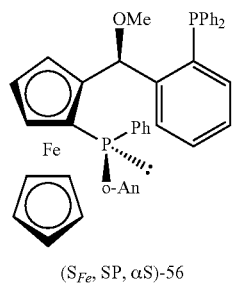

($S_{Fe}$, SP, αS)-56

To a solution of bromide [($S_{Fe}$,αS)-56] (2.85 g, 5 mmol) in THF (30 mL) was added slowly 1.7 M t-BuLi (6.5 mL, 11 mmol) via a syringe at −78° C. After stirring for 10 min at −78° C., PhPCl$_2$ (746 uL, 5.5 mmol.) was added via a syringe, After stirring for 30 min at −78° C., the mixture was warmed to room temperature and stirred for 1 h at room temperature. the mixture was cooled to −78° C. again, and a suspension of o-AnLi [prepared from 2-bromoanisole (805 uL, 6.5 mmol) and 1.7 M t-BuLi (7.6 mL, 13 mmol) in Et$_2$O (30 mL) at −78° C.] was added via a cannula, then the mixture was stirred overnight at −78° C. to room temperature. The reaction was quenched with water (20 mL), The organic layer was separated, washed with brine (30 mL), dried (MgSO$_4$), and evaporated under reduced pressure. The residue was purified by flash chromatography (SiO$_2$, hexane-EtOAc=10:1) to give yellow crystals (3.21 g, 91%) as a single diastereomer. $^1$H NMR (CDCl$_3$, 250 MHz): δ 2.71 (s, 3H), 3.67 (m, 1H), 3.90 (m, 1H), 3.96 (s, 3H), 4.06 (t, 1H, J=2.3 Hz), 4.22 (s, 5H), 5.52 (d, 1H, J=6.5 Hz), 6.80~6.98 (m, 4H), 7.08~7.36 (m, 14H), 7.76 (m, 1H); $^{31}$P NMR (CDCl$_3$, 101 MHz): δ −17.98 (d, J=10.0 Hz), −33.15 (d, J=10.0 Hz).

EXAMPLE 52

($S_{Fe}$,$S_P$,αS)-2-[(1-Naphthyl)phenylphosphino]-1-[α-methoxy-(2-diphenylphosphinophenylmethyl)]ferrocene [($S_{Fe}$,$S_P$,αS)-58] and ($S_{Fe}$,$R_P$,αS)-2-[(1-Naphthyl)phenylphosphino]-1-[α-methoxy-(2-diphenylphosphinophenylmethyl)]ferrocene [($S_{Fe}$,$R_P$,αS)-59]

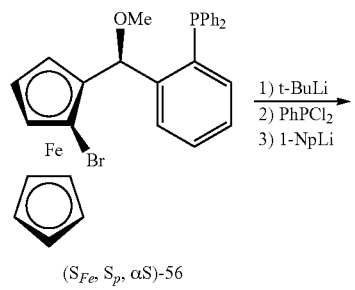

($S_{Fe}$, $S_p$, αS)-56

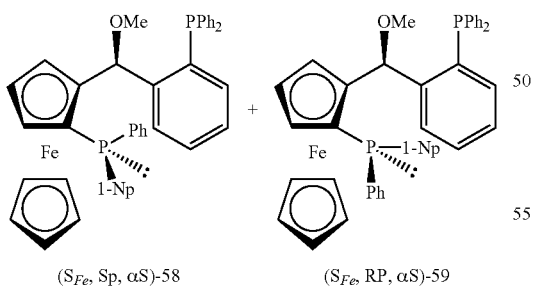

($S_{Fe}$, Sp, αS)-58    ($S_{Fe}$, RP, αS)-59

To a solution of bromide [($S_{Fe}$,αS)-56] (2.85 g, 5 mmol) in THF (30 mL) was added slowly 1.7 M t-BuLi (6.5 mL, 11 mmol) via a syringe at −78° C. After stirring for 10 min at −78° C., PhPCl$_2$ (746 uL, 5.5 mmol.) was added via a syringe, After stirring for 30 min at −78° C., the mixture was warmed to room temperature and stirred for 1 h at room temperature. Tthe mixture was cooled to −78° C. again, and a suspension of o-AnLi [prepared from 1-bromonaphthalene (900 uL, 6.5 mmol) and 1.7 M t-BuLi (7.6 mL, 13 mmol) in Et$_2$O (30 mL) at −78° C.] was added via a cannula, then the mixture was stirred overnight at −78° C. to room temperature. The reaction was quenched with water (20 mL), The organic layer was separated, washed with brine (30 mL), dried (MgSO$_4$), and evaporated under reduced pressure. The residue was purified by flash chromatography (SiO$_2$, hexane-EtOAc=10:1) to give yellow crystals (3.30 g, 91%) as a mixture of two diastereomers (ratio: ~9:1), which was recrystallised from hexane to give pure major product [($S_{Fe}$,$S_P$,αS)-58] (2.83 g, 78%) as yellow crystals. The mother liquor was concentrated, and the residue was recrystallized from MeOH to afford pure minor product [($S_{Fe}$,$R_P$,αS)-59] (217 mg, 6%) as yellow crystals. Major product [($S_{Fe}$,$S_P$,αS)-58]: $^1$H NMR (CDCl$_3$, 250 MHz): δ 2.96 (s, 3H), 3.74 (m, 1H), 3.84 (s, 5H), 4.13 (t, 1H, J=2.5 Hz), 4.20 (m, 1H), 6.04 (d, 1H, J=7.3 Hz), 6.89~7.41 (m, 20H), 7.55 (ddd, 1H, J=8.0, 6.8 and 1.3 Hz), 7.64 (dd, 1H, J=6.8 and 1.5 Hz), 7.69 (ddd, 1H, J=5.3, 3.5 and 1.7 Hz), 7.89 (t, 2H, J=8.0 Hz), 9.32 (dd, 1H, J=7.5 and 6.8 Hz). $^{31}$P NMR (CDCl$_3$, 101 MHz): δ −18.83 (d, J=21.3 Hz), —35.08 (d, J=21.3 Hz). Minor product [($S_{Fe}$,$R_P$,αS)-59]: $^1$H NMR (CDCl$_3$, 250 MHz): δ 2.73 (s, 3H), 3.61 (m, 1H), 4.21 (t, 1H, J=2.5 Hz), 4.22 (s, 5H), 4.28 (m, 1H), 5.86 (d, 1H, J=7.3 Hz), 6.67 (ddd, 1H, J=7.8, 4.3 and 1.3 Hz), 6.79~7.61 (m, 23H), 7.75 (br. d, 1H, J=8.0 Hz), 8.29 (m, 1H). $^{31}$P NMR (CDCl$_3$, 101 MHz): δ −18.52 (d, J=18.4 Hz), −27.69 (d, J=18.4 Hz).

EXAMPLE 53

($S_{Fe}$, $R_P$)-2-[(2-Methoxyphenyl)phenylphosphino]ferrocenemethanol [($S_{Fe}$, $R_P$)-60]

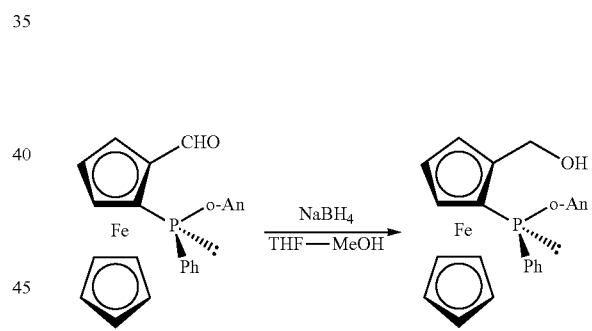

($S_{Fe}$, $R_p$)-48    ($S_{Fe}$, $R_p$)-60

To a solution of aldehyde [($S_{Fe}$, $R_P$)-48] (856 mg, 2.0 mmol) in THF (10 mL) was added NaBH$_4$ (38 mg, 1.0 mmol) at 0° C., then MeOH (2 mL) was added. After stirring for 2 h at 0° C., the mixture was warmed to room temperature and stirred overnight at room temperature. The reaction was quenched with saturated NH$_4$Cl solution (5 mL), and diluted with EtOAc (10 mL). The organic layer was separated, washed with brine (10 mL), dried (MgSO$_4$), and evaporated under reduced pressure to give the crude product (857 mg, 100%) as yellow crystals, which was used directly in next step. $^1$H NMR (CDCl$_3$, 250 MHz): δ 3.63 (m, 1H), 3.66 (s, 3H), 4.10 (s, 5H), 4.29 (t, 1H, J=2.0 Hz), 4.41 (d, 1H, J=12.5 Hz), 4.53 (m, 1H), 4.58 (dd, 1H, J=12.5 and 2.0 Hz), 6.77~6.90 (m, 3H), 7.28 (m, 1H), 7.34~7.41 (m, 3H), 7.48~7.55 (m, 2H). $^{31}$P NMR (CDCl$_3$, 101 MHz): δ −35.05.

EXAMPLE 54

($S_{Fe}$, $R_P$)-2-[(1-Naphthyl)phenylphosphino] ferrocenemethanol [($S_{Fe}$, $R_P$)-61]

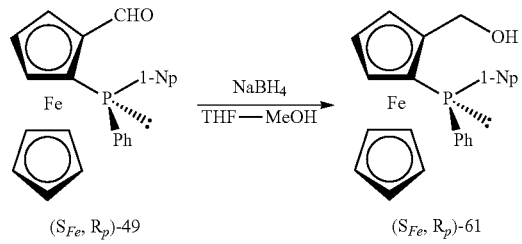

To a solution of aldehyde [($S_{Fe}$, $R_P$)-49] (897 mg, 2.0 mmol) in THF (10 mL) was added NaBH$_4$ (38 mg, 1.0 mmol) at 0° C., then MeOH (2 mL) was added. After stirring for 2 h at 0° C., the mixture was warmed to room temperature and stirred overnight at room temperature. The reaction was quenched with saturated NH$_4$Cl solution (5 mL), and diluted with EtOAc (10 mL). The organic layer was separated, washed with brine (10 mL), dried (MgSO$_4$), and evaporated under reduced pressure to give the crude product (900 mg, 100%) as yellow crystals, which was used directly in next step. $^1$H NMR (CDCl$_3$, 250 MHz): δ 3.71 (m, 1H), 4.16 (s, 5H), 4.36 (t, 1H, J=2.5 Hz), 4.41 (d, 1H, J=12.5 Hz), 4.54 (dd, 1H, J=12.5 and 1.3 Hz), 4.58 (m, 1H), 7.11 (ddd, 1H, J=7.0, 4.5 and 1.3 Hz), 7.30~7.57 (m, 8H), 7.80 (m, 2H), 8.26 (m, 1H). $^{31}$P NMR (CDCl$_3$, 101 MHz): δ −31.14.

EXAMPLE 55

($S_{Fe}$, $R_P$)-2-[(2-Methoxyphenyl)phenylphosphino] ferrocenemethanol acetate [($S_{Fe}$, $R_P$)-62]

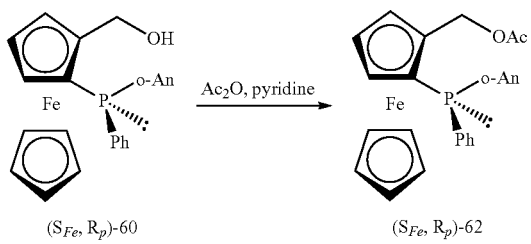

A solution of alcohol [($S_{Fe}$, $R_P$)-60] (857 mg, 2.0 mmol), Ac$_2$O (2 mL) and pyridine (2 mL) in CH$_2$Cl$_2$ (10 mL) was stirred overnight at room temperature. The volatile matters were removed under reduced pressure below 35° C. to give the crude product (880 mg, 100%) as yellow crystals, which was used directly in next step. $^1$H NMR (CDCl$_3$, 250 MHz): δ 1.62 (s, 3H), 3.64 (s, 4H, overlapped), 4.10 (s, 5H), 4.30 (t, 1H, J=2.5 Hz), 4.54 (m, 1H), 5.01 (d, 1H, J=12.0 Hz), 5.12 (dd, 1H, J=12.0 and 2.3 Hz), 6.77 (m, 2H), 6.83 (t, 1H, J=7.5 Hz), 7.25 (m, 1H), 7.37 (m, 3H), 7.51 (m, 2H). $^{31}$P NMR (CDCl$_3$, 101 MHz): δ −34.60.

EXAMPLE 56

($S_{Fe}$, $R_P$)-2-[(1-Naphthyl)phenylphosphino]ferrocenemethanol acetate [($S_{Fe}$, $R_P$)-63]

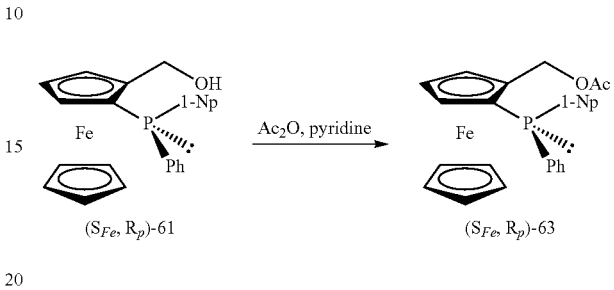

A solution of alcohol [($S_{Fe}$, $R_P$)-61] (900 mg, 2.0 mmol), Ac$_2$O (2 mL) and pyridine (2 mL) in CH$_2$Cl$_2$ (10 mL) was stirred overnight at room temperature. The volatile matters were removed under reduced pressure below 35° C. to give the crude product (983 mg, 100%) as yellow crystals, which was used directly in next step. $^1$H NMR (CDCl$_3$, 250 MHz): δ 1.46 (s, 3H), 3.74 (m, 1H), 4.15 (s, 5H), 4.38 (t, 1H, J=2.5 Hz), 4.59 (m, 1H), 5.00 (d, 1H, J=1.3.5 Hz), 7.28~7.45 (m, 5H), 7.54 (m, 1H), 7.69 (tt, 1H, J=7.8 and 1.8 Hz), 7.78 (m, 2H), 8.23 (m, 1H), 8.64 (m, 2H). $^{31}$P NMR (CDCl$_3$, 101 MHz): δ −30.85.

EXAMPLE 57

($S_{Fe}$, $R_P$)-1-[(Dicyclohexylphosphino)methyl]-2-[(2-methoxyphenyl)phenylphosphino]ferrocene [($S_{Fe}$, $R_P$)-64]

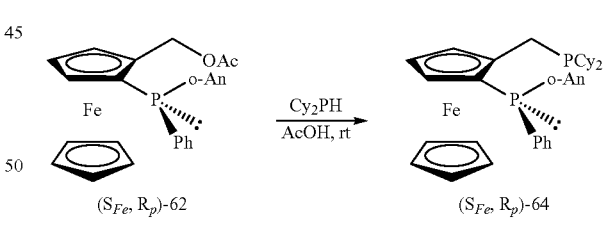

A solution of ($S_{Fe}$, $R_P$)-62 (472 mg, 1.0 mmol) and dicyclohexylphosphine (243 uL, 1.2 mmol) in acetic acid (3 mL) was stirred for 7 days at room temperature, and poured into 10% K$_2$CO$_3$ aqueous solution (60 mL) with stirring, extracted with Et$_2$O (2×25 mL). The combined ether layers were dried (MgSO$_4$) and concentrated. The residue was purified by chromatography (SiO$_2$, hexane-EtOAc=9:1) to afford the title compound (573 mg, 94%) as orange crystals. $^1$H NMR (CDCl$_3$, 250.13 MHz): δ 0.99~1.79 (m, 22 H), 2.56 (br. d, 1H, J=12.5 Hz), 2.73 (br. d, 1H, J=12.5 Hz), 3.58 (m, 1H), 4.00 (s, 5H), 4.20 (m, 1H), 4.57 (m, 1H); 4.32 (m, 1H), 6.74~7.58 (m, 9 H); $^{31}$P NMR (CDCl$_3$, 101.25 MHz): δ −2.93; −35.19.

EXAMPLE 58

(S$_{Fe}$, R$_P$)-1-[(Dicyclohexylphosphino)methyl]-2-[(1-naphthyl)phenylphosphino]ferrocene [(S$_{Fe}$, R$_P$)-65]

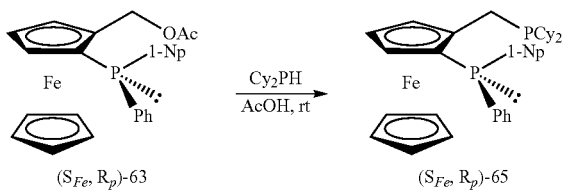

A solution of (S$_{Fe}$, R$_P$)-63 (492 mg, 1.0 mmol) and dicyclohexylphosphine (243 uL, 1.2 mmol) in acetic acid (3 mL) was stirred for 7 days at room temperature, and poured into 10% K$_2$CO$_3$ aqueous solution (60 mL) with stirring, extracted with Et$_2$O (2×25 mL). The combined ether layers were dried (MgSO$_4$) and concentrated. The residue was purified by chromatography (SiO$_2$, hexane-EtOAc=9:1) to afford the title compound (599 mg, 95%) as orange crystals. $^1$H NMR (CDCl$_3$, 250.13 MHz): δ 0.83~1.76 (m, 22 H), 2.57 (dm, 1H, J=12.5 Hz), 2.70 (dm, 1H, J=12.5 Hz), 3.67 (m, 1H), 4.06 (s, 5H), 4.27 (t, 1H, J=2.5 Hz), 4.60 (m, 1H); 7.12 (m, 1H), 7.31~7.82 (m, 10 H);8.28 (m, 1H). $^{31}$P NMR (CDCl$_3$, 101.25 MHz): δ −2.19; −31.85.

EXAMPLE 59

(S$_C$, S$_{Fe}$, R$_P$)-67

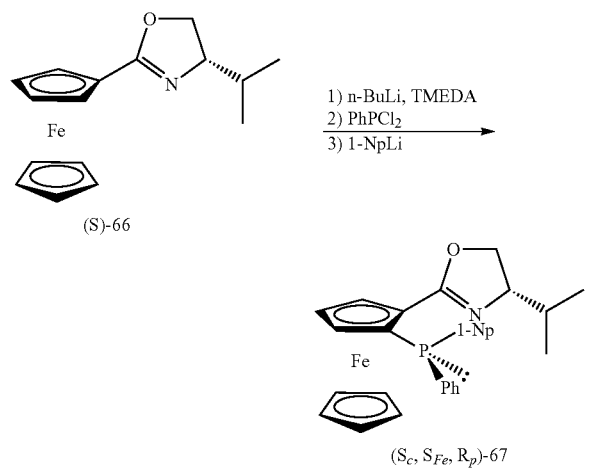

To a solution of (S)-66 (1.56 g, 5 mmol) and TMEDA (1.0 mL, 6.5 mmol) in Et$_2$O (50 mL) was added 2.5 M n-BuLi (2.6 mL, 6.5 mmol) at −78° C., After stirring for 3 h at −78° C., PhPCl$_2$ (0.95 mL, 7.0 mmol) was added, After stirring for 20 min at −78° C., the mixture was warmed to room temperature and stirred for 1.5 h at room temperature. The mixture was cooled to −78° C. again, and a suspension of 1-NpLi [prepared from 1-bromonaphthalene (1.39 mL, 10 mmol) and 1.7 M t-BuLi (11.8 mL, 20 mmol) in Et$_2$O (40 mL) at −78° C.] was added via a cannula. The mixture was stirred and warmed to room temperature overnight. The reaction was quenched by water (40 mL). The organic layer was separated, washwd with brine (40 mL), dried (MgSO$_4$), and concentrated. The residue was purified by chromatography (SiO$_2$, EtOAc-hexane=1:5~1:3) to give the product (2.25 g, 85%) as an orange crystals. $^1$H NMR and $^{31}$P NMR analysis show the de is about 9:1. Major product $^1$H NMR (CDCl$_3$, 400.13 MHz): δ 0.58 (d, 3H, J=6.7 Hz); 0.73 (d, 3H, J=6.7 Hz); 1.58 (m, 1H), 3.45 3.52 (m, 2H), 3.61 (m, 1H), 3.78 (m, 1H), 4.29 (s, 5H); 4.44 (t, 1H, J=2.6 Hz); 5.05 (m, 1H); 7.08 (dd, 1H, J=7.0 and 4.4 Hz); 7.24~7.48 (m, 8H); 7.74 (d, 1H, J=8.0 Hz); 7.80 (d, 1H, J=8.0 Hz); 8.37 (dd, 1H, J=8.3 and 4.3 Hz). $^{31}$P NMR (CDCl$_3$, 162 MHz): δ −23.52 (s).

Asymmetric Hydrogenation-General Procedure:

Bis(1,5-cyclooctadiene)rhodium trifluoromethanesulfonate [Rh(COD)$_2$TfO] (2.3 mg, 5 umol) and the desired ligand (6 umol)) were placed in a vessel which was purged with argon. The desired solvent was degassed with Ar for 15 minutes, then 5.0 mL was added to the reaction vessel via syringe. This solution was stirred at 25° C. under argon for 15 minutes. The desired substrate (1.0 mmol) was then added to the catalyst solution. The solution was then purged five times with argon and pressurized with hydrogen to the desired pressure and stirred at room temperature. The reactions were run for the desired time at the desired pressure, and then depressurized. Samples were taken and analyzed for enantiomeric excess using standard analytical techniques.

EXAMPLE 60

N-Acetyl L-alanine methyl ester via Hydrogenation in THF

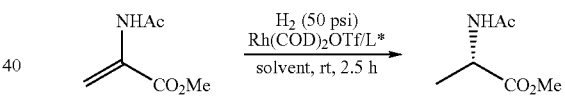

Methy 2-acetamidoacrylate (143 mg, 1.0 mmol) was hydrogenated according to General Procedure under 50 psi of hydrogen in THF using bis(1,5-cyclooctadiene)rhodium trifluoromethanesulfonate (2.3 mg; 5 umol; 0.01 equiv) and ligand (R$_C$, S$_{Fe}$, S$_P$)-23 (3.8 mg; 6 umol; 0.012 equiv) for 2.5 hour to afford 18.6% conversion to amino acid derivative with 88.6% ee as determined by chiral GC analysis.

EXAMPLE 61

N-Acetyl L-alanine methyl ester via Hydrogenation in THF

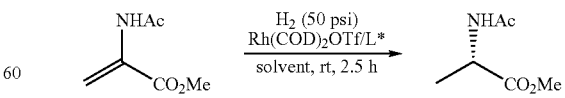

Methy 2-acetamidoacrylate (143 mg, 1.0 mmol) was hydrogenated according to General Procedure under 50 psi of hydrogen in THF using bis(1,5-cyclooctadiene)rhodium trifluoromethanesulfonate (2.3 mg; 5 umol; 0.01 equiv) and ligand (R$_C$, S$_{Fe}$, S$_P$)-24 (4.0 mg; 6 umol; 0.012 equiv) for 2.5 hour to afford 100% conversion to amino acid derivative with 98.3% ee as determined by chiral GC analysis.

EXAMPLE 62

N-Acetyl L-alanine methyl ester via Hydrogenation in THF

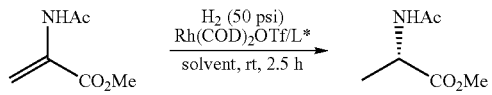

Methy 2-acetamidoacrylate (143 mg, 1.0 mmol) was hydrogenated according to General Procedure under 50 psi of hydrogen in THF using bis(1,5-cyclooctadiene)rhodium trifluoromethanesulfonate (2.3 mg; 5 umol; 0.01 equiv) and ligand ($R_C$, $S_{Fe}$, $R_P$)-25 (4.0 mg; 6 umol; 0.012 equiv) for 2.5 hour to afford 100% conversion to amino acid derivative with 92.3% ee as determined by chiral GC analysis.

EXAMPLE 63

N-Acetyl L-alanine methyl ester via Hydrogenation in MeOH

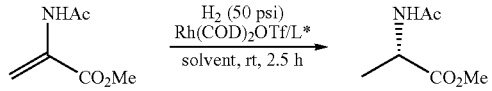

Methy 2-acetamidoacrylate (143 mg, 1.0 mmol) was hydrogenated according to General Procedure under 50 psi of hydrogen in MeOH using bis(1,5-cyclooctadiene)rhodium trifluoromethanesulfonate (2.3 mg; 5 umol; 0.01 equiv) and ligand ($R_C$, $S_{Fe}$, $S_P$)-24 (4.0 mg; 6 mmol; 0.012 equiv) for 2.5 hour to afford 100% conversion to amino acid derivative with >99% ee as determined by chiral GC analysis.

EXAMPLE 64

N-Acetyl L-alanine methyl ester via Hydrogenation in THF with ($R_C$, $S_{Fe}$)-BoaPhoz

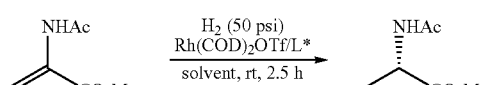

Methy 2-acetamidoacrylate (143 mg, 1.0 mmol) was hydrogenated according to General Procedure under 50 psi of hydrogen in THF using bis(1,5-cyclooctadiene)rhodium trifluoromethanesulfonate (2.3 mg; 5 umol; 0.01 equiv) and ligand ($R_C$, $S_{Fe}$)-BoaPhoz (3.7 mg; 6 umol; 0.012 equiv) for 2.5 hour to afford 99% conversion to amino acid derivative with 94.5% ee as determined by chiral GC analysis.

EXAMPLE 65

N-Acetyl L-phenylalanine methyl ester via Hydrogenation in THF

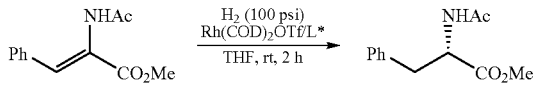

Methy 2-acetamidocinnamate (219 mg, 1.0 mmol) was hydrogenated according to General Procedure under 100 psi of hydrogen in THF using bis(1,5-cyclooctadiene)rhodium trifluoromethanesulfonate (2.3 mg; 5 umol; 0.01 equiv) and ligand ($R_C$, $S_{Fe}$, $S_P$)-23 (3.8 mg; 6 umol; 0.012 equiv) for 2 hour to afford 100% conversion to amino acid derivative with 88.0% ee as determined by chiral GC analysis.

EXAMPLE 66

N-Acetyl L-phenylalanine methyl ester via Hydrogenation in THF

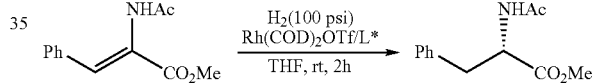

Methy 2-acetamidocinnamate (219 mg, 1.0 mmol) was hydrogenated according to General Procedure under 100 psi of hydrogen in THF using bis(1,5-cyclooctadiene)rhodium trifluoromethanesulfonate (2.3 mg; 5 umol; 0.01 equiv) and ligand ($R_C$, $S_{Fe}$, $S_P$)-24 (4.0 mg; 6 mmol; 0.012 equiv) for 2 hour to afford 100% conversion to amino acid derivative with 97.0% ee as determined by chiral GC analysis.

EXAMPLE 67

N-Acetyl L-phenylalanine methyl ester via Hydrogenation in THF

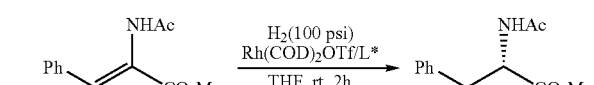

Methy 2-acetamidocinnamate (219 mg, 1.0 mmol) was hydrogenated according to General Procedure under 100 psi of hydrogen in THF using bis(1,5-cyclooctadiene)rhodium trifluoromethanesulfonate (2.3 mg; 5 umol; 0.01 equiv) and ligand ($R_C$, $S_{Fe}$, $R_P$)-25 (4.0 mg; 6 mmol; 0.012 equiv) for 2 hour to afford 100% conversion to amino acid derivative with 92.4% ee as determined by chiral GC analysis.

EXAMPLE 68

N-Acetyl L-phenylalanine methyl methyl ester via Hydrogenation in THF with ($R_C$, $S_{Fe}$)-BoaPhoz

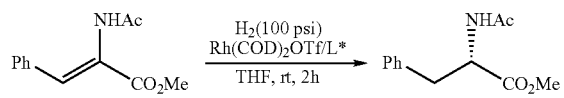

Methy 2-acetamidocinnamate (219 mg, 1.0 mmol) was hydrogenated according to General Procedure under 100 psi of hydrogen in THF using bis(1,5-cyclooctadiene)rhodium trifluoromethanesulfonate (2.3 mg; 5 umol; 0.01 equiv) and ligand ($R_C$, $S_{Fe}$)-BoaPhoz (3.7 mg; 6 umol; 0.012 equiv) for 2 hour to afford 100% conversion to amino acid derivative with 95.7% ee as determined by chiral GC analysis.

REFERENCES

1. T. Hayashi, in Ferrocenes, (Eds.: A. Togni, T. Hayashi), VCH, Weinheim, 1995, p. 105.
2. 2. Togni, A.; Breutel, C.; Schnyder, A.; Spindler, F.; Landert, H.; Tijani, A. J. Am. Chem. Soc. 1994, 116, 4062.
3. 3. a. H. U. Blaser,W. Brieden, B. Pugin, F. Spindler, M. Studer, A. Togni, Topics in Catalysis 2002, 19, 3; b. H. U. Blaser, F.Spindler, M. Studer, Applied Catal. A: General 2001, 221, 119.
4. 4. McGarrity, J.; Spindler, F.; Fuchs, R.; Eyer, M. (LONZA AG), EP-A 624587 A2, 1995; Chem. Abstr. 1995, 122, P81369q.
5. 5. a. Blaser, H.-U. Adv. Synth. Catal. 2002, 344, 17. b. Blaser, H.-U.; Buser, H.-P.; Coers, K.; Hanreich, R.; Jalett, H.-P.; Jelsch, E.; Pugin, B.; Schneider, H.-D.; Spindler, F.; Wegmann, A. Chimia 1999, 53, 275.
6. 6. a. N. W. Boaz, S. D. Debenham, E. B. Mackenzie, S. E. Large, Org. Lett. 2002, 4, 2421. b. Boaz, N. W.; Debenham, S. D. US 2002/0065417 (2002)
7. a) T. Ireland, G. Grossheimann, C. Wieser-Jeunesse, P. Knochel, Angew. Chem. Int. Ed. 1999, 38, 3212. b) T. Ireland, K. Tappe, G. Grossheimann, P. Knochel, Chem. Eur. J. 2002, 8, 843;
8. a) M. Lotz, K. Polbom, P. Knochel, Angew. Chem. Int. Ed. 2002, 41, 4708. b) K. Tappe; P. Knochel, Tetrahedron: Asymmetry 2004, 15, 12; c) M. Lotz, P. Knochel, A. Monsees, T. Riermeier, R. Kadyrov, J. J. Almena Perea, Ger. Pat. No. DE 10219490 (Degussa AG).
9. a) T. Sturm, L. Xiao, W. Weissensteiner, Chimia 2001, 55, 688; b) W. Weissensteiner, T. Sturm, F. Spindler, Adv. Synth. Catal. 2003, 345, 160; c) Weissensteiner, T. Sturm, F. Spindler, US2003212284.
10. a. Perea, A. J. J.; Bomer, A.; Knochel, P. Tetrahedron Lett. 1998, 39, 8073. b. Perea, A. J. J.; Lotz, M.; Knochel, P. Tetrahedron: Asymmetry 1999, 10, 375. c. Lotz, M.; Ireland, T.; Perea, A. J. J.; Knochel, P. Tetrahedron: Asymmetry 1999, 10, 1839. d. Knochel, P.; Perea, A. J. J.; Drauz, K.; Klement, I. U.S. Pat. No. 6,284,925 (2001).
11. (a) Sawamura, M.; Hamashima, H.; Sugawara, M.; Kuwano, N.; Ito, Y. Organometallics 1995, 14, 4549. (b) Sawamura, M.;Kuwano, R.; Ito, Y. J. Am. Chem. Soc. 1995, 117, 9602. (c) Kuwano, R.; Sawamura, M.; Ito, Y. Tetrahedron: Asymmetry 1995, 6, 2521. (d) Kuwano, R.; Okuda, S.; Ito, Y. Tetrahedron: Asymmetry 1998, 9, 2773. (e) Kuwano, R.; Okuda, S.; Ito, Y. J. Org. Chem. 1998, 63, 3499. (f) Kuwano, R.; Ito, Y. J. Org. Chem. 1999, 64, 1232. (g) Kuwano, R.; Sato, K.; Kurokawa, T.; Karube, D.; Ito, Y. J. Am. Chem. Soc. 2000, 122, 7614.
12. a) Kang, J.; Lee, J. H.; Ahn, S. H.; Choi, J. S. Tetrahedron Lett. 1998, 39, 5523. b) Kang, J.; Lee, J. H.; Kim, J. B.; Kim, G. J. Chirality 2000, 12, 378.
13. a) Jendralla, H.; Paulus, E. Synlett, 1997, 471. b) Jendralla, J. H. U.S. Pat. No. 5,856,540 (1999)
14. a) Argouarch, G.; Samuel, O.; Kagan, H. B. Eur. J. Org. Chem. 2000, 2891. b) Argouarch, G.; Samuel, O.; Riant, O.; Daran, J.-C.; Kagan, H. B. Eur. J. Org. Chem. 2000, 2893.
15. Marinetti, A.; Labrue, F.; Genel, J.-P. Synlett 1999, 1975.
16. Berens, U.; Burk, M. J.; Gerlach, A.; Hems, W. Angew. Chem., Int. Ed. Engl. 2000, 39, 1981.
17. You, J.; Drexler, H.-J.; Zhang, S.; Fischer, C.; Heller, D. Angew. Chem., Int. Ed. Engl. 2003, 42, 913.
18. Maienza, F.; Worle, M.; Steffanut, P.; Mezzetti, A. Organometallics 1999, 18, 1041.
19. (a) Nettekoven, U.; Widhalm, M.; Kamer, P. C. J.; van Leeuwen, P. W. N. M. Tetrahedron: Asymmetry 1997, 8, 3185. (b) Nettekoven, U.; Kamer, P. C. J.; van Leeuwen, P. W. N. M.; Widhalm, M.; Spek, A. L.; Lutz, M. J. Org. Chem. 1999, 64, 3996.
20. Liu, D.; Li, W.; Zhang, X. Org. Lett. 2002, 4, 4471.
21. Xiao, D.; Zhang, X. Angew. Chem., Int. Ed. Engl. 2001, 40, 3425.
22. a) M. T. Reetz, A. Gosberg, R. Goddard, S.-H. Kyung, Chem. Commun. 1998, 2077; b) M. T. Reetz, A. Gosberg, WO 0014096, 1998 (assigned to Studiengesellschaft Kohle MBH);
23. a. Nettekoven, U.; Widhalm, M.; Kamer, P. C. J.; van Leeuwen, P. W. N. M.; Mereiter, K.; Lutz, M.; Spek, A. L. Organometallics 2000, 19, 2299. b. Nettekoven, U.; Kamer, P. C. J.; Widhalm, M.; van Leeuwen, P. W. N. M. Organometallics 2000, 19, 4596. c. Nettekoven, U.; Widhalm, M.; Kalchhauser, H.; Kamer, P. C. J.; van Leeuwen, P. W. N. M.; Lutz, M.; Spek, A. L. J. Org. Chem. 2001, 66, 759-770.
24. Barbaro, P.; Bianchini, C.; Giambastiani, G.; Togni, A. Chem. Commun. 2002, 2672.
25. (a) Marquarding, D.; Klusacek, H.; Gokel, G.; Hoffmann, P.; Ugi, I. J. Am. Chem. Soc. 1970, 92, 5389. (b) Marquarding, D.; Klusacek, H.; Gokel, G.; Hoffmann, P.; Ugi, I. Angew. Chem. Int. Ed. Engl. 1970, 9, 371. (c) Hayashi, T.; Yamamoto, K.; Kumada, M. Tetrahedron Lett. 1974, 15, 405. (d) Hayashi, T.; Mise, T.; Fukushima, M.; Kagotani, M.; Nagashima, N.; Hamada, Y.; Matsumoto, A.; Kawakami, S.; Konishi, M. M.; Yamamoto, K.; Kumada, M. Bull. Chem. Chem. Soc. Jpn. 1980, 53, 1138
26. Riant, O.; Argouarch, G.; Guillaneux, D.; Samuel, O.; Kagan, H. B. J. Org. Chem. 1998, 63, 3511.
27. (a) Riant, O.; Samuel, O.; Flessner, T.; Taudien, S.; Kagan, H. B. J. Org. Chem. 1997, 62, 6733. (b) Riant, O.; Samuel, O.; Kagan,H. B. J. Am. Chem. Soc. 1993, 115, 5835.
28. (a) Richards, J.; Damalidis, T.; Hibbs D. E.; Hursthouse, M. B. Synlett 1995, 74. (b) Sammakai, T.; Latham H. A.; Schaad, D. R. J. Org. Chem. 1995, 60, 10. (c) Nishibayashi, Y.; Uemura, S. Synlett 1995, 79. (d) Sammakai, T.; Latham, H. A. J. Org. Chem. 1995, 60, 6002.
29. Ganter, C.; Wagner, T. Chem. Ber. 1995, 128, 1157.
30. (a) Enders, D.; Peters, R.; Lochtman, R.; Runsink, J. Synlett 1997, 1462. (b) Enders, D.; Peters, R.; Lochtman, R.; Runsink, J. Eur. J. Org. Chem. 2000, 2839.

31. Lotz, M.; Ireland T.; Tappe, K.; Knochel, P. Chirality, 2000, 12, 389.
32. Kitzler, R.; Xiao, L.; Weissensteiner, W. Tetrahedron: Asymmetry 2000, 11, 3459.
33. Widhalm, M.; Mereiter, K.; Bourghida, M. Tetrahedron: Asymmetry 1998, 9, 2983.
34. Nishibayashi, Y.; Arikawa, Y.; Ohe, K.; Uemura, S. J. Org. Chem. 1996, 61, 1172.
35. (a) Tsukazaki, M.; Tinkl, M.; Roglans, A.; Chapell, B. J.; Taylor, N.J.; Snieckus, V. J. Am. Chem. Soc. 1996, 118, 685. (b) Jendralla, H.; Paulus, E. Synlett 1997, 471.
36. Price, D.; Simpkins, N. S. Tetrahedron Lett. 1995, 36, 6135.

The invention claimed is:

1. A metallocene-based ligand having a formula selected from the group consisting of Formula (I), Formula (II), Formula (III), Formula (IV), Formula (V), Formula (VI), Formula (VII), Formula (VIII), and Formula (IX):

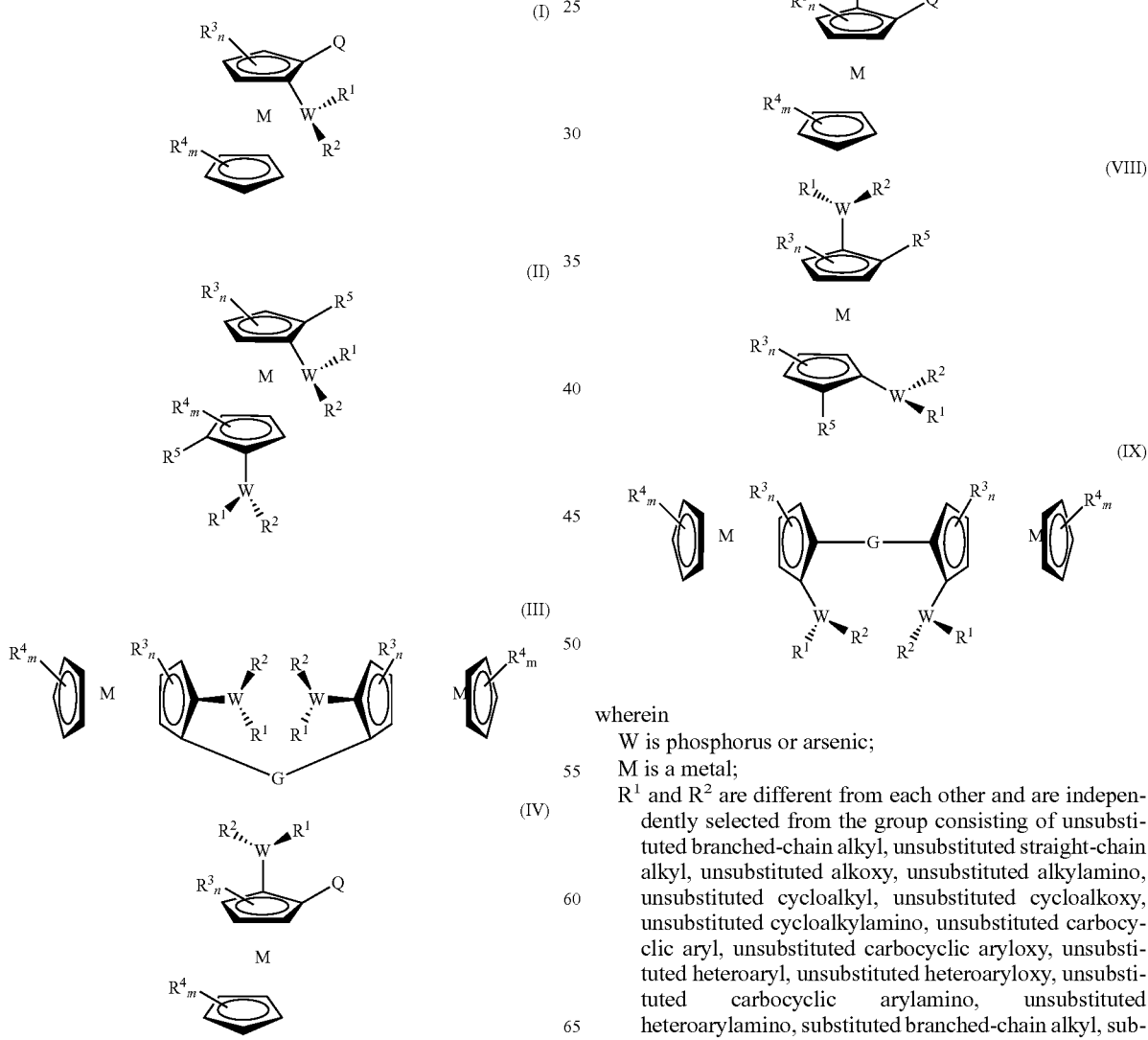

wherein
W is phosphorus or arsenic;
M is a metal;
$R^1$ and $R^2$ are different from each other and are independently selected from the group consisting of unsubstituted branched-chain alkyl, unsubstituted straight-chain alkyl, unsubstituted alkoxy, unsubstituted alkylamino, unsubstituted cycloalkyl, unsubstituted cycloalkoxy, unsubstituted cycloalkylamino, unsubstituted carbocyclic aryl, unsubstituted carbocyclic aryloxy, unsubstituted heteroaryl, unsubstituted heteroaryloxy, unsubstituted carbocyclic arylamino, unsubstituted heteroarylamino, substituted branched-chain alkyl, substituted straight-chain alkyl, substituted alkoxy, substituted alkylamino, substituted cycloalkyl, substituted cycloalkoxy, substituted cycloalkylamino, substituted carbocyclic aryl, unsubstituted carbocyclic aryloxy, substituted heteroaryl, substituted heteroaryloxy, substituted carbocyclic arylamino, and substituted heteroarylamino;

$R^3$ and $R^4$ are independently selected from the group consisting of substituted branched-chain alkyl, substituted straight-chain alkyl, substituted cycloalkyl, substituted carbocyclic aryl, substituted heteroaryl, unsubstituted branched-chain alkyl, unsubstituted straight-chain alkyl, unsubstituted cycloalkyl, unsubstituted carbocyclic aryl, and unsubstituted heteroaryl;

n is an integer from 0 to 3;

m is an integer from 0 to 5;

Q is the group

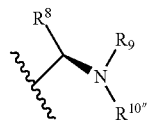

wherein $R^8$ is selected from the group consisting of substituted straight-chain alkyl, substituted branched-chain alkyl, unsubstituted branched-chain alkyl, substituted cycloalkyl, unsubstituted cycloalkyl, substituted carbocyclic aryl, unsubstituted carbocyclic aryl, substituted heteroaryl, and unsubstituted heteroaryl; $R^9$ and $R^{10''}$ are independently selected from the group consisting of hydrogen, substituted straight-chain alkyl, substituted branched-chain alkyl, unsubstituted branched-chain alkyl, substituted cycloalkyl, unsubstituted cycloalkyl, substituted carbocyclic aryl, unsubstituted carbocyclic aryl, substituted heteroaryl, and unsubstituted heteroaryl; or Q is selected from the group consisting of

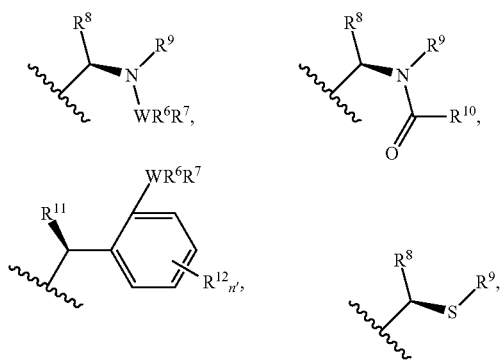

wherein $R^6$ and $R^7$ are independently selected from the group consisting of substituted branched-chain alkyl, substituted straight-chain alkyl, substituted alkoxy, substituted alkylamino, substituted cycloalkyl, substituted cycloalkoxy, substituted cycloalkylamino, substituted carbocyclic aryl, substituted carbocyclic aryloxy, substituted heteroaryl, substituted heteroaryloxy, substituted carbocyclic arylamino, substituted heteroarylamino, unsubstituted branched-chain alkyl, unsubstituted straight-chain alkyl, unsubstituted alkoxy, unsubstituted alkylamino, unsubstituted cycloalkyl, unsubstituted cycloalkoxy, unsubstituted cycloalkylamino, unsubstituted carbocyclic aryl, unsubstituted carbocyclic aryloxy, unsubstituted heteroaryl, unsubstituted heteroaryloxy, unsubstituted carbocyclic arylamino, and unsubstituted heteroarylamino;

$R^8$, $R^9$, and $R^{10}$ are independently selected from the group consisting of hydrogen, substituted straight-chain alkyl, unsubstituted straight-chain alkyl, substituted branched-chain alkyl, unsubstituted branched-chain alkyl, substituted cycloalkyl, unsubstituted cycloalkyl, substituted carbocyclic aryl, unsubstituted carbocyclic aryl, substituted heteroaryl, and unsubstituted heteroaryl; $R^{11}$ is selected from the group consisting of $OR^{13}$, $SR^{13}$, $NHR^{13}$, and $NR^{13}R^{14}$, wherein $R^{13}$ and $R^{14}$ are independently selected from the group consisting of substituted branched-chain alkyl, unsubstituted branched-chain alkyl, substituted cycloalkyl, unsubstituted cycloalkyl, substituted carbocyclic aryl, unsubstituted carbocyclic aryl, substituted heteroaryl, and unsubstituted heteroaryl; $R^{12}$ is selected from the group consisting of hydrogen, halogen, $OR^{13}$, $SR^{13}$, $NR^{13}R^{14}$, substituted branched-chain alkyl, unsubstituted branched-chain alkyl, substituted cycloalkyl, unsubstituted cycloalkyl, substituted carbocyclic aryl, unsubstituted carbocyclic aryl, substituted heteroaryl, and unsubstituted heteroaryl, and n' is 0 to 4;

$R^5$ is selected from:

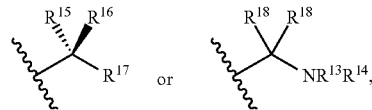

wherein $R^{15}$, $R^{16}$ and $R^{17}$ are independently selected from the group consisting of hydrogen, halogen, $OR^{13}$, $SR^{13}$, $NR^{13}R^{14}$, substituted branched-chain alkyl, unsubstituted branched-chain alkyl, substituted cycloalkyl, unsubstituted cycloalkyl substituted carbocyclic aryl, unsubstituted carbocyclic aryl, substituted heteroaryl, and unsubstituted heteroaryl; and wherein the two geminal substituents $R^{18}$ together are a doubly bonded oxygen atom, or each substituent $R^{18}$ is individually hydrogen; and G is selected from the group consisting of —C(=O)NH—R*—NHCO—, —C(=O)—OR*O—C(=O)—, —C(=O)—R*C(=O)—, —CH=N—R*—N=CH—, —CH$_2$NH—R*—NHCH$_2$—, —CH$_2$NHC(=O)—R*—C(=O)NHCH$_2$—, —CH(R$^8$)NH—R*—NH(CH(R$^8$)—, —CH(R$^8$)NHC(=O)—R*—C(=O)NHCH(R$^8$)—, —C(=O)NH—R—NHC(=O)—, —C(=O)—ORO—C(=O)—, —C(=O)—RC(=O)—, —CH=N—R—N=CH—, —CH$_2$NH—R—NHCH$_2$—, —CH$_2$NHC(=O)—R—C(=O)NHCH$_2$—, —CH(R$^8$)NH—R—NH(CH(R$^8$)—, —CH(R$^8$)NHC(=O)—R—C(=O)NHCH(R$^8$)—;

wherein $R^8$ is independently selected from the group consisting of hydrogen, substituted straight-chain alkyl, unsubstituted straight-chain alkyl, substituted branched-chain alkyl, unsubstituted branched-chain alkyl, substituted cycloalkyl, unsubstituted cycloalkyl, substituted carbocyclic aryl, unsubstituted carbocyclic aryl, substituted heteroaryl, and unsubstituted heteroaryl;

wherein $R^{13}$ and $R^{14}$ are independently selected from the group consisting of substituted branched-chain alkyl, unsubstituted branched-chain alkyl, substituted cycloalkyl, unsubstituted cycloalkyl, substituted carbocyclic aryl, unsubstituted carbocyclic aryl, substituted heteroaryl, and unsubstituted heteroaryl;

—R*— and —R— are selected from the group consisting of:

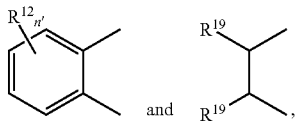

wherein $R^{12}$ is as previously defined;

wherein the two substituents $R^{19}$ together are —$(CH_2)_{m'}$— or each substitutent $R^{18}$ is independently selected from the group consisting of hydrogen, substituted branched-chain alkyl, unsubstituted branched-chain alkyl, substituted cycloalkyl, unsubstituted cycloalkyl, substituted carbocyclic aryl, unsubstituted carbocyclic aryl, substituted heteroaryl, and unsubstituted heteroaryl; wherein the or each heteroatom is independently selected from sulphur, nitrogen, n' is an integer of from 0 to 4; and m' is an integer of from 1 to 8.

2. The metallocene-based ligand of claim 1, which is a diastereomer having Formula (IV), Formula (V), or Formula (VI).

3. The metallocene-based ligand of claim 1, which is an enantiomer having Formula (VII), Formula (VIII), or Formula (IX).

4. The metallocene-based ligand of claim 1, wherein the metallocene-based ligand is a phosphine or arsine having chirality at W, and wherein the metallocene-based ligand has at least one additional element of chirality selected from the group consisting of chirality at carbon, and axial chirality.

5. The metallocene-based ligand of claim 1, wherein the metallocene-based ligand is a diphosphine or diarsine having chirality at W, and wherein the metallocene-based ligand has two additional elements of chirality comprising chirality at carbon, and axial chirality.

6. The metallocene-based ligand of claim 1, wherein the metallocene is ferrocene.

7. The metallocene-based ligand of claim 1, wherein W is phosphorus.

8. A catalyst or catalyst precursor in an asymmetric transformation reaction to generate a high enantiomeric excess of a formed compound, the catalyst or catalyst precursor comprising the metallocene-based ligand of claim 1.

9. A transition metal complex containing a transition metal coordinated to a ligand according to the metallocene-based ligand of claim 1.

10. A transition metal complex according to claim 9, wherein the transition metal is a Group VIb or a Group VIII metal.

11. A method for preparing the metallocene-based ligand of claim 1, comprising:
providing a metallocene-based substrate having a chiral directing substituent on one or both rings;
ortho-lithiating the metallocene-based substrate; and
converting the ortho-lithiated metallocene-based substrate to obtain the metallocene-based ligand.

12. The method according to claim 11, wherein the metallocene-based ligand has Formula (I) or Formula (III), wherein the metallocene-based substrate has Formula (X'):

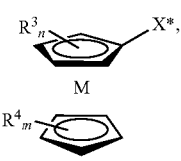

Formula (X')

wherein $R^3$ and $R^4$ are independently selected from the group consisting of substituted branched-chain alkyl, substituted straight-chain alkyl, substituted cycloalkyl, substituted carbocyclic aryl, substituted heteroaryl, unsubstituted branched-chain alkyl, unsubstituted straight-chain alkyl, unsubstituted cycloalkyl, unsubstituted carbocyclic aryl, and unsubstituted heteroaryl;

n is an integer from 0 to 3;
m is an integer from 0 to 5;
and wherein X* is a chiral directing group, wherein the step of converting the ortho-lithiated metallocene-based substrate comprises reacting the ortho-lithiated substrate with an $R^1$ substituted phosphine or arsine, and with an $R^2$-bearing Grignard reagent or an $R^2$-organolithium compound, then converting X* to Q or G.

13. A method according to claim 12, wherein X* is selected from the group consisting of:

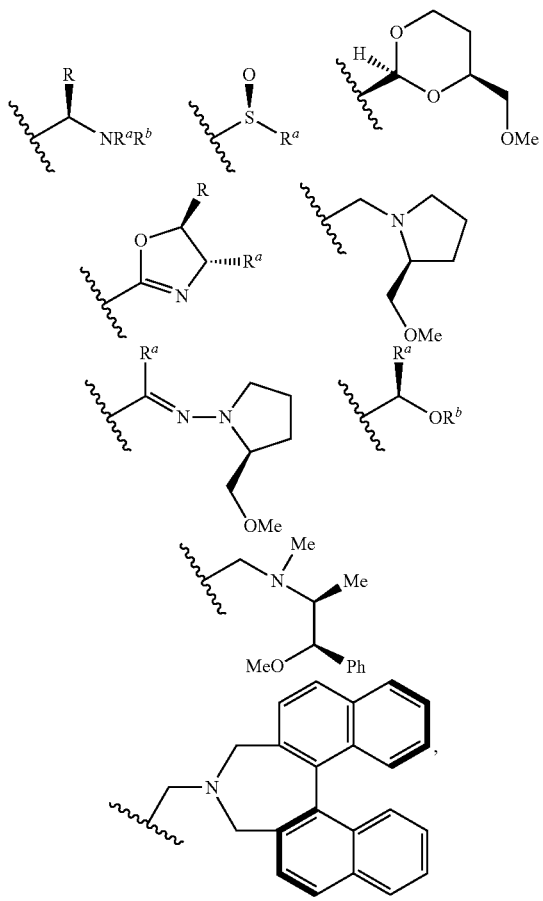

wherein
$R^a$ and $R^b$ are independently selected from the group consisting of substituted branched-chain alkyl, substituted straight-chain alkyl, substituted cycloalkyl, substituted carbocyclic aryl, substituted heteroaryl, unsubstituted branched-chain alkyl, unsubstituted straight-chain alkyl, unsubstituted cycloalkyl, unsubstituted carbocyclic aryl, and unsubstituted heteroaryl.

14. The method according to claim 12, wherein the ortho-lithiation step is conducted using at least one lithiating agent selected from the group consisting of n-butyllithium, sec-butyllithium, and tert-butyllithium.

15. The method according to claim 14, wherein the step of converting the ortho-lithiated metallocene-based substrate comprises reacting the ortho-lithiated metallocene-based substrate in situ with a dichlorophosphine of the formula $R^1PCl_2$ wherein $R^1$ is selected from the group consisting of unsubstituted branched-chain alkyl, unsubstituted straight-chain alkyl, unsubstituted alkoxy, unsubstituted alkylamino, unsubstituted cycloalkyl, unsubstituted cycloalkoxy, unsubstituted cycloalkylamino, unsubstituted carbocyclic aryl, unsubstituted carbocyclic aryloxy, unsubstituted heteroaryl, unsubstituted heteroaryloxy, unsubstituted carbocyclic arylamino, unsubstituted heteroarylamino, substituted branched-chain alkyl, substituted straight-chain alkyl, substituted alkoxy, substituted alkylamino, substituted cycloalkyl, substituted cycloalkoxy, substituted cycloalkylamino, substituted carbocyclic aryl, substituted carbocyclic aryloxy, substituted heteroaryl, substituted heteroaryloxy, substituted carbocyclic arylamino, and substituted heteroarylamino; to yield an intermediate product, wherein the intermediate product is converted to obtain the metallocene-based ligand.

16. The method according to claim 15, further comprising reacting the intermediate product with an organometallic reagent of formula $R^2Z$, wherein $R^2$ is selected from the group consisting of unsubstituted branched-chain alkyl, unsubstituted straight-chain alkyl, unsubstituted alkoxy, unsubstituted alkylamino, unsubstituted cycloalkyl, unsubstituted cycloalkoxy, unsubstituted cycloalkylamino, unsubstituted carbocyclic aryl, unsubstituted carbocyclic aryloxy, unsubstituted heteroaryl, unsubstituted heteroaryloxy, unsubstituted carbocyclic arylamino, unsubstituted heteroarylamino, substituted branched-chain alkyl, substituted straight-chain alkyl, substituted alkoxy, substituted alkylamino, substituted cycloalkyl, substituted cycloalkoxy, substituted cycloalkylamino, substituted carbocyclic aryl, substituted carbocyclic aryloxy, substituted heteroaryl, substituted heteroaryloxy, substituted carbocyclic arylamino, and substituted heteroarylamino;

wherein Z is Li or MgY, and wherein Y is a halide, to obtain a phosphorus chiral compound having formula (XI'):

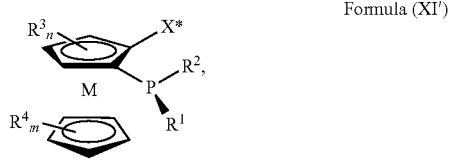

Formula (XI')

wherein the phosphorous chiral compound is converted to obtain the metallocene-based ligand.

17. A method for preparing a metallocene-based ligand of claim 1, comprising:
providing a compound of Formula (XXXVII):

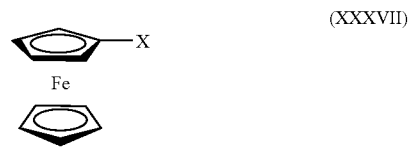

(XXXVII)

wherein X is an achiral directing group;
subjecting the compound of Formula (XXXVII) to enantioselective mono-ortho-lithiation using at least one lithiating agent selected from the group consisting of n-butyllithium, sec-butyllithium, and tert-butyllithium, wherein the mono-ortho-lithiation is conducted in the presence of a homochiral tertiary amine, whereby a chiral monolithium compound is obtained; reacting the chiral monolithium compound in situ with a dichlorophosphine of the formula $R^1PCl_2$ followed by reacting with an organometallic reagent of the formula $R^2Z$, wherein $R^1$ and $R^2$ are different from each other and are independently selected from the group consisting of unsubstituted branched-chain alkyl, unsubstituted straight-chain alkyl, unsubstituted alkoxy, unsubstituted alkylamino, unsubstituted cycloalkyl, unsubstituted cycloalkoxy, unsubstituted cycloalkylamino, unsubstituted carbocyclic aryl, unsubstituted carbocyclic aryloxy, unsubstituted heteroaryl, unsubstituted heteroaryloxy, unsubstituted carbocyclic arylamino, unsubstituted heteroarylamino, substituted branched-chain alkyl, substituted straight-chain alkyl, substituted alkoxy, substituted alkylamino, substituted cycloalkyl, substituted cycloalkoxy, substituted cycloalkylamino, substituted carbocyclic aryl, substituted carbocyclic aryloxy, substituted heteroaryl, substituted heteroaryloxy, substituted carbocyclic arylamino, and substituted heteroarylamino;

wherein Z is Li or MgY, and wherein Y is a halide, to obtain a phosphorus chiral compound having Formula (XXXVIII):

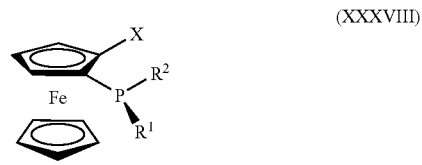

(XXXVIII)

and converting the phosphorus chiral compound having Formula (XXXVIII) to the metallocene-based ligand, wherein the metallocene-based ligand has Formula (I) or Formula (III).

18. The method according to claim 17, wherein X is selected from the group consisting of:

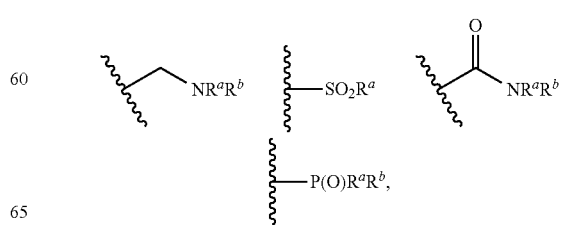

wherein $R^a$ and $R^b$ are independently selected from the group consisting of substituted branched-chain alkyl, substituted straight-chain alkyl, substituted cycloalkyl, substituted carbocyclic aryl, substituted heteroaryl, unsubstituted branched-chain alkyl, unsubstituted straight-chain alkyl, unsubstituted cycloalkyl, unsubstituted carbocyclic aryl, and unsubstituted heteroaryl.

19. A method for preparing a metallocene-based ligand of claim 1, comprising:
providing a compound of the Formula (XXXIX):

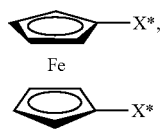

(XXXIX)

wherein X* is a chiral directing group;
subjecting the compound of Formula (XXXIX) to bis-ortho-lithiation using at least one lithiating agent selected from the group consisting of n-butyllithium, sec-butyllithium, and tert-butyllithium, whereby a bis-lithium compound in situ with a dichlorophosphine of the formula $R^1PCl_2$ followed by reacting with an organometallic reagent of the formula $R^2Z$ wherein $R^1$ and $R^2$ are different from each other and are independently selected from the group consisting of unsubstituted branched-chain alkyl, unsubstituted straight-chain alkyl, unsubstituted alkoxy, unsubstituted alkylamino, unsubstituted cycloalkyl, unsubstituted cycloalkoxy, unsubstituted cycloalkylamino, unsubstituted carbocyclic aryl, unsubstituted carbocyclic aryloxy, unsubstituted heteroaryl, unsubstituted heteroaryloxy, unsubstituted carbocyclic arylamino, unsubstituted heteroarylamino, substituted branched-chain alkyl, substituted straight-chain alkyl, substituted alkoxy, substituted alkylamino, substituted cycloalkyl, substituted cycloalkoxy, substituted cycloalkylamino, substituted carbocyclic aryl, substituted carbocyclic aryloxy, substituted heteroaryl, substituted heteroaryloxy, substituted carbocyclic arylamino, and substituted heteroarylamino;
wherein Z is Li or MgY, and wherein Y is a halide, to obtain a phosphorus chiral compound having Formula (XXXX):

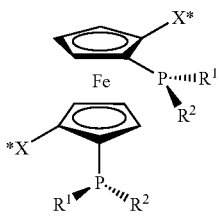

(XXXX)

and converting the phosphorous chiral compound having Formula (XXX) to the metallocene-based ligand, wherein the metallocene-based ligand has Formula (II).

* * * * *